(12) United States Patent
Khalapyan

(10) Patent No.: US 7,799,073 B2
(45) Date of Patent: Sep. 21, 2010

(54) ANNULOPLASTY SYSTEM AND SURGICAL METHOD

(76) Inventor: Tigran Khalapyan, 205 Hallmark North, Hershey, PA (US) 17033

( * ) Notice: Subject to any disclaimer, the term of this patent is extended or adjusted under 35 U.S.C. 154(b) by 0 days.

(21) Appl. No.: 11/776,915

(22) Filed: Jul. 12, 2007

(65) Prior Publication Data

US 2008/0065203 A1     Mar. 13, 2008

Related U.S. Application Data

(63) Continuation of application No. 60/807,119, filed on Jul. 12, 2006.

(51) Int. Cl.
*A61F 2/24* (2006.01)
*A61B 17/04* (2006.01)

(52) U.S. Cl. ...................... 623/2.37; 606/232

(58) Field of Classification Search ....... 623/2.36–2.41, 623/5.12, 2.11; 606/232, 233, 148
See application file for complete search history.

(56) References Cited

U.S. PATENT DOCUMENTS

| | | | |
|---|---|---|---|
| 4,917,698 A * | 4/1990 | Carpentier et al. | 623/2.36 |
| 5,053,047 A | 10/1991 | Yoon | |
| 5,064,431 A * | 11/1991 | Gilbertson et al. | 623/2.37 |
| 5,269,783 A | 12/1993 | Sander | |
| 5,709,695 A * | 1/1998 | Northrup, III | 606/148 |
| 5,824,066 A * | 10/1998 | Gross | 623/2.36 |
| 5,961,539 A * | 10/1999 | Northrup et al. | 606/232 |
| 6,840,246 B2 | 1/2005 | Downing | |
| 6,921,407 B2 | 7/2005 | Nguyen et al. | |
| 6,986,775 B2 * | 1/2006 | Morales et al. | 606/139 |
| 7,063,722 B2 | 6/2006 | Marquez | |
| 7,220,277 B2 | 5/2007 | Arru et al. | |
| 2002/0128708 A1 | 9/2002 | Northrup, III et al. | |
| 2002/0162611 A1 | 11/2002 | Hashiguchi | |
| 2004/0162611 A1 | 8/2004 | Marquez | |
| 2004/0236419 A1 * | 11/2004 | Milo | 623/2.36 |
| 2005/0137700 A1 | 6/2005 | Spence et al. | |
| 2006/0020336 A1 | 1/2006 | Liddicoat | |
| 2008/0004697 A1 * | 1/2008 | Lichtenstein et al. | 623/2.11 |

OTHER PUBLICATIONS

International Search Report for PCT/US2007/073356, mailed Jul. 30, 2008.

* cited by examiner

*Primary Examiner*—Corrine McDermott
*Assistant Examiner*—Cheryl Miller
(74) *Attorney, Agent, or Firm*—McNees Wallace & Nurick LLC

(57) ABSTRACT

An annuloplasty system for repairing incompetent heart valves is provided. This system includes a substantially circular valve reinforcing device adapted to be surgically implanted into around a heart valve annulus; anchoring means for attaching the substantially circular valve reinforcing device to the heart valve, wherein attaching the substantially circular valve reinforcing device to the heart valve annulus reduces the circumference of the heart valve annulus by plicating annular tissue underneath the valve reinforcing device; and constricting means for, if necessary, reducing the circumference of the substantially circular valve reinforcing device, wherein reducing the circumference of the substantially circular valve reinforcing device further reduces the circumference of the heart valve annulus.

8 Claims, 63 Drawing Sheets

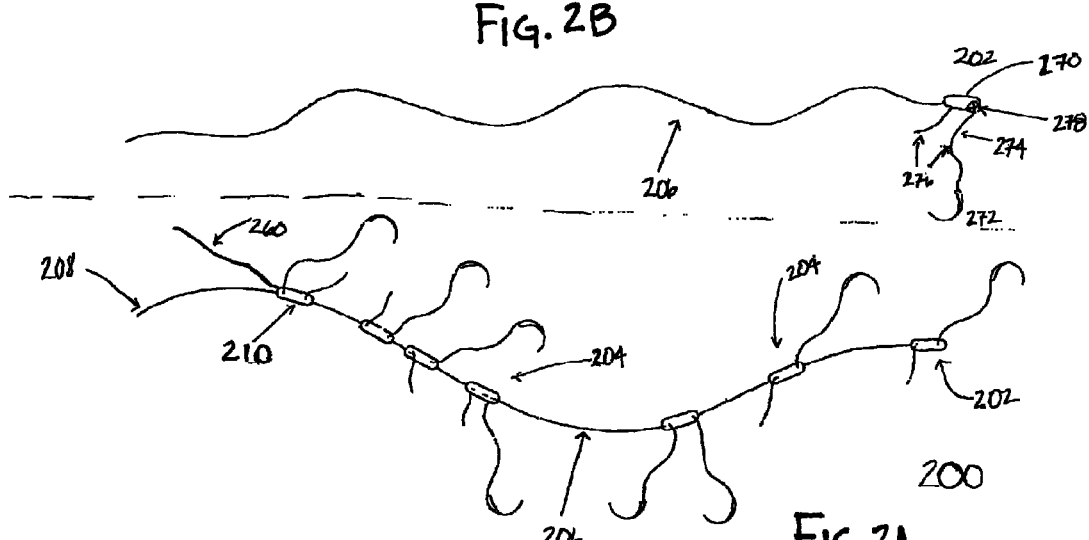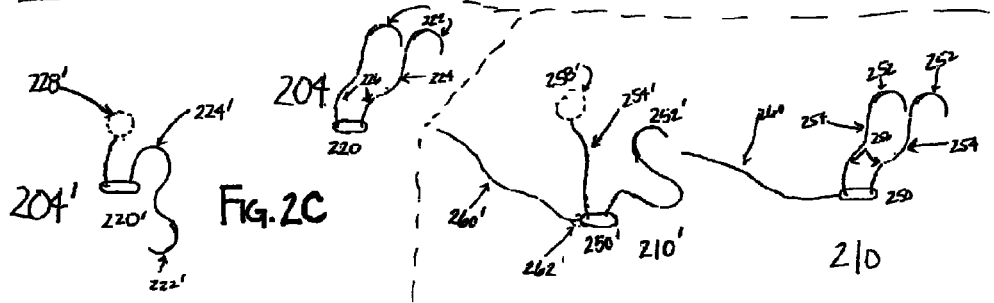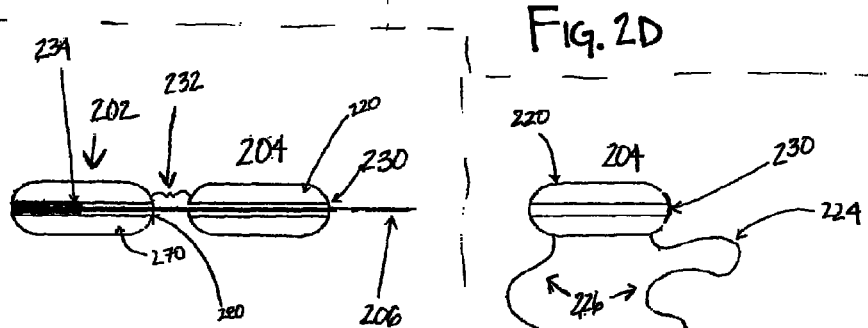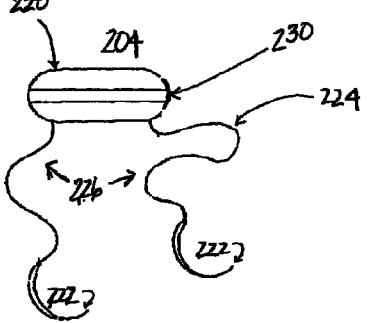

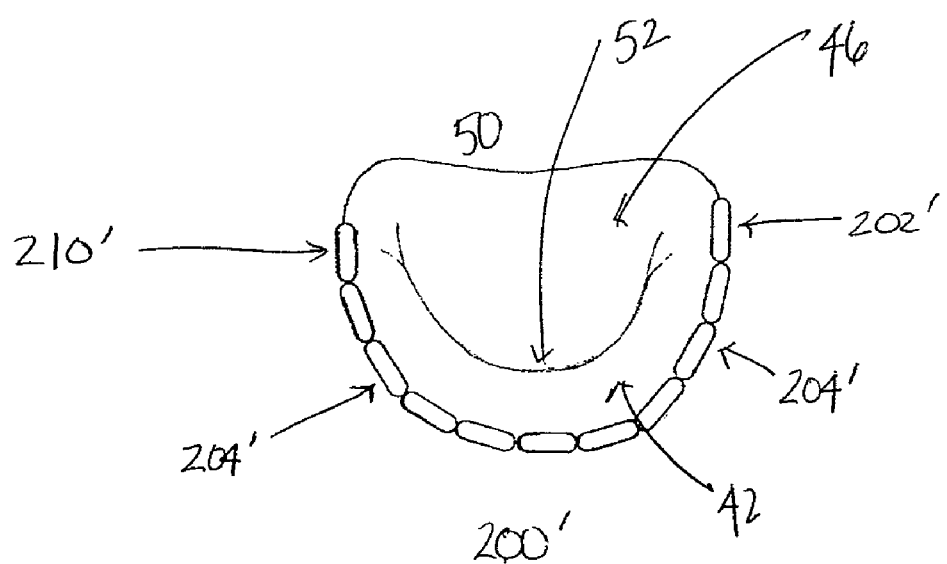
FIG. ZZ

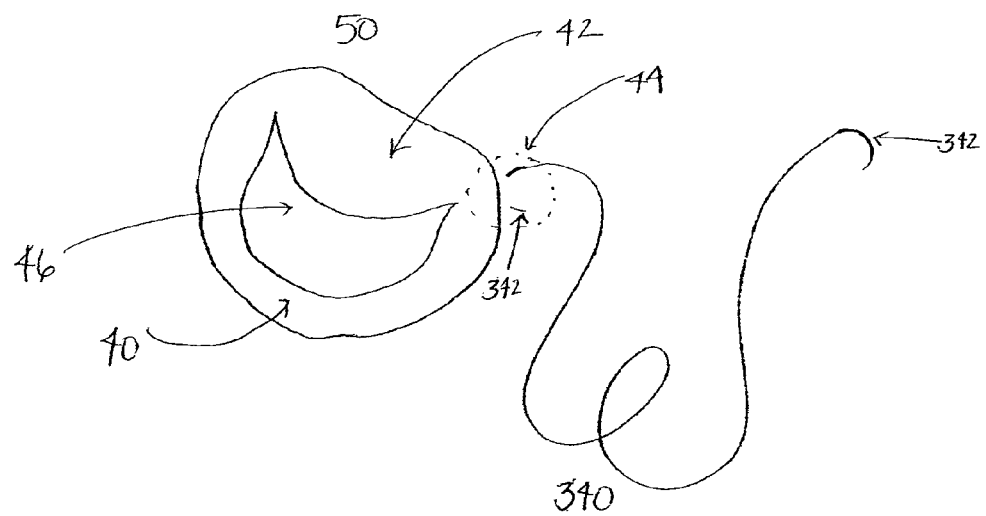
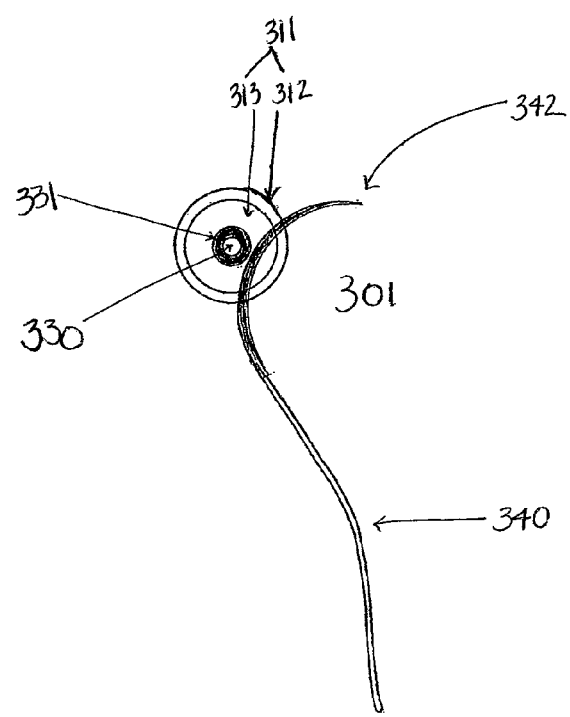
FIG. 3A

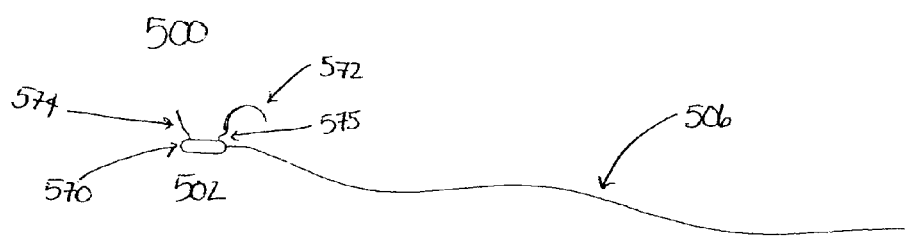
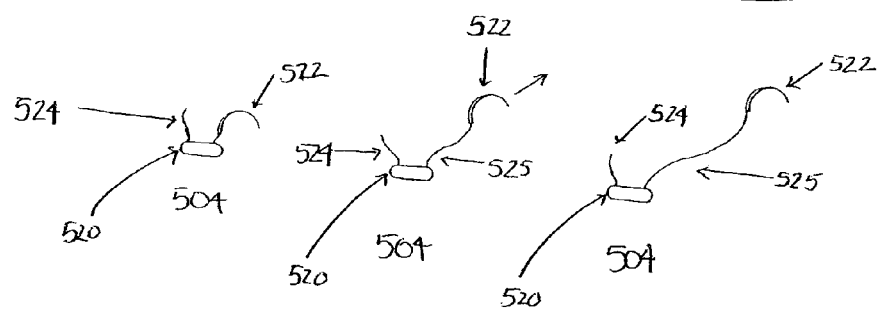
FIG. 5

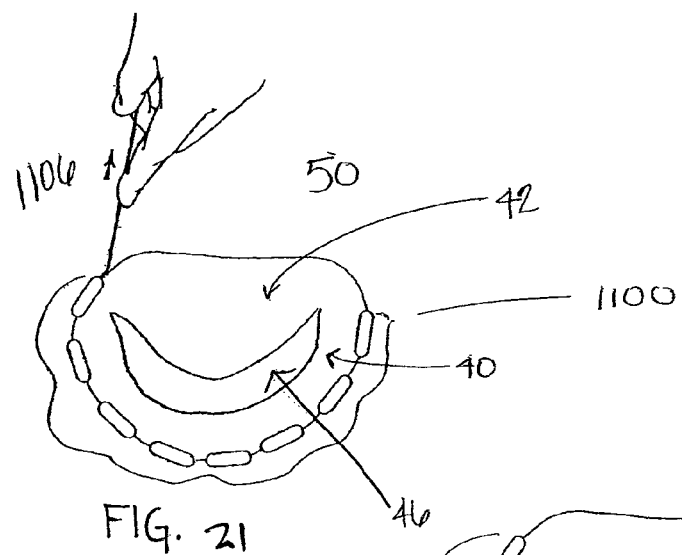
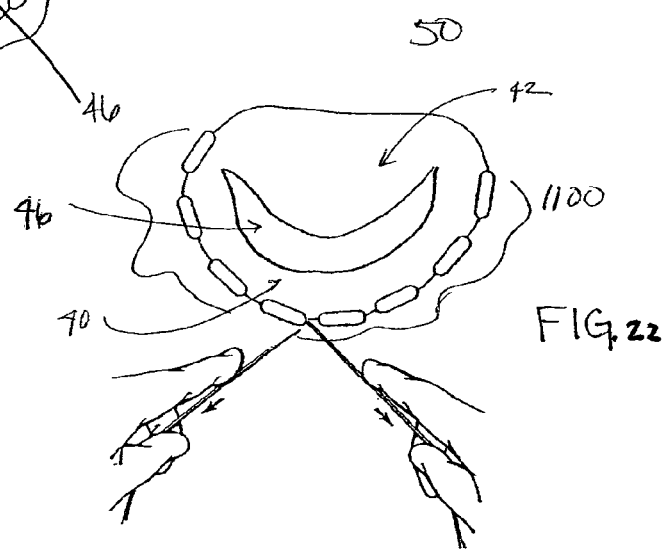
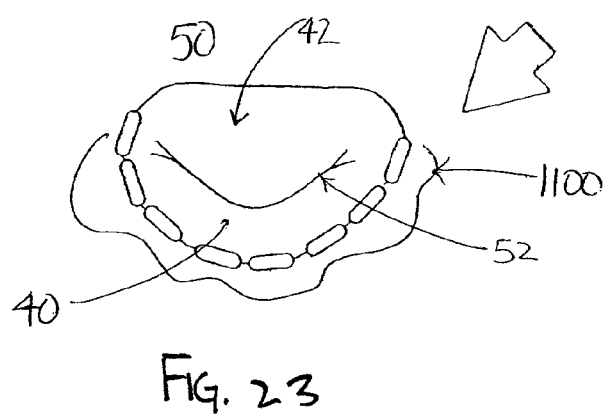

ANNULOPLASTY SYSTEM AND SURGICAL METHOD

CROSS-REFERENCE TO RELATED APPLICATIONS

This patent application claims the benefit of U.S. Provisional Patent Application Ser. No. 60/807,119 filed on Jul. 12, 2006 and entitled "Annuloplasty Ring and Surgical Method," the disclosure of which is incorporated by reference as if fully rewritten herein.

BACKGROUND OF THE INVENTION

The described invention relates in general to surgical systems, devices, and methods and more specifically to an annuloplasty system for damaged heart valve repair. This invention is useful for humans and may be used for the surgical correction of a deformed heart valve, and in particular a heart valve that has become dilated.

Diseases of the mitral valve affect the annulus, altering annular geometry and function. Dilation and/or deformation of the valve annulus result in the displacement of the cusps away from the center of the valve. This results in an ineffective closure of the valve during ventricular contraction, which results in the regurgitation or leakage of blood during ventricle contraction.

Two known surgical methods or techniques, generally referred to as annuloplasty, are typically used to reshape the distended and/or deformed valve annulus. In the technique known as "plication", the circumference of the valve annulus is reduced by implanting a prosthetic ring of reduced circumference about the base of the annulus while the annulus is pleated to reduce its circumference to that of the ring. In the technique known as "reconstruction", the circumference of the annulus is not reduced, but the annulus is restructured into an elongate shape. To accomplish this goal, a rigid or semi-rigid ring (e.g., the Carpentier ring) having the same circumference as the annulus but in an elliptical shape is surgically implanted about the base of the valve. Both plication and restructuring are intended to eliminate the gap in the closure of the distended valve by bringing back together the tips of the valve cusps, reinforce suture lines, and prevent further annular dilatation.

Interrupted sutures of 2/0 braided synthetic material with double-end needles are typically used for the described surgical methods. The stitches are placed into the fibrous tissue of the annulus. Large bites of the heart annulus are taken, and the needles are passed close together through the ring prosthesis. The annuloplasty ring is slid down over the sutures into position above the mitral valve and the sutures are tied firmly, attaching the device to the annulus. As the sutures are tied down to approximate the prosthetic ring to the mitral valve annulus, the annular diameter is reduced and the contour is improved.

A hypothetically "ideal" annuloplasty would correct the dilatation of the posterior annulus in a measured fashion while allowing a full range of motion of the mitral annulus. Initially the prostheses were designed as rigid and flat frame members, to correct the dilation and reshape the valve annulus to the natural state. However, rigidity impedes the beneficial flexing movements and displacements of the native annulus during the cardiac cycle. Another disadvantage with highly rigid ring prosthesis is the tendency of the sutures to tear during the normal movement of the valve annulus.

Recognizing that the annulus is a dynamic structure that changes dramatically with the cardiac cycle, thereby facilitating a reduction in mitral orifice size to allow leaflet apposition, flexible annuloplasty rings have been developed. Flexible annuloplasty rings (e.g., the Duran ring) have been shown to minimize risk of dehiscence because there is reduced tension on sutures and reduced negative consequences of inaccurate placement of ring sutures. However, one disadvantage of the completely flexible ring prostheses is that during the implantation process the drawstring effect of the sutures tends to bunch the material covering the flexible ring at localized areas. The rigidity of the Carpentier ring prevents deformity, whereas when the Duran flexible ring is sutured to the annulus by interrupted U-stitches multiple plications of the Dacron polyester fabric occur. This bunching of the prosthesis resulted in the phenomenon known as multiple plications of the ring prosthesis. One result of this phenomenon is variability of the ability of the ring to control the shape of the valve annulus. Each plication of the posterior annulus is dependent on the tension placed on the sutures at the time of tying. Therefore, it is possible to have too small a plication resulting in insufficiency or too large a plication resulting in valve stenosis. Plication of the annuloplasty ring determines a reduction of at least one or two sizes in the selected flexible ring. The residual stenotic effect without early homodynamic repercussion, together with progression of the underlying disease, may be a predisposing factor toward valve stenosis necessitating late reoperation. Some patients in whom the Duran flexible ring had been inserted required valve-related operations as a result of hemolysis with or without prosthetic dehiscence. Patients who underwent reoperation for mitral restenosis showed absence of endothelium in the areas in which the ring was folded. In series of 85 patients reviewed after 10 to 12 years, Duran and coauthors (Duran CG, J L Pomar and J M Revuelta et al., Conservative operation for mitral insufficiency, J Thorac Cardiovasc Surg 79 (1980), pp. 326-337) found a 20.1% incidence of thromboembolic complications. The over narrowing and purse-string effects with irregular contour of the totally flexible ring were the main causes of high rate of thromboembolism.

While rigid and semi-rigid annuloplasty rings eliminate the bunching caused by flexible rings, the restrictive nature of such rings is generally detrimental to the valve's ability to open and close normally. On the other hand, because of their flexibility, flexible rings can be difficult to handle during surgical manipulations and generally must be supported during implantation by a holder, which is subsequently removed before tying off the implanting sutures. The Cosgrove Band is totally flexible; however, bunching of the Cosgrove Band is prevented by the suturing of the device on a rigid template subsequently removed after the implanting sutures are tied off. The approach of tying down over a rigid template eliminates the potential of plication of an inappropriate amount of the posterior annulus of the heart.

The rigid template is in turn releasably secured to a bendable handle to facilitate positioning of the template and ring in the heart adjacent to the annulus of the valve to be repaired. Once the template is placed and sutures initiated, the handle is withdrawn to give the surgeon room to work and properly see the annulus. When the procedure is completed, valve closure is tested by injecting saline solution. The sutures attaching the ring to the template are then cut, and the template is removed, leaving the ring in place. Such templates, however, do not prevent the ring from bunching or pleating when the implant sutures are tied off, if the sutures are not precisely placed. The removal of the sutures, which attach the annuloplasty ring to the holder, can be cumbersome and time consuming. Cutting the sutures can also cause damage to the annuloplasty ring. Care must be taken to ensure that pieces of the suture remain attached to the holder and are not left in the patient. The drag from the suture can make it difficult to remove the ring from the holder. Further, the retention sutures can be captured by the sutures used to implant the ring, thereby creating great difficulty in removing the ring from the holder.

Using conventional techniques, most valve repair procedures require a gross thoracotomy, usually in the form of a median sternotomy or right thoracotomy, to gain access into the patient's thoracic cavity. Using such open-chest techniques enables the surgeon to see the affected valve directly, and to position his or her hands within the thoracic cavity in close proximity to the exterior of the heart for manipulation of surgical instruments and introduction of an annuloplasty ring through the atriotomy for attachment within the heart. However, these invasive, open-chest procedures produce a high degree of trauma, a significant risk of complications, an extended hospital stay, and a painful recovery period for the patient.

Minimally invasive surgery (MIS) enables valve repair without opening the chest cavity. Such minimally invasive heart valve repair surgeries still require bypass, but the procedures are accomplished by means of elongated tubes or cannulas introduced through one or more small access incisions in the thorax, with the help of endoscopes and other such visualization techniques. Such minimally invasive procedures usually provide speedier recovery for the patient with less pain and bodily trauma, thereby reducing the medical costs and the overall disruption to the life of the patient. The use of a minimally invasive approach, however, introduces new complexities to surgery thus placing a greater burden on the operating surgeon. Most notably, minimally invasive approaches drastically reduce the size of the surgical field available to the surgeon for the manipulation of tissue and for the introduction of necessary surgical instruments. These complexities are especially acute in connection with heart surgery. Unlike common heart surgeries performed using a full medial sternotomy, minimally invasive heart surgery offers a surgical field that may be only as large as a resected intercostal space or a transversely cut and retracted sternum. Consequently, the introduction and proper positioning of tools, such as annuloplasty ring holders, and other such devices, becomes a great deal more complicated.

The primary barriers to widespread adoption of minimally invasive, robot assisted (MIRA) cardiac procedures are associated with increased cardiopulmonary bypass (CPB) times and increased surgical skill requirements. Current MIRA technology does not reduce the need for CPB during cardiac procedure. To the contrary bypass times associated with some MIRA cardiac procedures are actually increased. For many MIRA cardiac procedures, the increased time on CPB limits the potential benefits and leads to the exclusion of high-risk patients.

Suture management is a primary contributor to increased CPB times in MIRA cardiac procedures. Typical mitral valve repairs involve 15-20 sutures, each requiring 5-6 knots, causing suturing to consume the majority of operating time. Surgeons are typically very experienced and comfortable tying knots with their hands, but robotic technology adds another level of complexity to this task. Knot tying with surgical robots, particularly using the smaller 2-0 sutures required for mitral valve prosthesis fixation, takes considerably longer than with minimally invasive surgical instruments. The large number of required knots in annuloplasty fixation, coupled with the increased difficulty in tying the knots robotically, cause MIRA mitral valve repair to take longer than minimally invasive surgical approaches. Operating within limited space and with limited vision, it is not surprising that surgeons require more time to tie knots in MIRA surgery, despite the assistance of tele-robotic system. Furthermore, current commercial robotic surgery systems provide no force feedback from the instruments and dexterity with current minimally invasive instruments, manual or robotic, is less than optimal. Because there is no tactile sensation, the knot tying depends on visual clues as to appropriate tension and tightness.

An improved method of suture-based knotless fixation for MIRA mitral valve repair could allow surgeons all of the flexibility and precision of current techniques, while requiring less time and training to perform. Such an improvement could allow more patients to benefit more fully from the potential of MIRA cardiac surgery through increased access and reduced cost. By reducing CPB time, more patients will be candidates for MIRA cardiac procedures. Reduced CPB time will also help reduce direct surgical cost and indirect cost associated with post-surgical recovery.

One final problem associated with the annuloplasty rings of the prior art is that when such annuloplasty rings are implanted into children or adolescents the subsequent growth of the patient may render the annuloplasty ring too small, thus abnormally constricting the annulus. Follow-up surgery would be necessary to replace the originally implanted annuloplasty ring with a larger ring suitable for the current size of the patient. However, the tissue of the heart valve annulus grows into the fabric of the ring making such surgery problematic. Therefore the preservation of growth potential in the native annulus is an important issue in terms of long-term stability of valve repair procedures in children and adolescents.

What is needed, therefore, are devices and methods for carrying out heart valve repair that reduce the trauma, risks, recovery time and pain that accompany current techniques. The devices and methods should facilitate surgical intervention without the need for a gross thoracotomy. In particular, the devices and methods should enable the implantation of annuloplasty repair segments without the need for excessive additional implements.

SUMMARY OF THE INVENTION

The following provides a summary of exemplary embodiments of the annuloplasty system according to the present invention. This summary is not an extensive overview and is not intended to identify key or critical aspects or elements of the present invention or to delineate its scope.

In accordance with one aspect of the present invention, and in general terms, an annuloplasty system for repairing incompetent heart valves or other tissues is provided. This system includes a substantially circular valve reinforcing device adapted to be surgically implanted around a heart valve annulus; anchoring means for attaching the substantially circular valve reinforcing device to the heart valve annulus, wherein attaching the substantially circular valve reinforcing device to the heart valve annulus reduces the circumference of the annulus by plicating annular tissue underneath the valve reinforcing device; and constricting means for reducing the circumference of the substantially circular valve reinforcing device, wherein reducing the circumference of the substantially circular valve reinforcing device further reduces the circumference of the heart valve annulus. The structural (e.g., valve) reinforcing device of this invention is generally flexible in nature; however, the basic component parts thereof (i.e., individual segments), do not typically deform when sutured into the areas of the body that the device is intended to reinforce.

In accordance with another aspect of the present invention, and also in general terms, a method for surgically implanting the annuloplasty system described in the previous paragraph is provided. This method includes utilizing the anchoring means to secure the substantially circular valve reinforcing device to the heart valve annulus, wherein securing the substantially circular valve reinforcing device to the heart valve annulus reduces the circumference of the heart valve annulus by plicating annular tissue underneath the valve reinforcing device; testing the implanted annuloplasty system to verify that appropriate and/or desired constriction has been achieved; and utilizing the constricting means to reduce the circumference of the substantially circular valve reinforcing device if appropriate and/or desired constriction has not been achieved, wherein reducing the circumference of the substantially circular valve reinforcing device further reduces the circumference of the heart valve annulus.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more exemplary embodiments of the invention and, together with the general description given above and detailed description given below, serve to explain the principles of the invention, and wherein:

FIGS. 2B-F are various views of the suture support segments that are included in the annuloplasty system of FIG. 2A.

FIGS. 2G-O illustrate an exemplary method for surgically implanting the annuloplasty system of FIG. 2A in a dilated heart valve.

FIGS. 2P-2Z illustrate an exemplary method for surgically implanting the annuloplasty systems of FIGS. 1A and 2A in a dilated heart valve using robotic assisted surgery.

FIGS. 2AA-2AC illustrate a method for surgically implanting the annuloplasty system of FIG. 2A in an infant or child.

FIGS. 3A-3E illustrate a third exemplary embodiment of the annuloplasty system and surgical implantation method of the present invention wherein a dual-armed suture that is not attached to a suture support segment and a single supportive drawstring are utilized.

FIGS. 5-7 illustrate an annuloplasty system that utilizes a suture material stored within a suture support segment which is pulled out of the support segment once the suture is needed, as well as single or multiple supportive drawstrings.

FIGS. 21-23 illustrate various methods of tightening the supportive drawstring.

DETAILED DESCRIPTION OF THE INVENTION

Figure 1A:
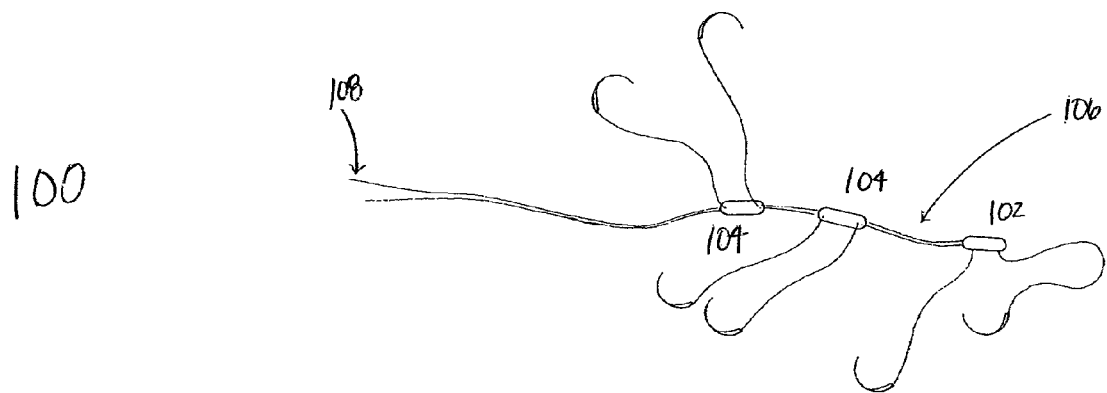
FIG. 1A is top view of a first exemplary embodiment of the annuloplasty system of the present invention wherein the system includes flexible dual-supportive drawstrings.

Exemplary embodiments of the present invention are now described with reference to the Figures. Reference numerals are used throughout the detailed description to refer to the various elements and structures. In other instances, well-known structures and devices are shown in block diagram form for purposes of simplifying the description. Although the following detailed description contains many specifics for the purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

The present invention relates to an annuloplasty system for repairing incompetent heart valves. A first general embodiment of this invention provides an annuloplasty system that utilizes various suture support segments and two supportive drawstrings; a second general embodiment of this invention provides an annuloplasty system that utilizes various suture support segments and one supportive drawstring; a third general embodiment of this invention provides an annuloplasty system that utilizes segments having a sewing cuff, a plurality of sutures, and a supportive drawstring; a fourth general embodiment of this invention provides an annuloplasty system that utilizes suture apparatus having barbed structures and an annuloplasty band or ring; and a fifth general embodiment of this invention provides an annuloplasty system that utilizes only suture support segments. With reference now to the Figures, various specific embodiments of this invention shall be described in greater detail.

A first exemplary embodiment of this invention (shown in FIGS. 1A-N) provides an annuloplasty system for repairing incompetent heart valves. This system includes: a substantially circular valve reinforcing device adapted to be surgically implanted around a heart valve annulus; anchoring means for attaching the substantially circular valve reinforcing device to the heart valve annulus, wherein attaching the substantially circular valve reinforcing device to the heart valve annulus reduces the circumference of the annulus by plicating annular tissue underneath the valve reinforcing device; and constricting means for reducing the circumference of the substantially circular valve reinforcing device, wherein reducing the circumference of the substantially circular valve reinforcing device further reduces the circumference of the annulus. The valve reinforcing device further includes: (i) a plurality of individual suture support segments, wherein the plurality of suture support segments further includes: a) at least one anchor segment, wherein the anchor segment further includes at least two channels passing lengthwise therethrough; and b) a plurality of intermediate segments adapted to be implanted into the heart valve annulus after the anchor segment, wherein each intermediate segment further includes at least two channels passing lengthwise therethrough. The anchoring means further includes: (i) at least two sutures attached to the anchor segment, wherein at least one of the sutures includes a surgical needle attached thereto; and (ii) at least two sutures attached to the intermediate segment wherein at least one of the sutures includes a surgical needle attached thereto. The constricting means further includes: at least two supportive drawstrings, wherein one end of each drawstring is attached to one end of the anchor segment, wherein each of the drawstrings passes through the channels in each intermediate segment, and wherein the ends of the drawstrings are tied together over the last intermediate segment after the heart valve repair is completed.

A method for surgically implanting this annuloplasty system includes: (a) utilizing the anchoring means for securing the substantially circular valve reinforcing device to the heart valve annulus, wherein securing the substantially circular valve reinforcing device to the heart valve annulus reduces the circumference of the heart valve annulus by plicating annular tissue underneath the valve reinforcing device; and (b) utilizing the constricting means to reduce the circumference of the substantially circular valve reinforcing device if appropriate constriction has not been achieved, wherein reducing the circumference of the valve reinforcing device further reduces the circumference of the heart valve annulus by plicating the annular tissue between adjacent segments of the substantially circular valve reinforcing device. Utilizing the anchoring means further includes: (i) affixing the anchor segment to a dilated heart valve annulus by passing one of the surgical needles attached to the sutures on the anchor segment through the heart valve annulus; (ii) pulling the needle and suture which has passed through the heart annulus until the anchor segment aligns with the heart valve annulus; (iii) securing the anchor segment to the heart valve annulus by tying the ends of the sutures on the anchor segment together; (iv) using the supportive drawstrings to guide the intermediate segment through a minimally-invasive tube or small incision to the position above the heart valve annulus adjacent to the anchor segment; (v) affixing the intermediate segment to the heart valve annulus by passing one of the surgical needles attached to the sutures on the intermediate segment through the heart valve annulus; (vii) pulling the surgical needle and suture which has passed through the heart annulus until the intermediate segment aligns with the heart valve annulus; (viii) securing the intermediate segment to the heart valve annulus by tying the ends of the sutures on the intermediate segment together; (ix) repeating steps (iv)-(vii) until the desired circumference around the heart valve annulus is covered by intermediate suture support segments; and (ix) testing the repaired heart valve to verify that appropriate constriction has been achieved. Utilizing the constricting means further includes: (i) pulling both ends of the supportive drawstrings to the desired tension to further decrease the circumference of the heart valve annulus; and (ii) tying the ends of the supportive drawstrings around the last intermediate segment.

FIG. 1A illustrates a dual-supportive drawstring annuloplasty system 100 having an anchor suture support segment 102 with supportive drawstrings 106 attached, and a plurality of intermediate suture support segments 104 threaded through the supportive drawstrings 106. The supportive drawstrings 106 have a free end 108 wherein approximately 10-14 intermediate suture support segments (not shown) 104 are added after the anchor suture support segment 102 to the supportive drawstring to form a flexible dual-supportive drawstring annuloplasty system 100.

Figure 1B:
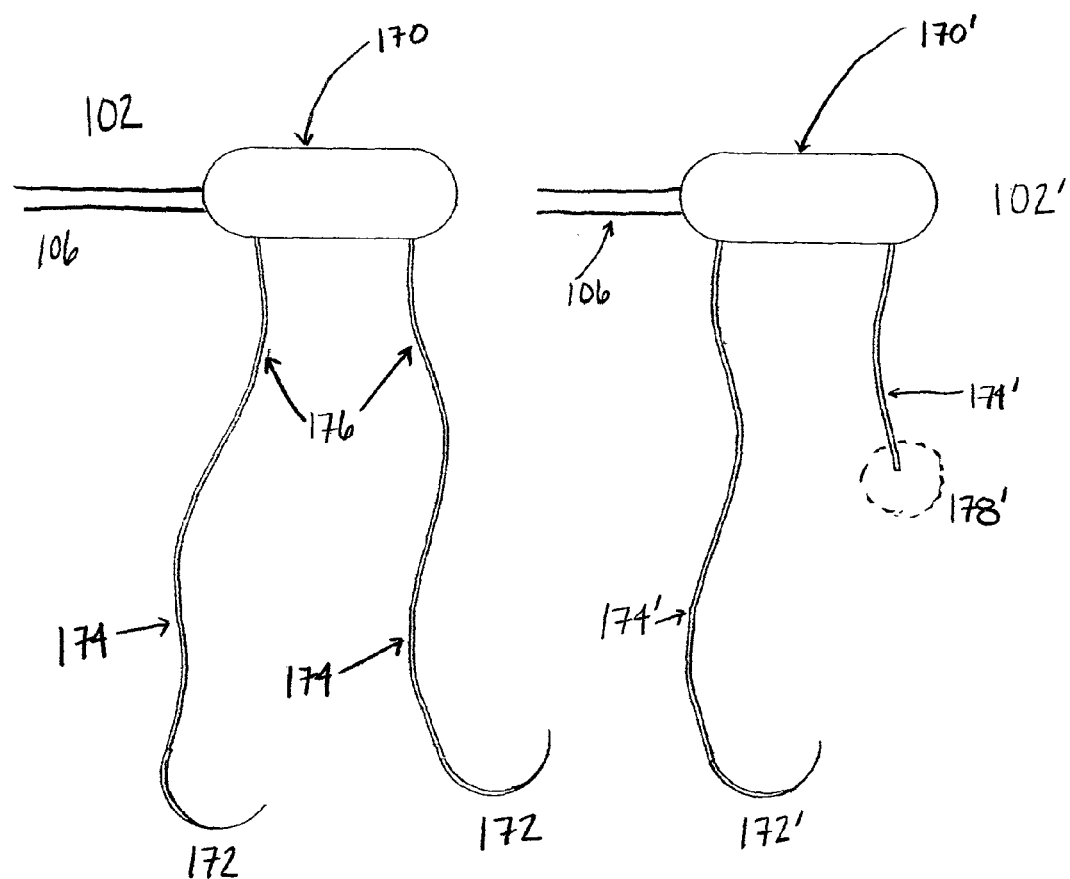
FIGS. 1B-E are various views of the suture support segments that are included in the annuloplasty system of FIG. 1A.

FIGS. 1B-1E provide various views of the elements that comprise the flexible dual-supportive drawstring annuloplasty system 100. FIG. 1B depicts the detail of an anchor suture support segment 102. The anchor suture support segment 102 is made up of an anchor suture support segment body 170, at least one surgical needle 172, and at least one suture 174. The anchor suture support segment body 170 may be made from any material that is radio-opaque, preferably inert, non-corrosive, non-thormbogenic and bio-compatible with blood and tissue. By way of example, but not limitation, such material might be a barium sulfate impregnated acetal resin Delrin. The anchor suture support segment body 170 can be cylindrical, tubular, square, round, oval, elongated oval or combinations thereof shaped as necessary to achieve the desired configuration. The anchor suture support segment body 170 may have a textured blood-contacting surface or may be coated, in whole or in part, by a material designed to promote tissue in-growth and reduce thromboemblosim. By way of example, but not limitation, such material might be Dacron, polyester velour or some other suitable material. A preferred size of the anchor suture support segment body 170 is 1 mm to 4 mm in length but more preferably 2 mm to 6 mm in length, with a circumference of 1 mm to 4 mm, although other sizes and dimensions are possible. Attached to the anchor suture support segment body 170 is at least one suture 174, but more preferably two sutures 174. The anchor suture support segment body 170 must be rigid or semi-rigid in the longitudinal direction, and must not be deformable, such that when the sutures 174 are tied against the anchor suture support segment body 170, to secure the anchor suture support segment 102 to the mitral valve annulus 50, the anchor suture support segment body 170 does not buckle.

The material for the suture 174 may be of any conventional type used in surgical procedures such as 2/0 braided suture, mono-filament suture, or polyfilament suture. The length of each of the sutures 174 may range between 1 centimeter to 25 centimeters, and more preferably between 2 centimeters to 10 centimeters. The sutures 174 are attached to the side of the anchor suture support segment body 170 in such a way as to create a dual-armed suture structure 176. Attached to the free ends of each suture 174 is a surgical needle 172. The surgical needle 172 is attached to the suture 174 by a conventional swedging process. The surgical needle 172 is a conventional curved surgical needle. Such surgical needles or suture needles are generally known and are normally made from a corrosion-resistant metal, preferably chrome-nickel steel.

FIG. 1B also shows an alternative embodiment where the anchor suture support segment 102' has an anchor suture support segment body 170' with attached suture 174'. Only one of the sutures 174' has attached to the free end a surgical needle 172' and the second suture 174' has a free end 178' without a surgical needle 172'.

Figure 1C:
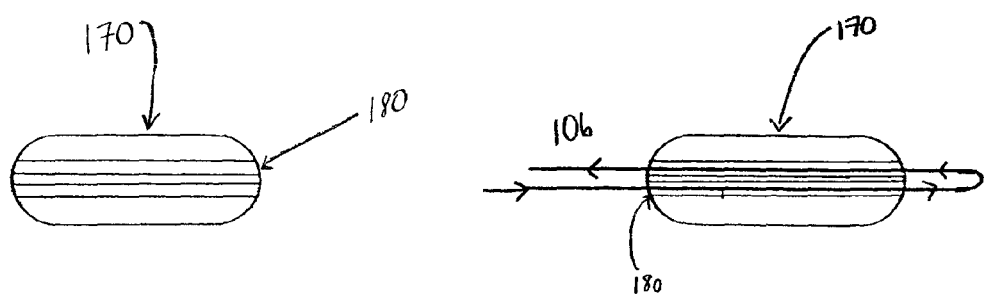

FIG. 1C shows a cross sectional view of an anchor suture support segment body 170 with dual-channels 180. One end of the supportive drawstring 106 is treaded through one of the dual-channels 180 in the anchor suture support segment body 170 to a desired length and then that same end of the supportive drawstring 106 is looped around the channel opening and treaded back through the other channel 180 of the anchor suture support segment body 170 to create a dual supportive drawstring 106. The supportive drawstring 106 may be comprised of suture material, Teflon strip, a band, a filament, a wire or a strap.

Figure 1D:
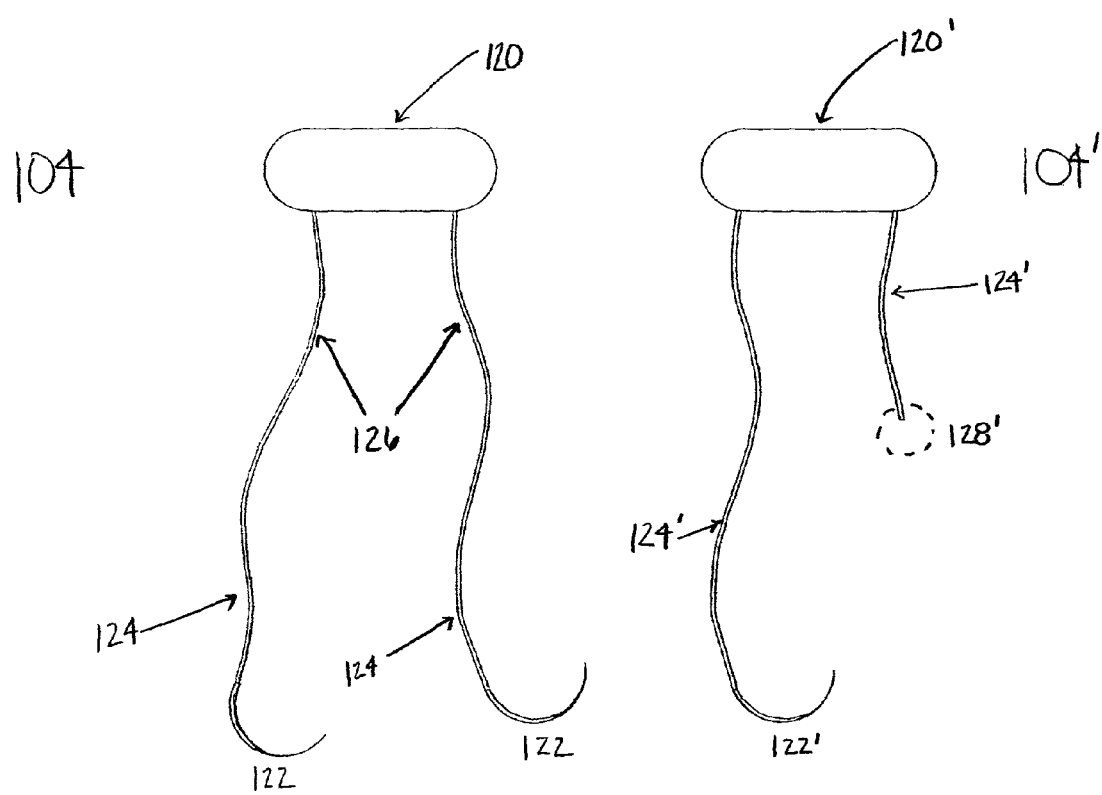

FIG. 1D depicts the detail of an intermediate suture support segment 104. The intermediate suture support segment 104 is made up of an intermediate suture support segment body 120, at least one surgical needle 122, and at least one suture 124. The intermediate suture support segment body 120 may be made from any material that is radio-opaque, preferably inert, non-corrosive, non-thormbogenic and bio-compatible with blood and tissue. By way of example, but not limitation, such material might be a barium sulfate impregnated acetal resin Delrin. The intermediate suture support segment body 120 can be a cylindrical, a tubular, a square, a round, an oval, an elongated oval or the like shaped as necessary to achieve the desired configuration. The intermediate suture support segment body 120 may have a textured blood-contacting surface or may be coated, in whole or in part, by a material designed to promote tissue in-growth and reduce thromboemblosim. By way of example, but not limitation, such material might be Dacron, polyester velour or some other suitable material. A preferred size of the intermediate suture support segment body 120 is 1 mm to 4 mm in length but more preferably 2 mm to 6 mm in length, with a circumference of 1 mm to 4 mm, although other sizes and dimensions are possible. Attached to the intermediate suture support segment body 120 is at least one suture 124, but more preferably two sutures 124. The intermediate suture support segment body 120 must be rigid or semi-rigid in the longitudinal direction, and must not be deformable, such that when the sutures 124 are tied against the intermediate suture support segment body 120, to secure the intermediate suture support segment body 120 to the mitral valve annulus 50, the intermediate suture support segment body 120 does not buckle.

The material for the suture 124 may be of any conventional type used in surgical procedures such as 2/0 braided suture, mono-filament suture, or polyfilament suture. The length of the suture 124 may range between 1 centimeter to 25 centimeters, and more preferably between 2 centimeters to 10 centimeters. The sutures 124 are attached to the side of the intermediate suture support segment body 120 in such a way as to create a dual-armed suture structure 126. Attached to the free ends of each suture 124 is a surgical needle 122. The surgical needle 122 is attached to the suture 124 by a conventional swedging process. The surgical needle 122 is a conventional curved surgical needle. Such surgical needles or suture needles are generally known and are normally made from a corrosion-resistant metal, preferably chrome-nickel steel.

FIG. 1D also shows an alternative embodiment where the intermediate suture support segment 104' has an intermediate suture support segment body 120' with attached suture 124'. Only one of the sutures 124' has attached to the free end a surgical needle 122' and the second suture 124' has a free end 128' without a surgical needle 122'.

Figure 1E:
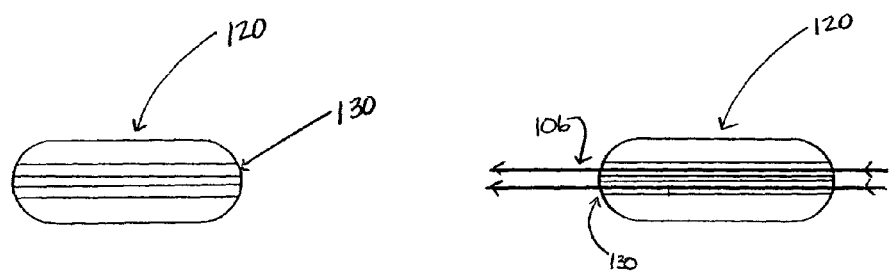

FIG. 1E shows a cross sectional view of an intermediate suture support segment body 120 with dual-channels 130. Both free ends 108 of the supportive drawstrings 106 are threaded through the dual-channels 130 in the intermediate suture support segment body 120. The supportive drawstrings 106 prevent against inadvertently dropping the intermediate support segments into the heart cavity and facilitate the delivery of the intermediate support segments 104 to the remote implantation site during surgery. The intermediate suture support segments can be slid down over the supportive drawstrings into position above the mitral valve from outside of the chest cavity through a small incision or port.

FIGS. 1F-1N depict a method of implantation of the dual-supportive drawstring annuloplasty system 100 described in FIGS. 1A-1E. The surgical methods used to implant the annuloplasty system 100 may be conventional open heart surgery techniques or minimally invasive heart surgery techniques. FIGS. 1F-1N provide an illustration of the superior view of the mitral valve of a human heart. The mitral valve includes a fibrous annulus 50 and anterior and posterior leaflets 42, 40. In a healthy heart the leaflets close tightly during systole and do not allow any of the blood to flow backwards through the mitral valve into the left atrium. However, one consequence of a number of cardiac diseases is that mitral valve annulus 50 becomes dilated so that the anterior and posterior leaflets 42 and 40 cannot close tightly during systole, thereby creating gap 46 between the anterior and posterior leaflets 42 and 40. As a result, mitral valve regurgitation occurs, resulting in some of the blood flowing backwards through the incompletely closed mitral valve leaflets into the left atrium.

Figure 1F:
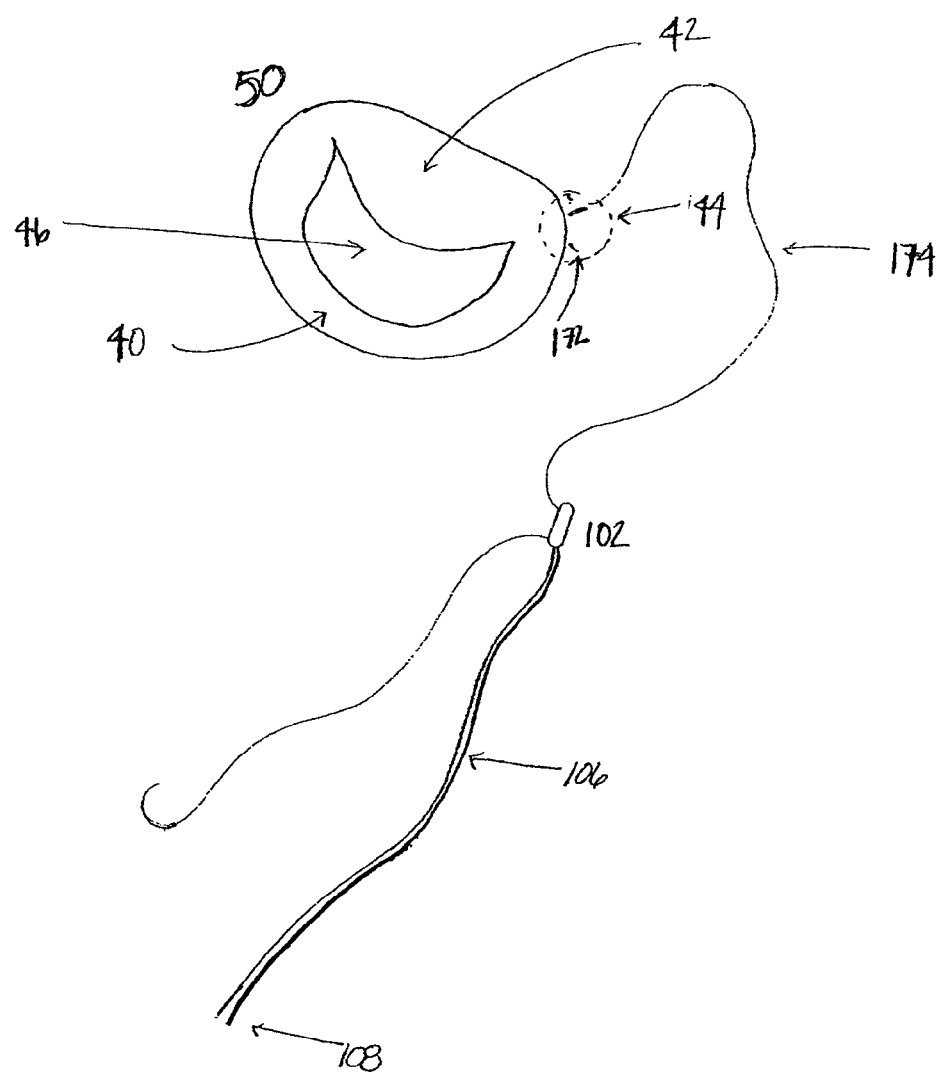
FIGS. 1F-S illustrate an exemplary method for surgically implanting the annuloplasty system of FIG. 1A in a dilated heart valve.

FIG. 1F depicts the first step of the method of implantation which is to guide the surgical needle 172 of the anchor suture support segment 102 into the surgical site 44 on the mitral valve annulus 50. The surgical needle 172 and suture 174 will be passed through the mitral valve annulus 50 in a conventional surgical technique so as to make a horizontal mattress stitch. As shown in FIG. 1A the anchor suture support segment 102 has attached to the distal end supportive drawstrings 106 that have a free end 108.

Figure 1G:
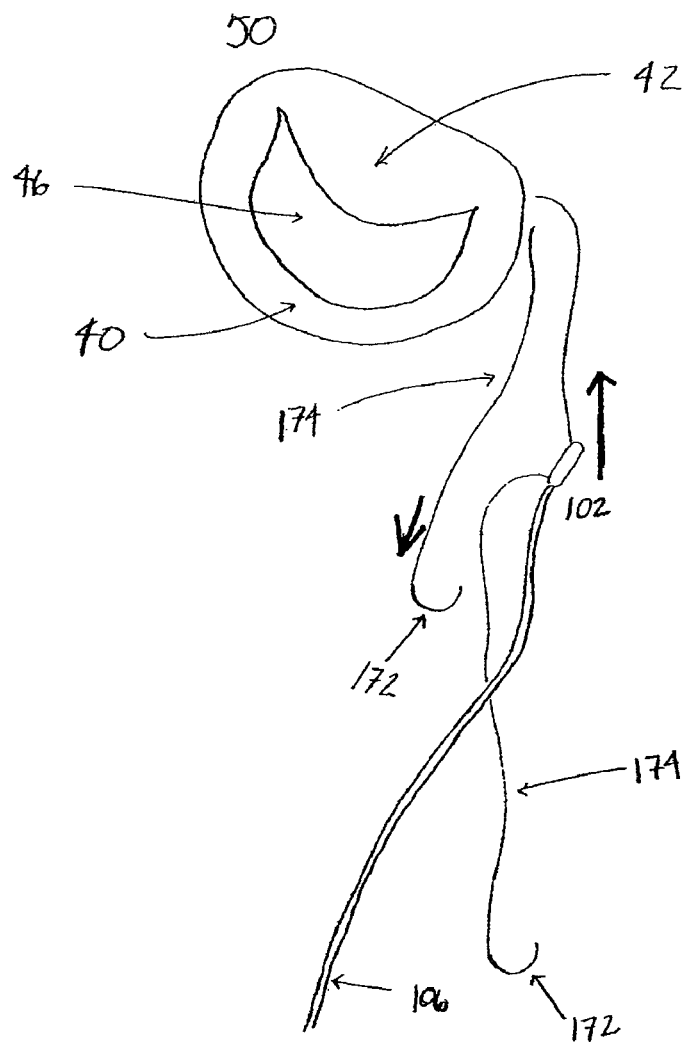

FIG. 1G shows the next step in the method of implantation. The surgeon will continue to pull the surgical needle 172 and suture material 174, which has passed through surgical site 44, away from the mitral valve annulus 50 which will bring the anchor suture support segment 102 flush with the mitral valve annulus 50.

Figure 1H:
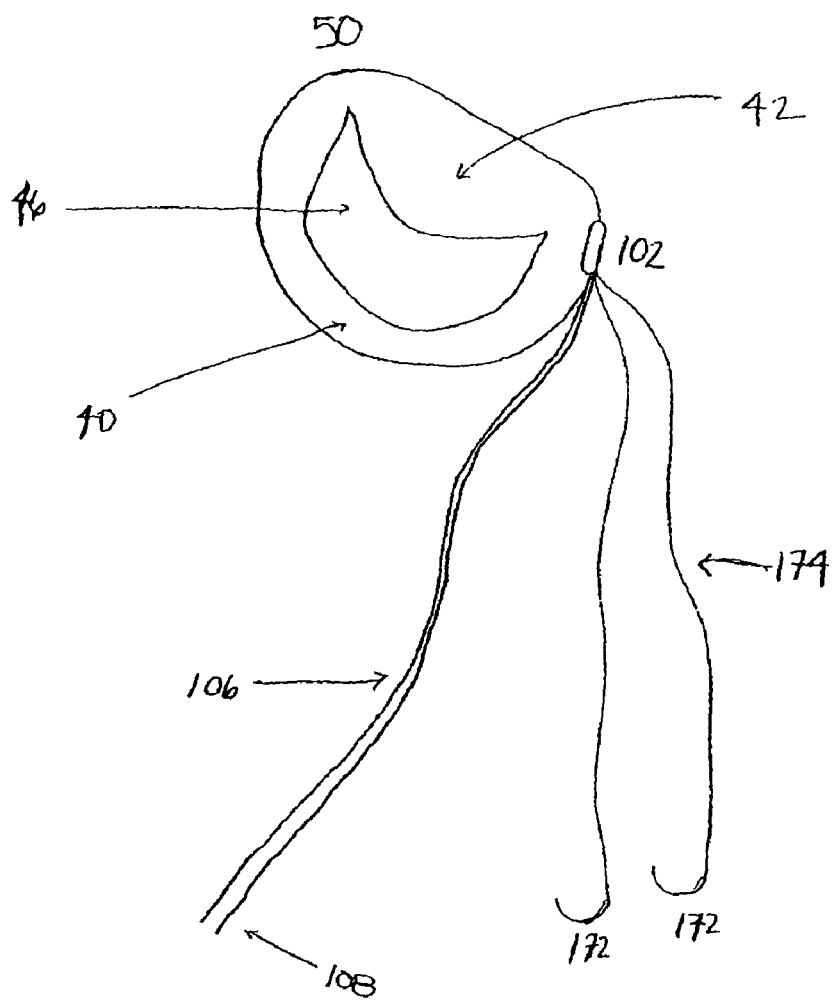
Figure 1I:
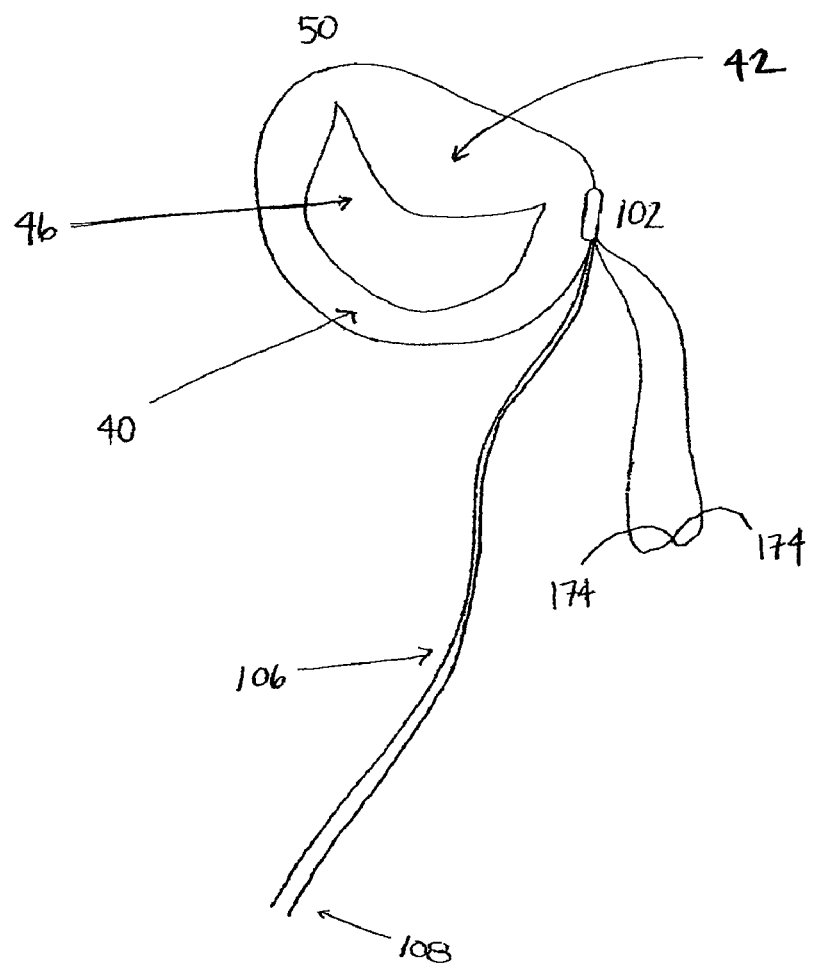

FIG. 1H depicts the anchor suture support segment 102 aligned with the mitral valve annulus 50. To secure the anchor suture support segment 102 the surgeon will first cut off the surgical needles 172 from each of the sutures 174 (not shown). Next, as depicted in FIG. 1I the surgeon will tie the two free ends of the sutures 174 together with sufficient tension thereby securing the anchor suture support segment 102 in place on the mitral valve annulus 50. After five or six knots have been made the free tails of the sutures 174 are cut by any suitable means (not shown). The suture 174 traverses a longer distance along the mitral valve annulus 50 than the distance between two suture attachments in the side of the anchor suture support segment body 170. Sutures 174, when tightened and tied, create an imbrication in the mitral valve annulus 50 underneath the segment thereby reducing the circumference of the mitral valve annulus 50 by an amount equal to the difference between the length each suture travels in the tissue of the heart annulus and the distance between the suture attachments in the support segment (not shown).

Figure 1J:
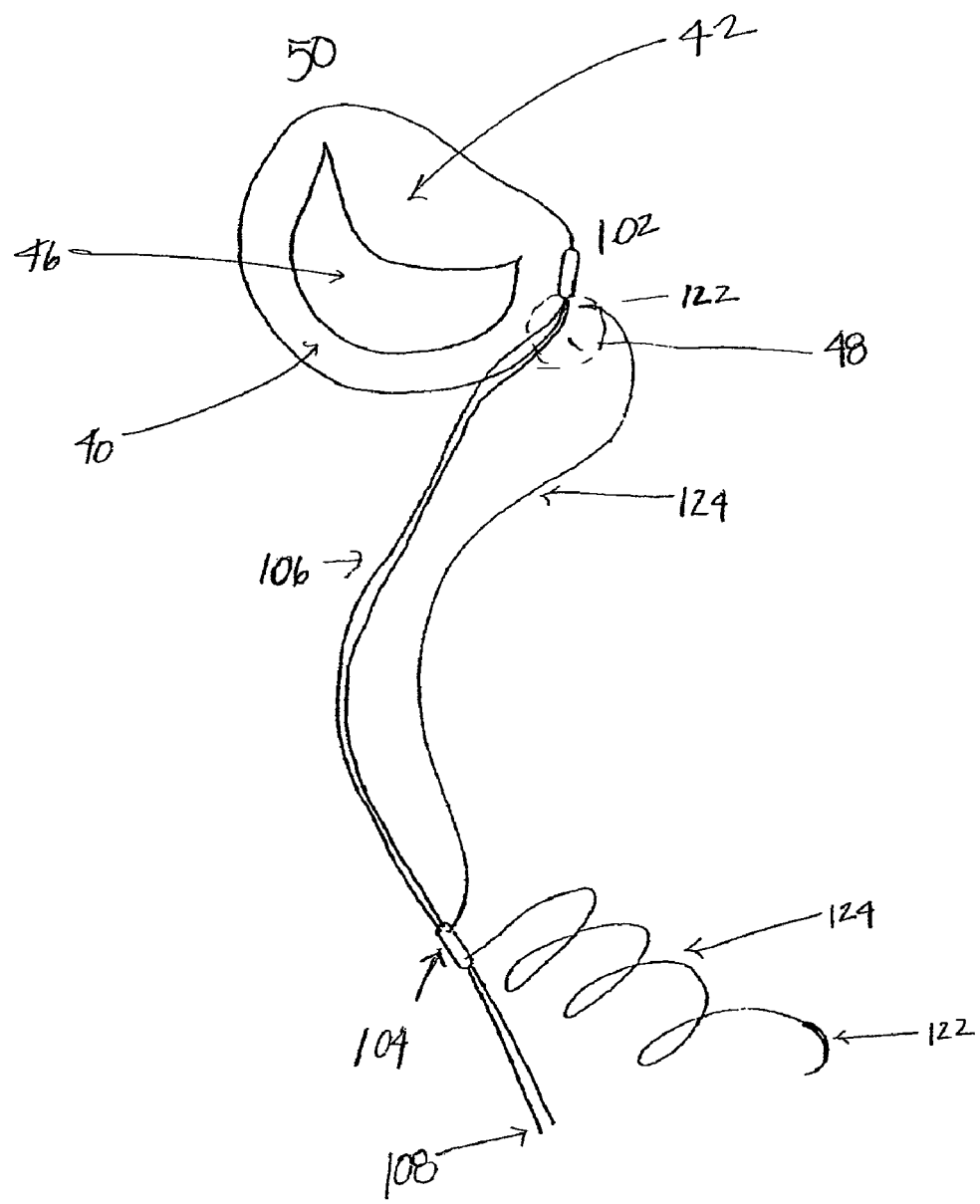

FIG. 1J depicts the method of implantation of the first intermediate suture support segment 104. First, the surgeon will guide a surgical needle 122 to the surgical site 48 and then will pass the surgical needle 122 through the surgical site 48 on the mitral valve annulus 50 about 2-4 mm away from the first surgical site 44. The surgical needle 122 and suture 124 will be passed through the mitral valve annulus 50 in a conventional surgical technique so as to make a horizontal mattress stitch.

Figure 1K:
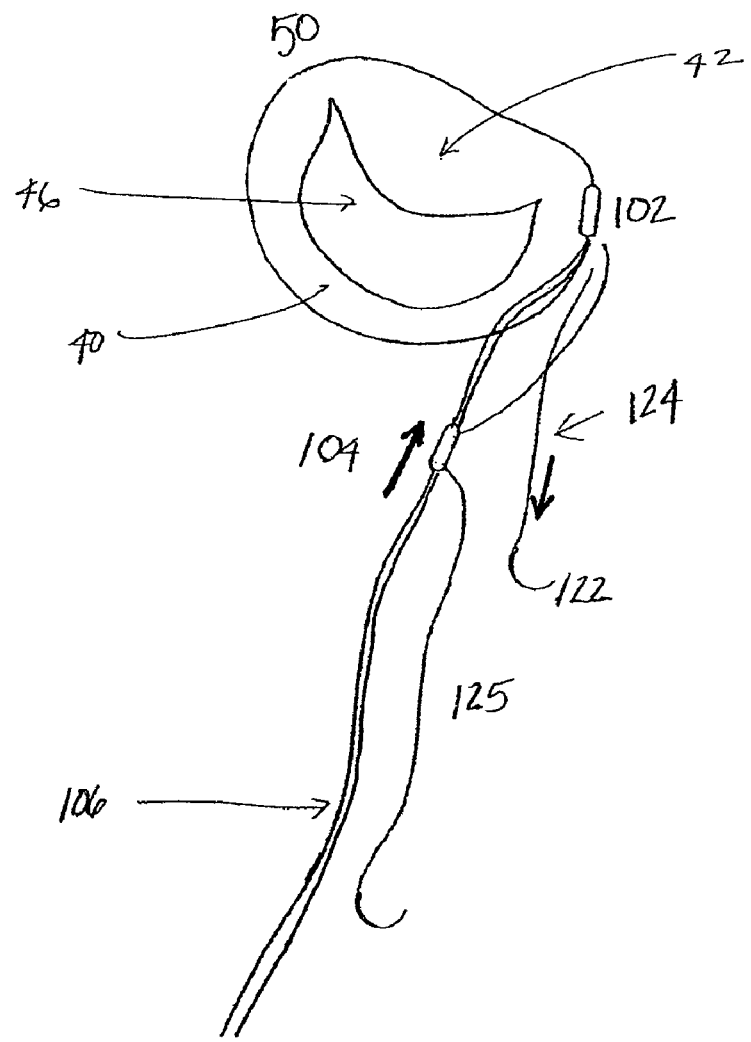

FIG. 1K shows how the intermediate suture support segment 104 is guided onto the mitral valve annulus 50. The surgeon will use the supportive drawstrings 106 which run through the channels 130 in the intermediate support segment 104 to guide the intermediate support segment down toward the mitral valve while pulling on the surgical needle 122 and the suture 124 to shuttle the intermediate suture support segment 104 next to the anchor suture support segment 102.

Figure 1L:
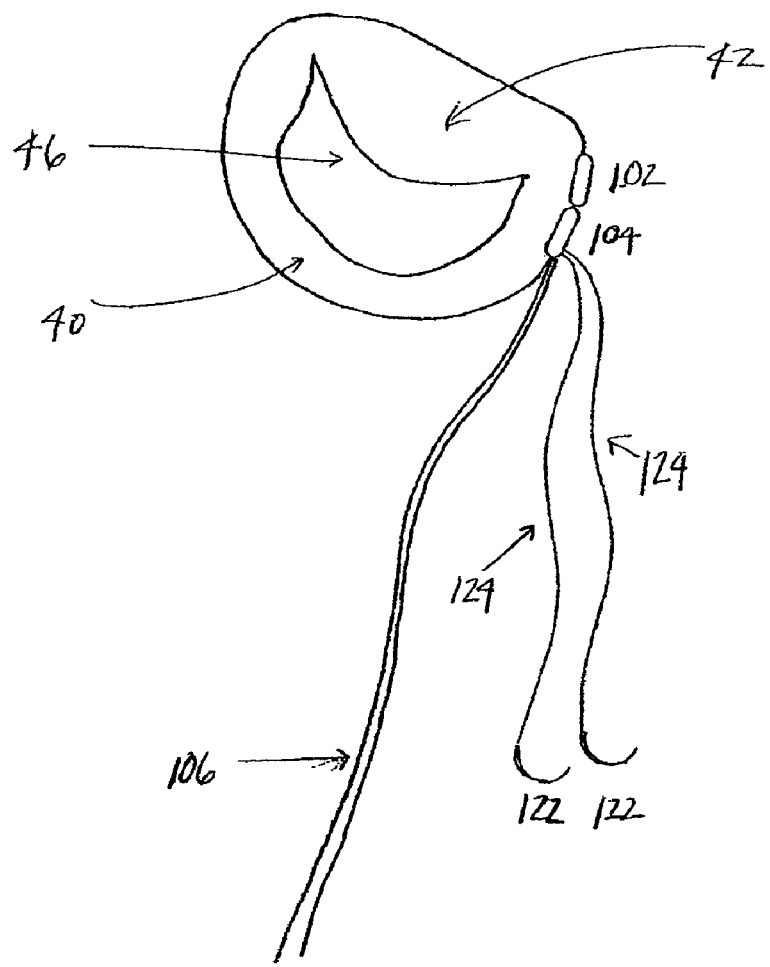
Figure 1M:
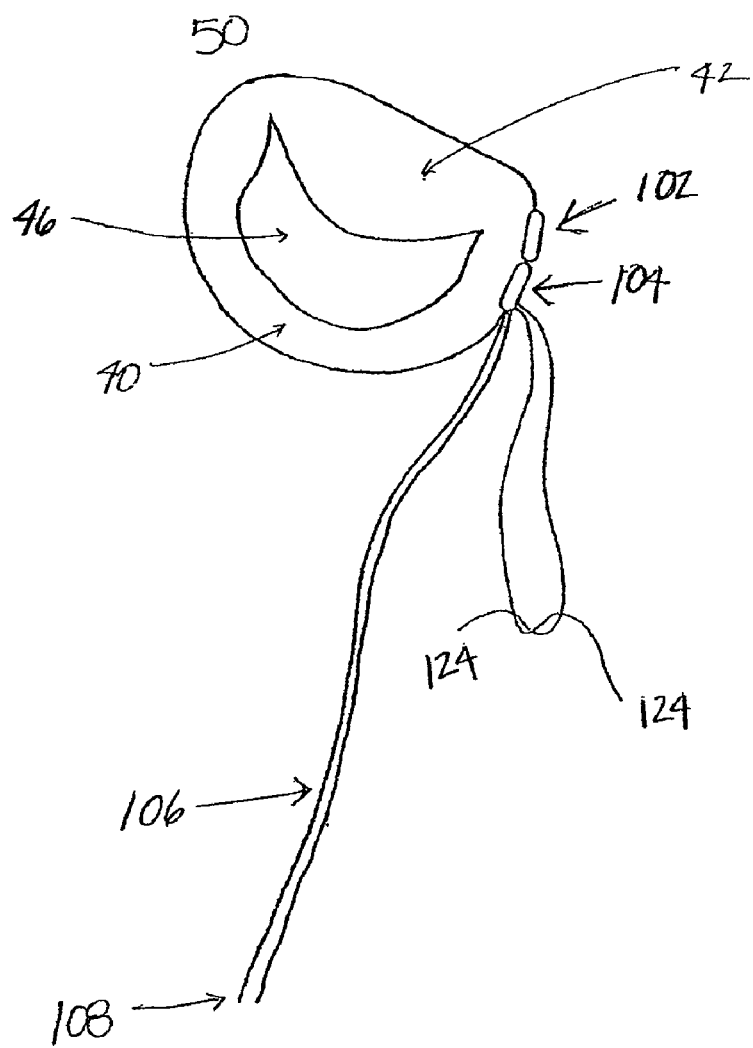

FIG. 1L depicts the first intermediate suture support segment 104 aligned with the mitral valve annulus 50 and adjacent to the anchor suture support segment 102. To secure the intermediate suture support segment 104 the surgeon will first cut off the surgical needles 122 from each of the sutures 124 (not shown). Next, as depicted in FIG. 1M the surgeon will tie the two free ends of the sutures 124 together with sufficient tension thereby securing the intermediate suture support segment 104 in place on the mitral valve annulus 50 next to the anchor suture support segment 102. After five or six knots have been made the free tails of the sutures 124 are cut by any suitable means (not shown).

Figure 1N:
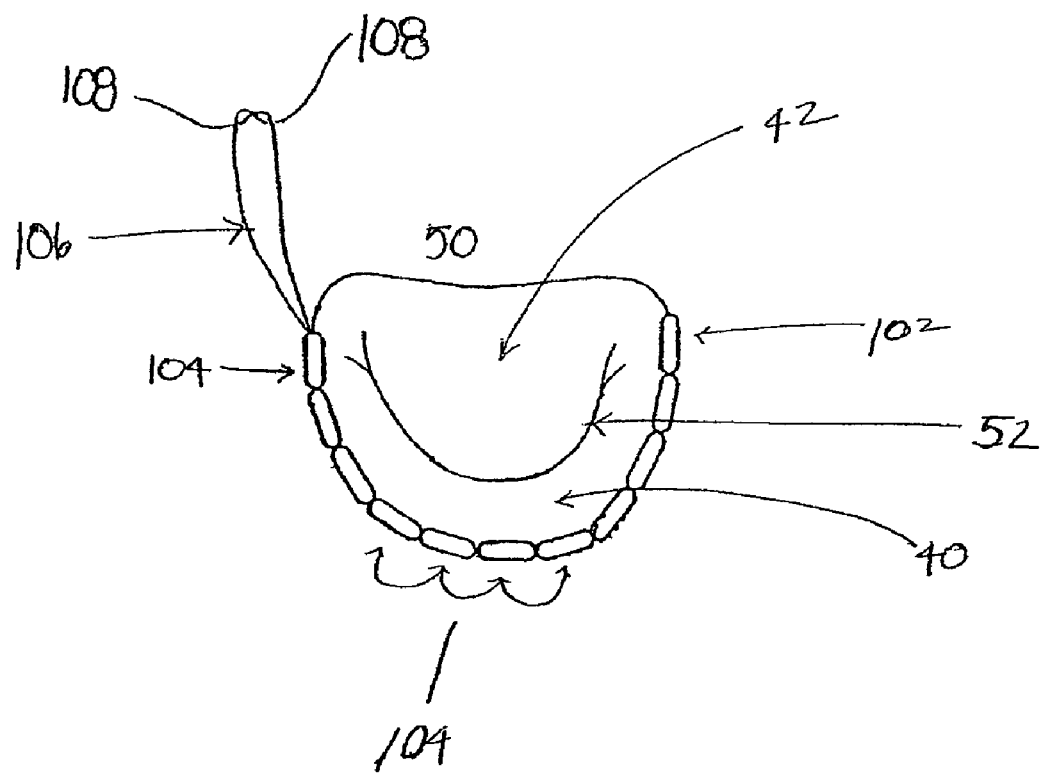

The above described steps shown in FIGS. 1J-1M are repeated until the desired circumference around the mitral valve annulus 50 is covered by intermediate suture support segments 104. The number of support segments placed into the mitral valve annulus 50 determines the overall reduction in the circumference of the annulus. FIG. 1N depicts the repaired mitral valve 52 surrounded by an anchor suture support segment 102 and intermediate suture support segments 104 that make up the flexible dual supportive drawstring annuloplasty system 100. When the desired circumference of the valve annulus has been covered the mitral valve is tested for competence by distending the left ventricle with isotonic solution infused through rubber-bulbed syringe. If needed the annuloplasty system 100 is further adjusted and the suture support segments 102 and 104 are further aligned by pulling the supportive drawstrings 106 that is found at the distal end of the last intermediate suture support segment 104. Since the support segments 102 and 104 are slidably coupled with the supportive drawstring 106 the annular tissue between adjacent suture support segments will plicate and the circumference of the valve annulus will reduce further. To complete the valve repair the free ends 108 of the supportive drawstring 106 are tied together at the distal end of the last intermediate suture support segment 104. After seven or eight knots are made the free ends 108 of the supportive drawstring 106 are cut at the point beyond the last intermediate suture support segment 104 by any suitable means.

FIG. 1O depicts an alternate embodiment of the dual-supportive drawstring annuloplasty system 100 which only partially surrounds the mitral valve annulus 50. The anchor suture support segment 102 is attached to the mitral valve annulus 50 using the process described in FIGS. 1F-1H. The intermediate suture support segments 104 are attached to the mitral valve annulus using the process described in FIGS. 1J-1M. The intermediate suture support segments 104 only partially surround the mitral valve annulus 50 and the annuloplasty system 100 is ended by tying the free ends 108 of the supportive drawstrings 106 around the distal end of the last intermediate suture support segment 104. As an alternate embodiment, this method of implantation can also be done with a single-supportive drawstring annuloplasty system 200, although it is not depicted.

Figure 1P:
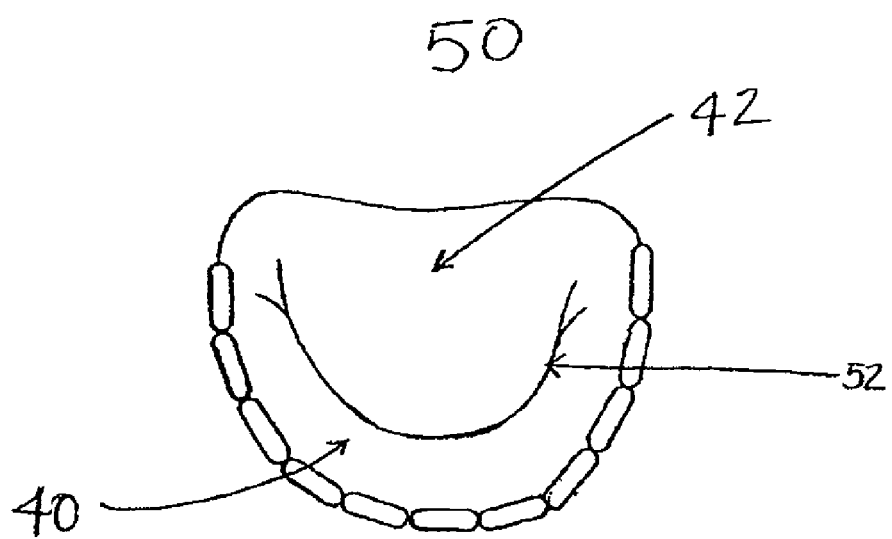

FIG. 1P depicts a repaired mitral valve annulus 52 and shows how a completed annuloplasty system 100 should look once implanted in the mitral valve annulus 50.

Figure 1Q:
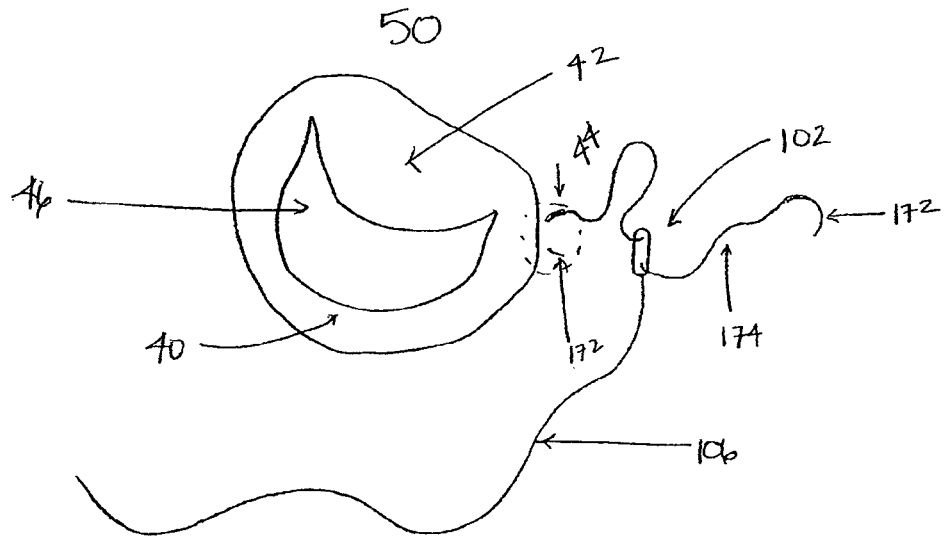

FIG. 1Q depicts that the anchor suture support segment 102 may be attached to the surgical site 44 using the surgical needle 172 to place the sutures 174 in a counter-clockwise fashion. This also applies to placement of the intermediate suture support segments 104 of the dual-supportive drawstring system 100 and this also applies to all segments (202, 204, and 210) of the single supportive drawstring system 200.

Figure 1R:
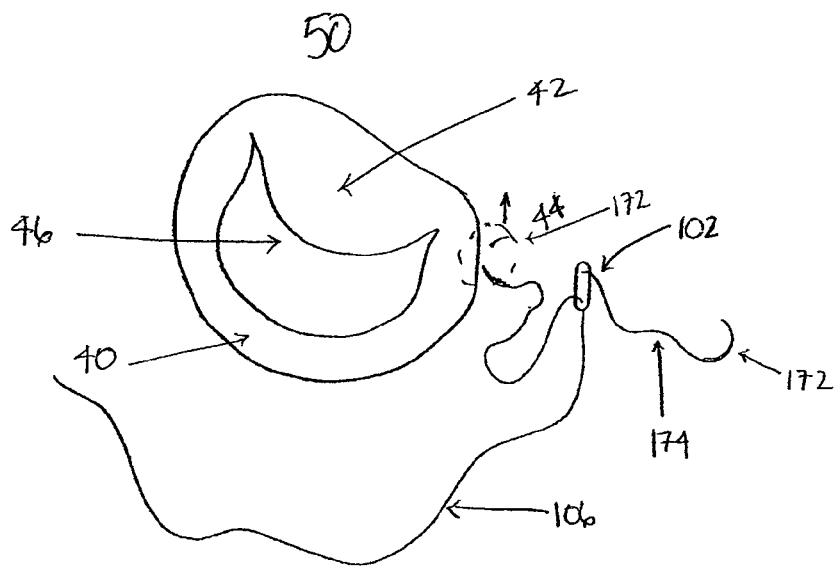
Figure 1R:
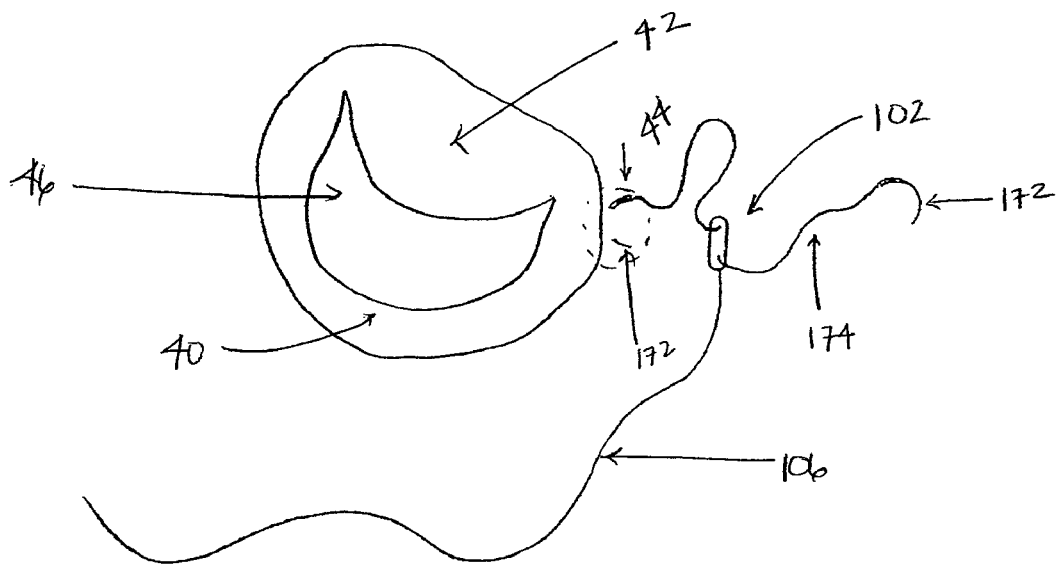
Figure 1S:
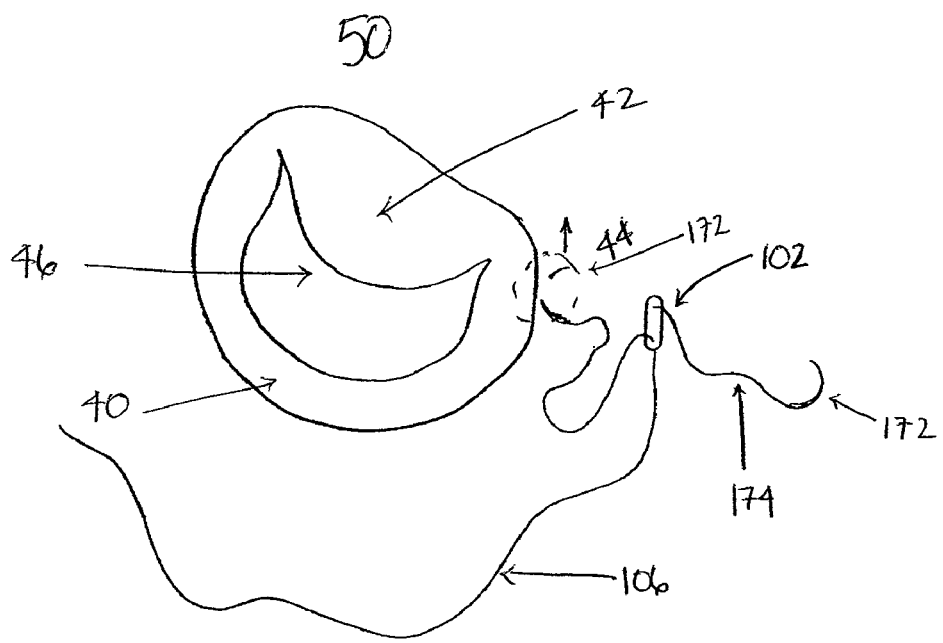

FIG. 1R depicts that the anchor suture support segment 102 may be attached to the surgical site 44 using the surgical needle 172 to place the sutures 174 in a clockwise fashion. This method also applies to placement of the intermediate suture support segments 104 of the dual-supportive drawstring system 100 and this also applies to all segments (202, 204, and 210) of the single supportive drawstring system 200.

A second exemplary embodiment of this invention (shown in FIGS. 2A-AC) also provides an annuloplasty system for repairing incompetent heart valves. This system includes: a substantially circular valve reinforcing device adapted to be surgically implanted around a heart valve annulus; anchoring means for attaching the substantially circular valve reinforcing device to the heart valve annulus, wherein attaching the substantially circular valve reinforcing device to the heart valve annulus reduces the circumference of the annulus by plicating annular tissue underneath the valve reinforcing device; and constricting means for reducing the circumference of the substantially circular valve reinforcing device, wherein reducing the circumference of the substantially circular valve reinforcing device further reduces the circumference of the annulus. The valve reinforcing device further includes: (i) a plurality of individual suture support segments, wherein the plurality of suture support segments further includes: a) at least one anchor segment, wherein the at least one anchor segment further includes a channel passing lengthwise therethrough; b) at least one terminal segment, wherein the at least one terminal segment further includes a channel passing lengthwise therethrough; and c) a plurality of intermediate segments disposed between the at least one anchor segment and the at least one terminal segment, wherein each intermediate segment further includes a channel passing lengthwise therethrough. The anchoring means further includes: (i) at least two sutures attached to the anchor segment, wherein at least one of the sutures includes a surgical needle attached thereto; (ii) at least two sutures attached to the intermediate segment, wherein at least one of the sutures includes a surgical needle attached thereto; and (iii) at least two sutures attached to the body portion of the terminal segment wherein at least one of the sutures includes a surgical needle attached thereto and a third suture attached to the end portion of the terminal segment for tying off the supportive drawstring following implantation. The constricting means for reducing the circumference of the substantially circular valve reinforcing device, wherein reducing the circumference of the valve reinforcing device further reduces the circumference of the heart valve annulus, and wherein the constricting means further includes: (i) a supportive drawstring, wherein one end of the drawstring is attached to one end of the anchor segment, and wherein the supportive drawstring passes through the channel in each intermediate segment and the channel in the terminal segment.

A method for surgically implanting this annuloplasty system includes (a) utilizing the anchoring means for securing the substantially circular valve reinforcing device to the heart valve annulus, wherein securing the substantially circular valve reinforcing device to the heart valve annulus reduces the circumference of the annulus by plicating annular tissue underneath the valve reinforcing device; and (b) utilizing the constricting means to reduce the circumference of the substantially circular valve reinforcing device if appropriate constriction has not been achieved, wherein reducing the circumference of the valve reinforcing device further reduces the circumference of the heart valve annulus by plicating the annular tissue between adjacent segments of the substantially circular valve reinforcing device. Utilizing the anchoring means further includes: (i) affixing the anchor segment to a dilated heart valve annulus by passing one of the surgical needles attached to the sutures through the heart valve annulus; (ii) pulling the suture and surgical needle which has passed through the heart valve annulus until the anchor segment is aligned with the heart valve annulus; (iii) securing the anchor segment to the heart valve annulus by tying the ends of the sutures together; (iv) using the supportive drawstring to guide the intermediate segment through a minimally-invasive tube or small incision to the position above the heart valve annulus adjacent to the anchor segment; (v) affixing the intermediate segment to the heart valve annulus by passing one of the surgical needles attached to the sutures through the heart valve annulus; (vi) pulling the surgical needle and suture which has passed through the heart valve annulus until the intermediate segment aligns with the heart valve annulus; (viii) securing the intermediate segment to the heart valve annulus by tying the ends of the sutures together; (viii) repeating steps (iv)-(vii) until the desired circumference around the heart valve annulus is covered by intermediate suture support segments; (ix) using the supportive drawstring to guide the terminal segment to the position above the heart valve annulus next to the last intermediate segment; (x) affixing the terminal segment to the heart valve annulus by passing one of the surgical needles attached to the sutures through the heart valve annulus; (xi) pulling the surgical needle and suture which has passed through the heart valve annulus until the terminal segment is aligned with the heart valve annulus; (xii) securing the terminal segment to the heart valve annulus by tying the ends of the sutures together; and (xiii) testing the repaired heart valve to verify that appropriate constriction has been achieved. Utilizing the constricting means further includes: (i) pulling the supportive drawstring to the desired tension to further decrease the circumference of the heart valve annulus; and (ii) tying the supportive drawstring that runs through the terminal segment to the third suture attached to the end portion of the terminal segment.

Figure 2G:
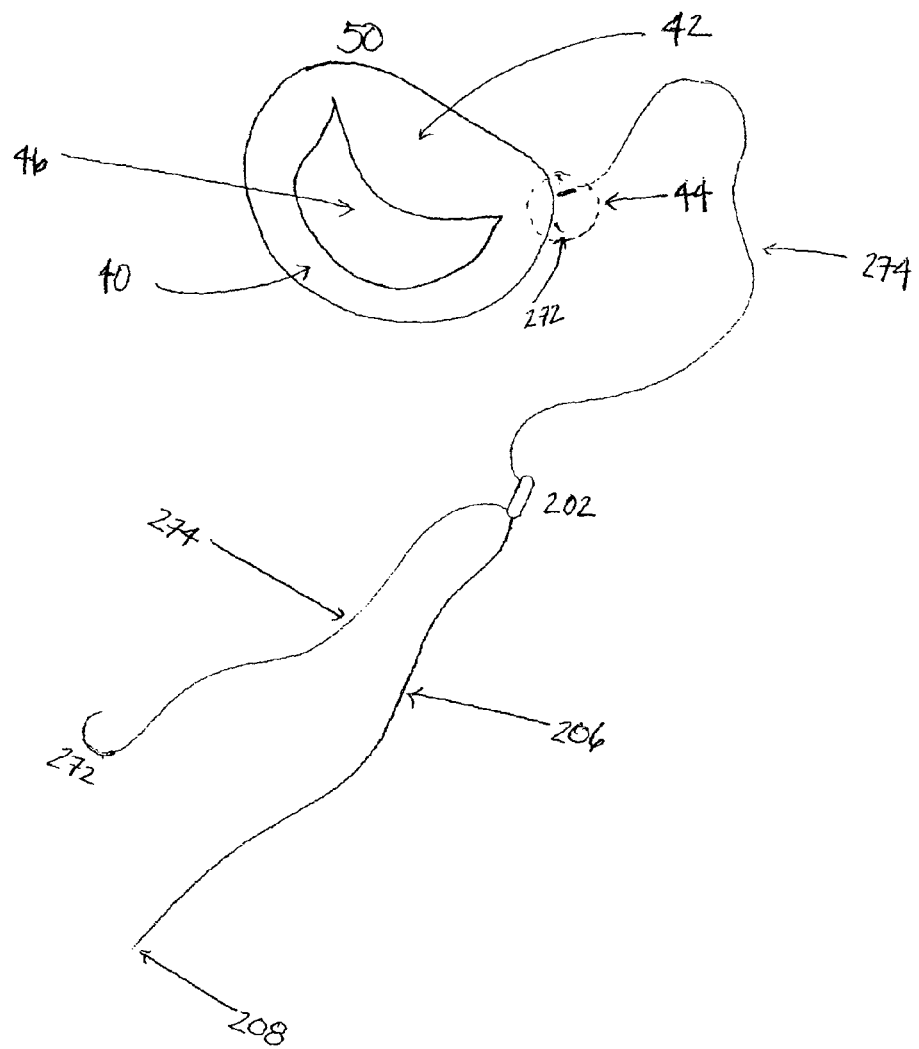
Figure 2H:
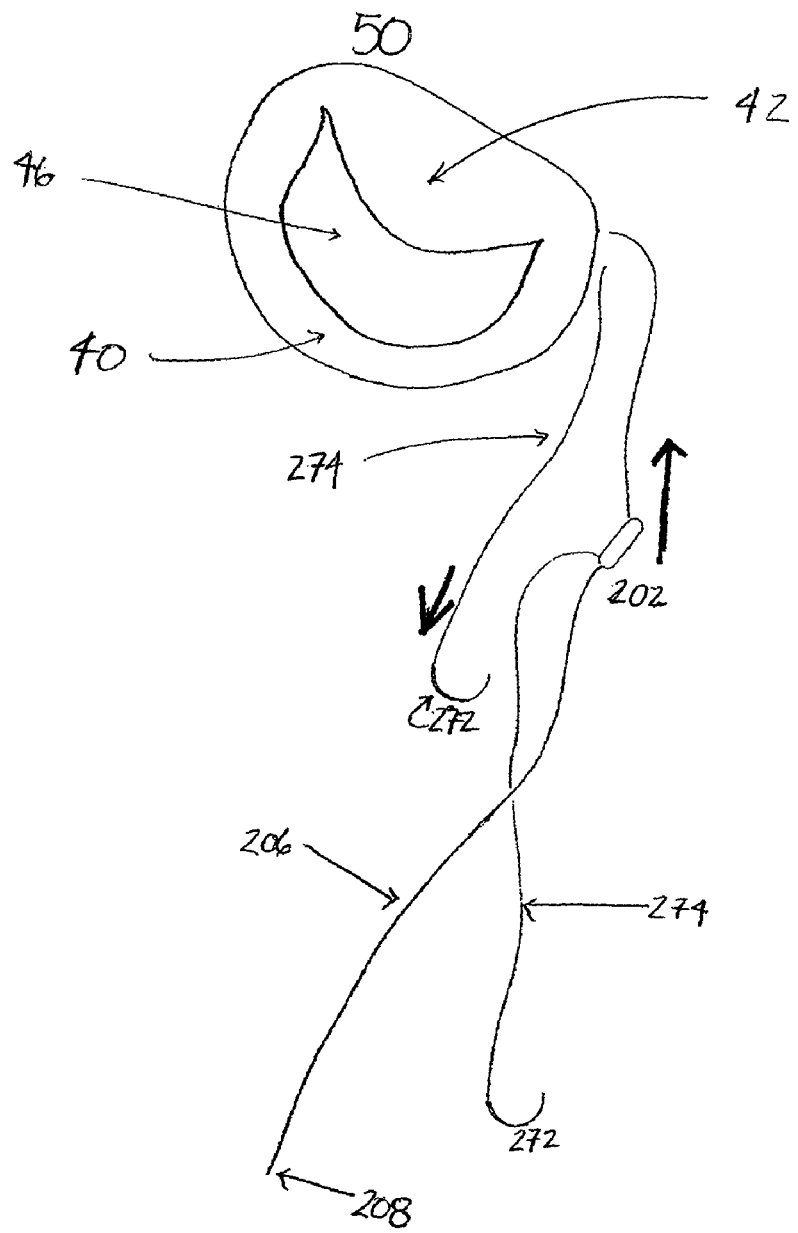
Figure 2I:
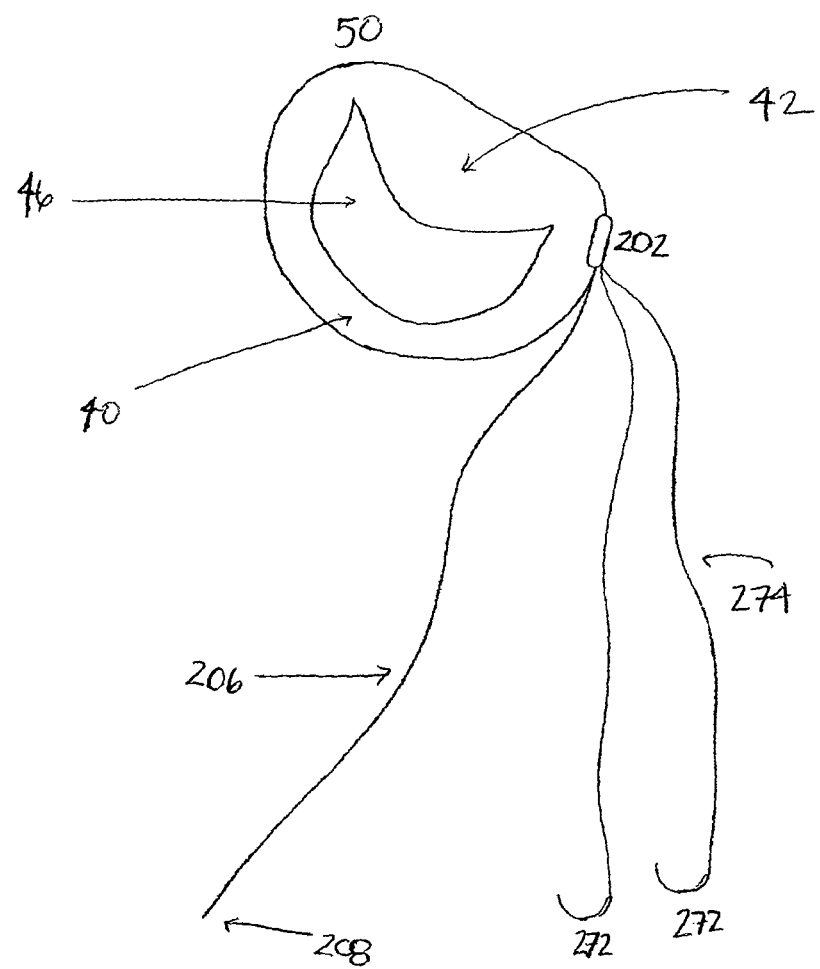
Figure 2J:
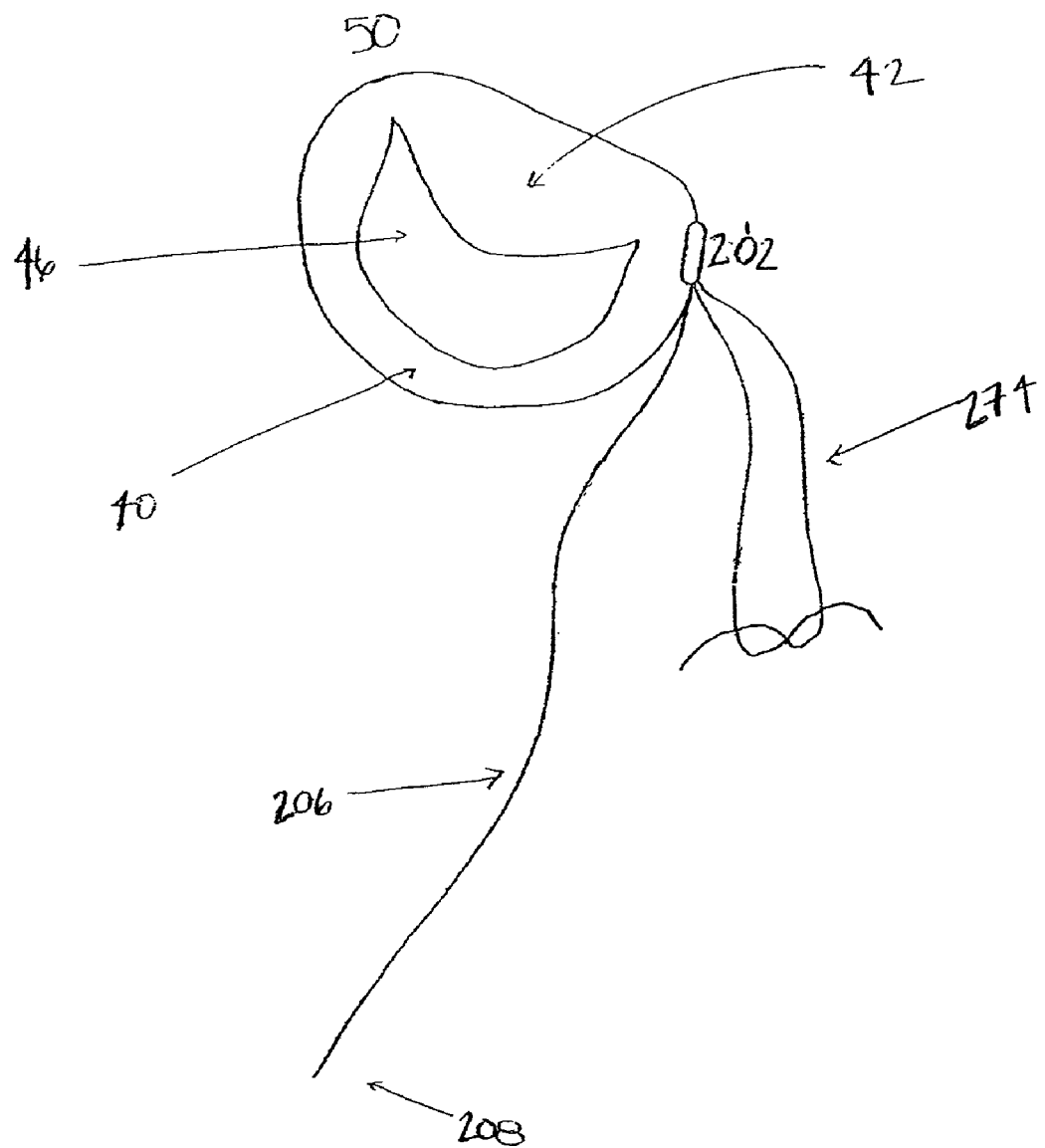
Figure 2K:
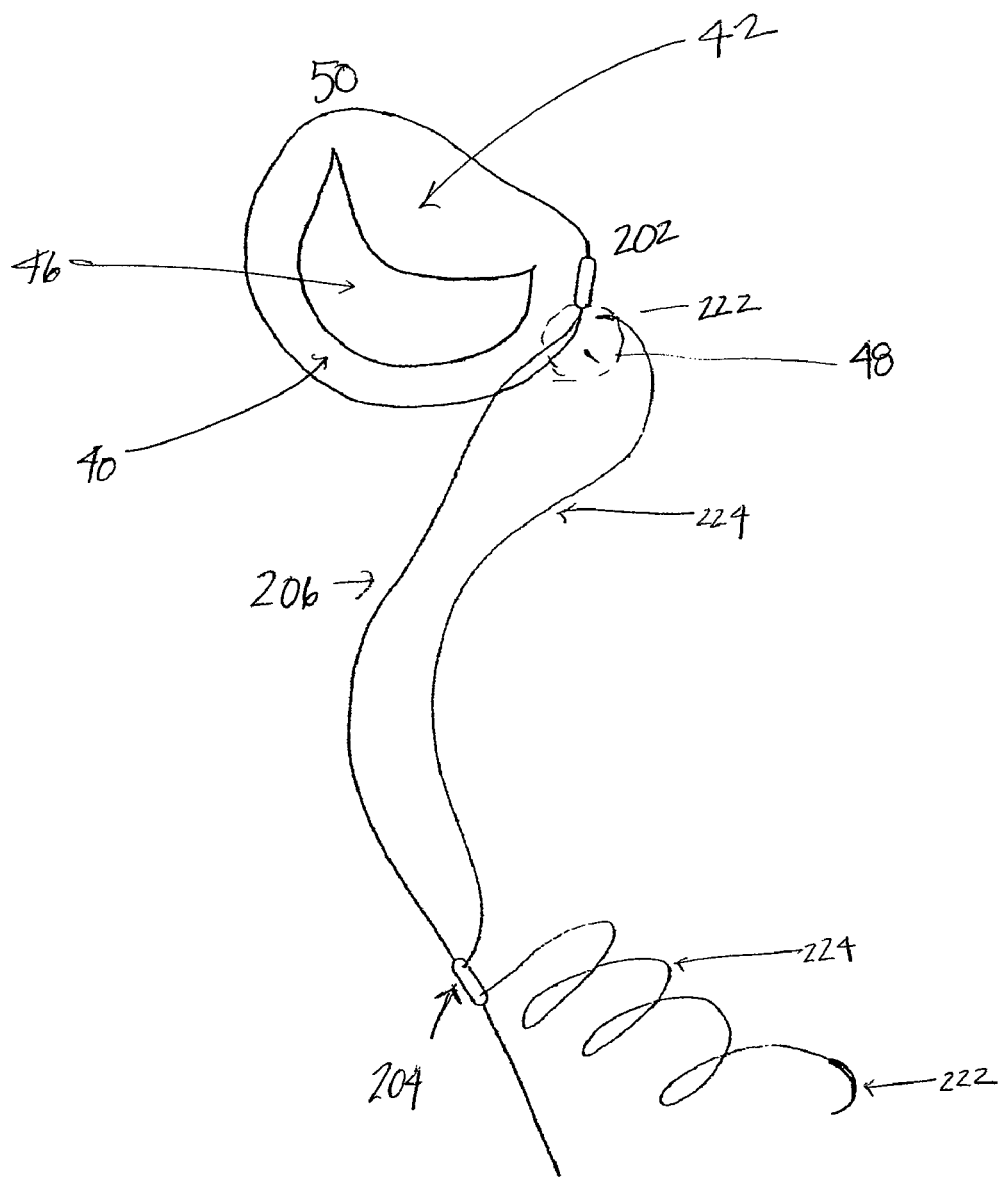
Figure 2L:
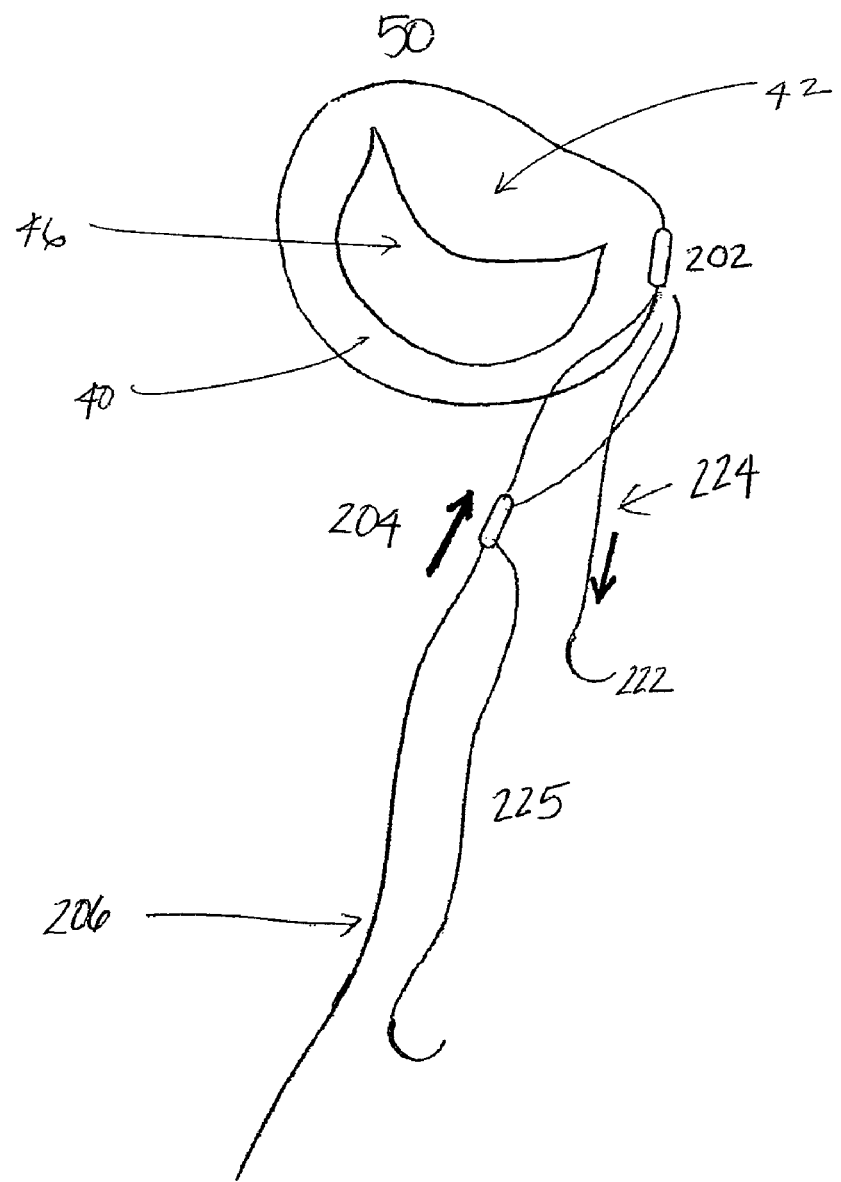
Figure 2M:
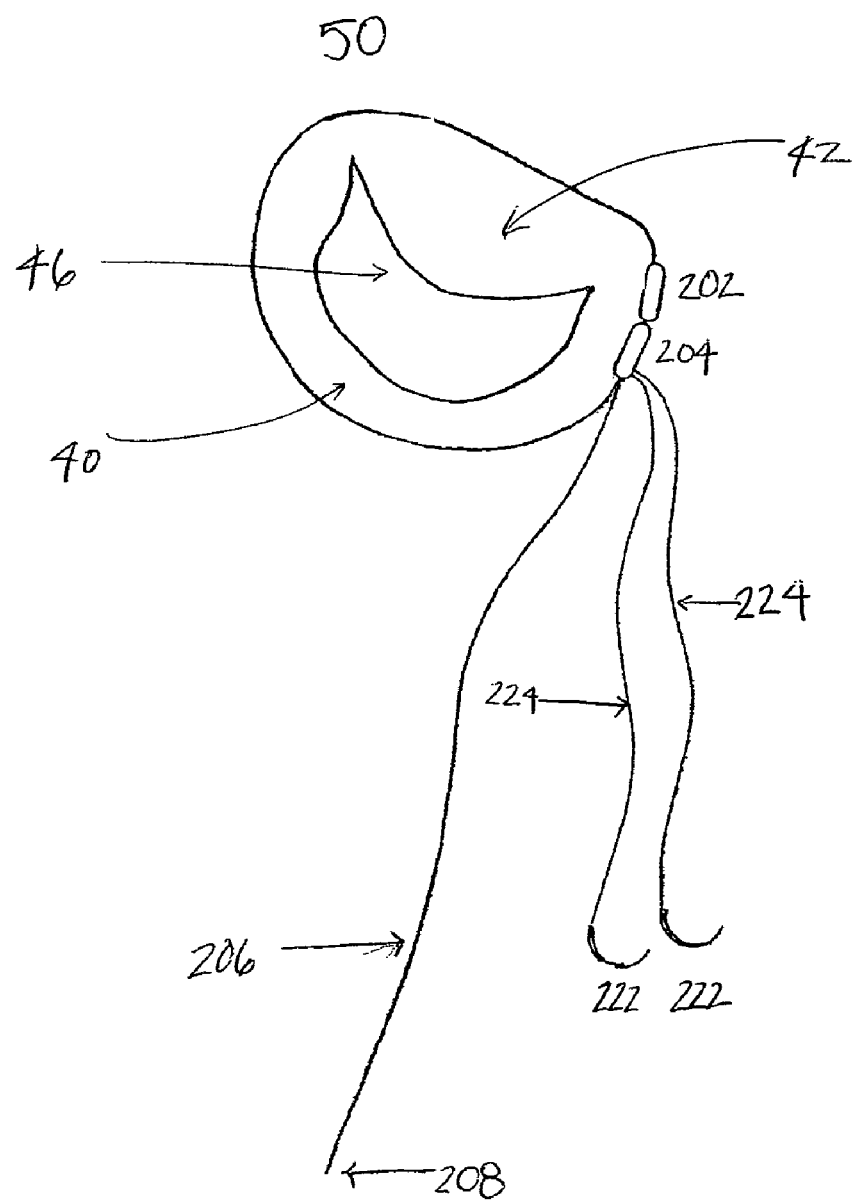
Figure 2N:
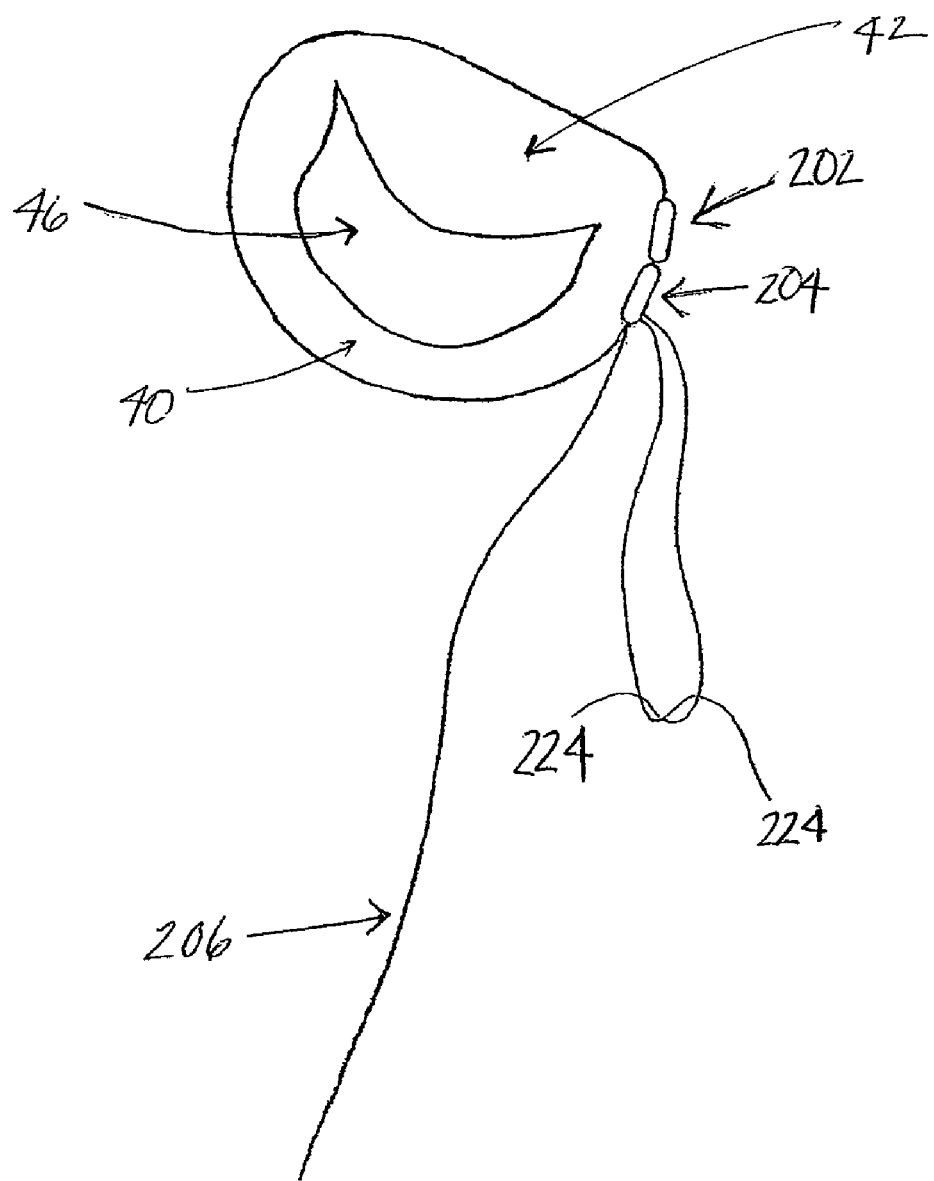
Figure 2P:
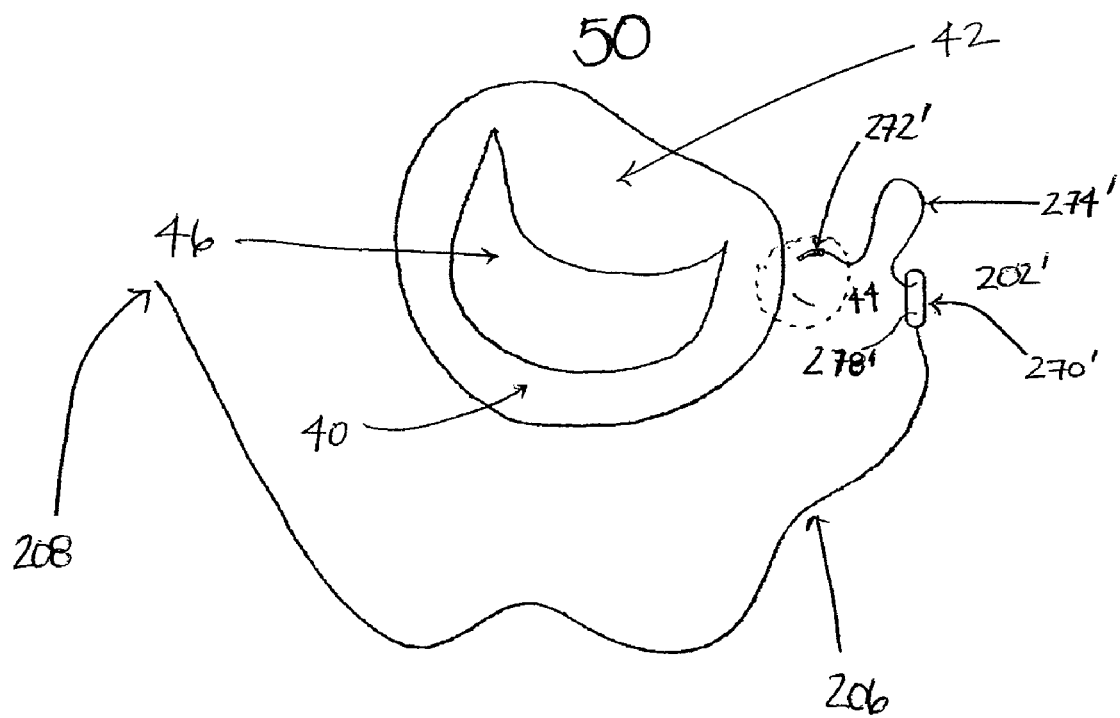
Figure 2Q:
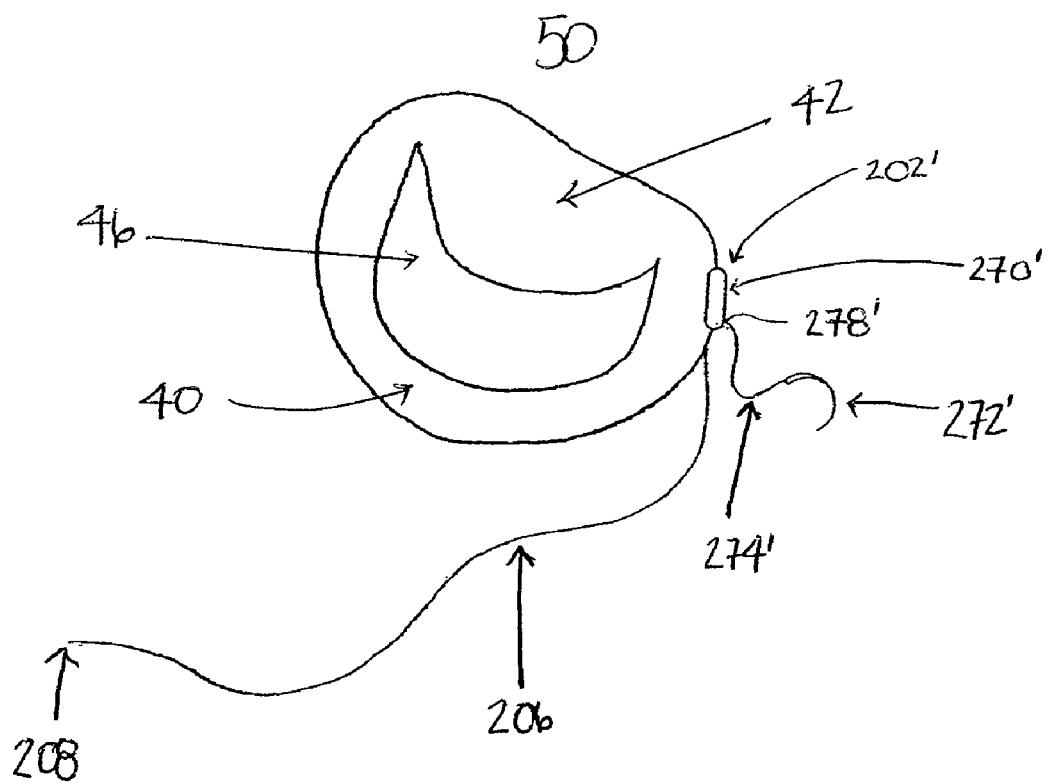
Figure 2R:
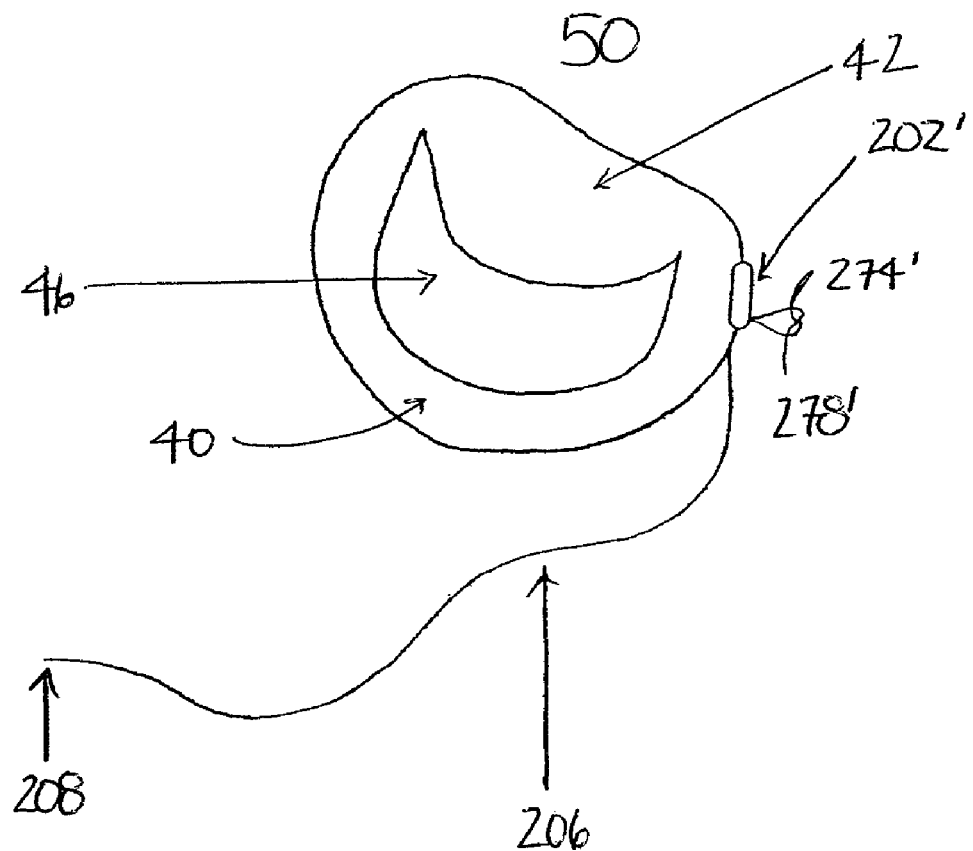
Figure 2S:
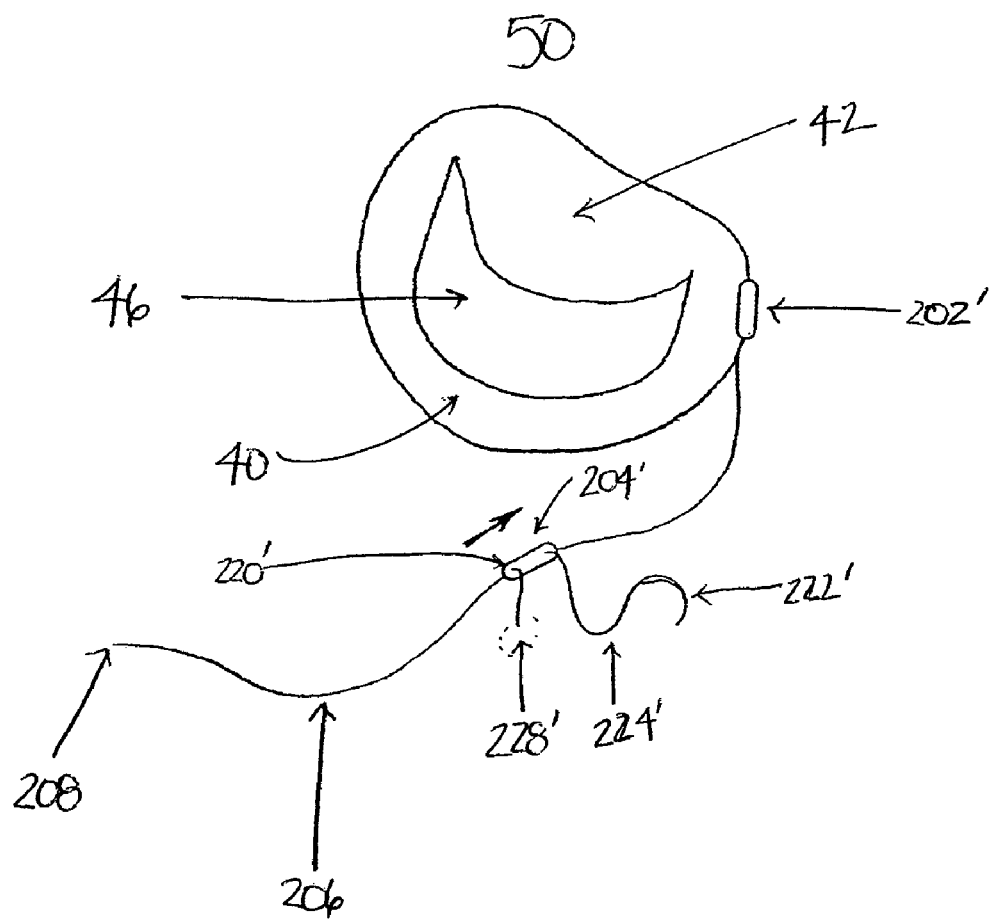
Figure 2T:
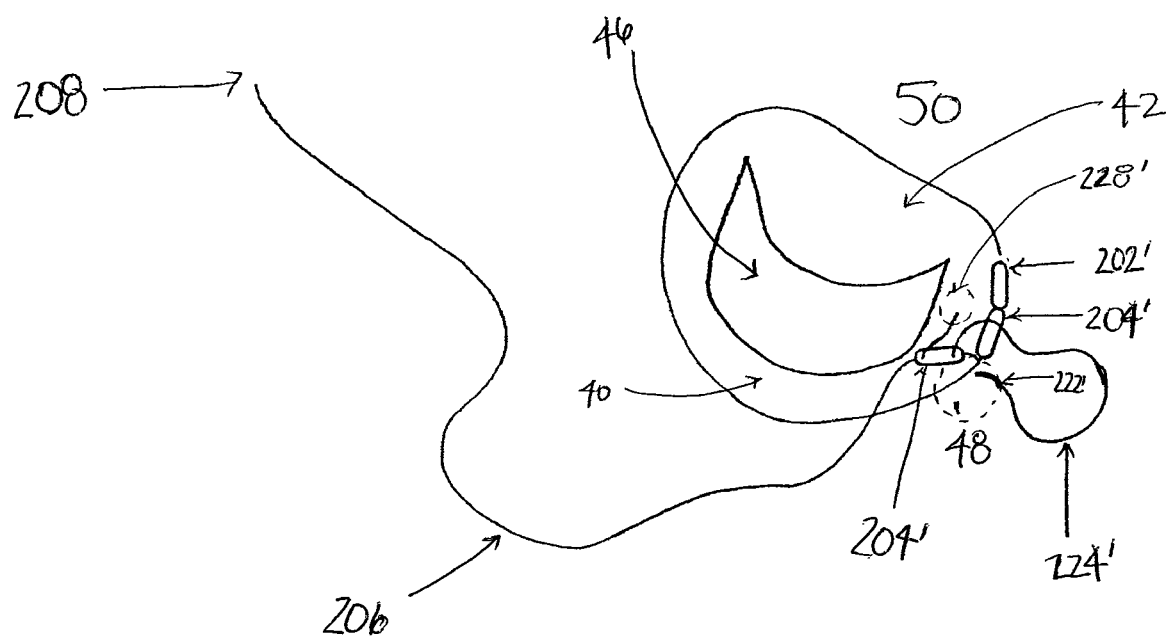
Figure 2U:
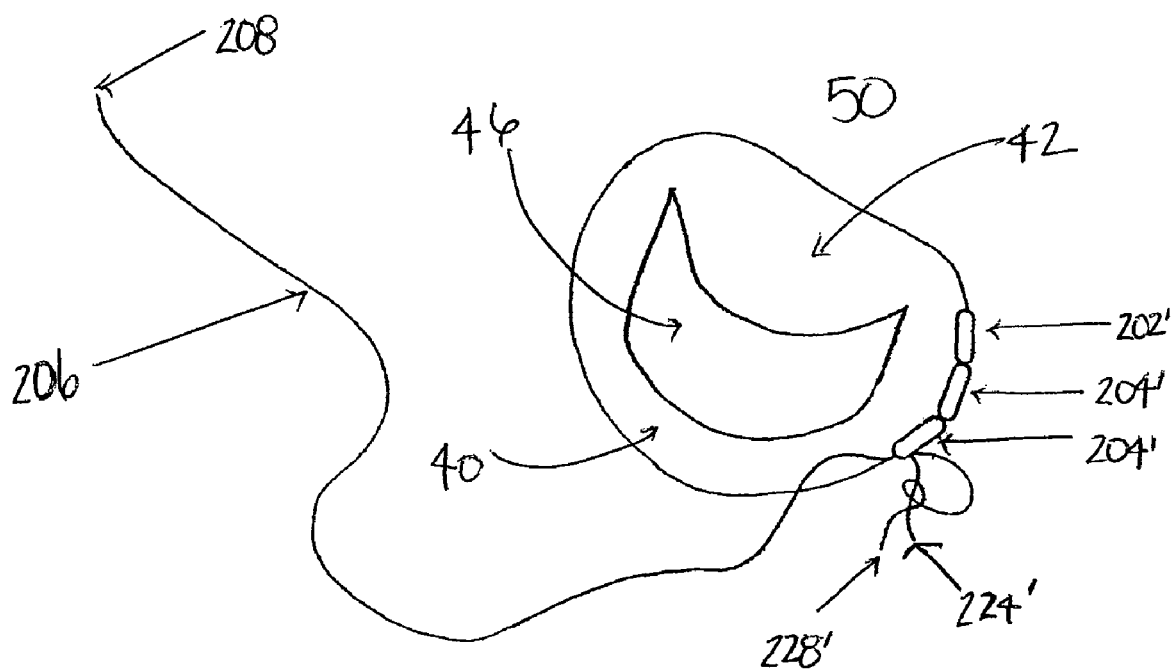
Figure 2V:
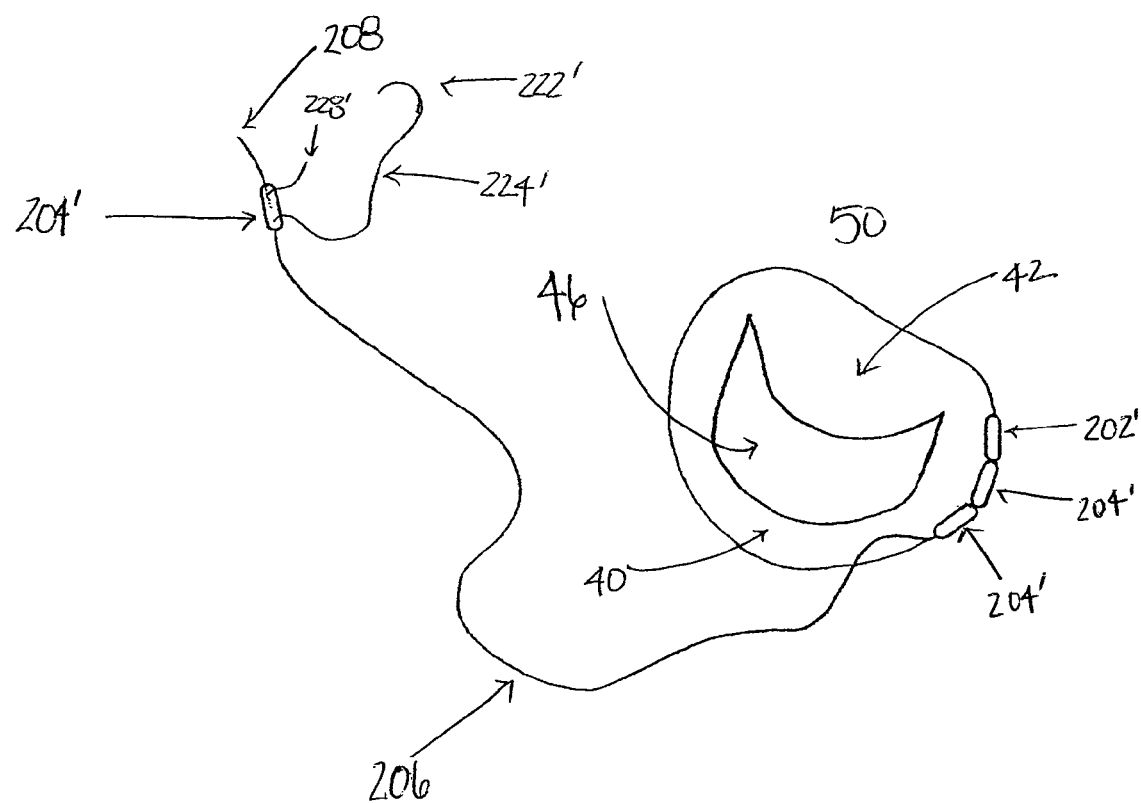
Figure 2W:
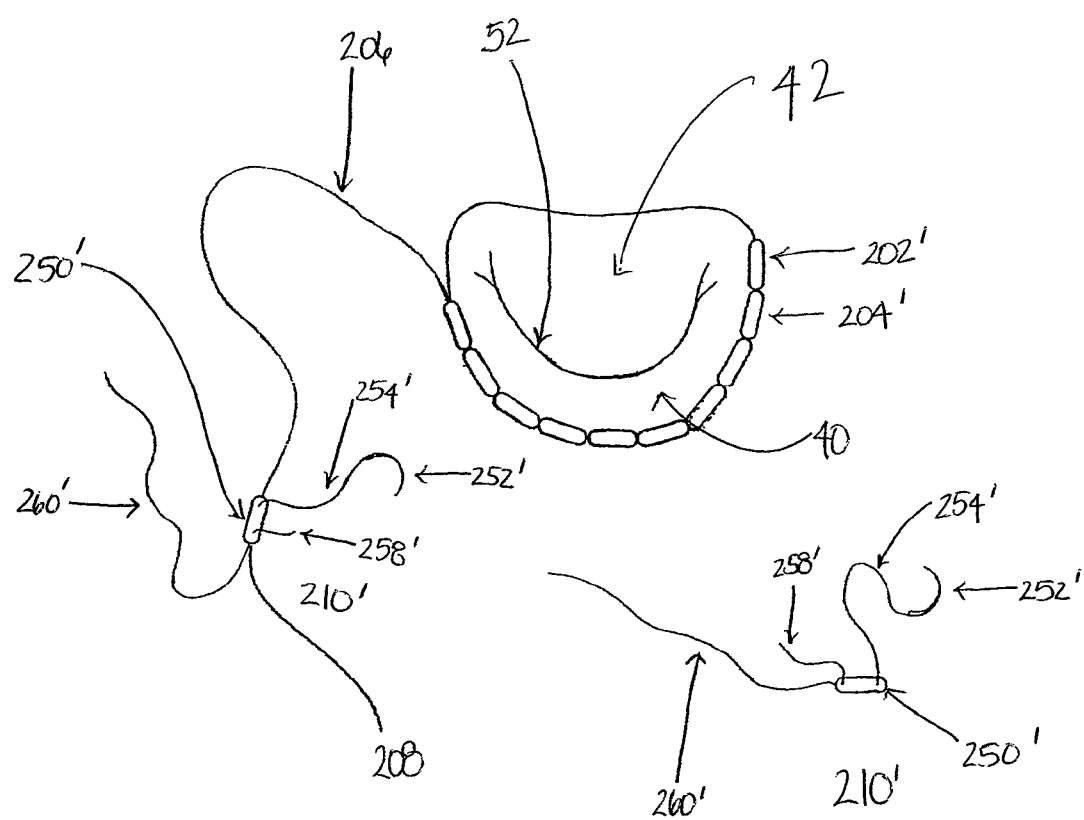
Figure 2X:
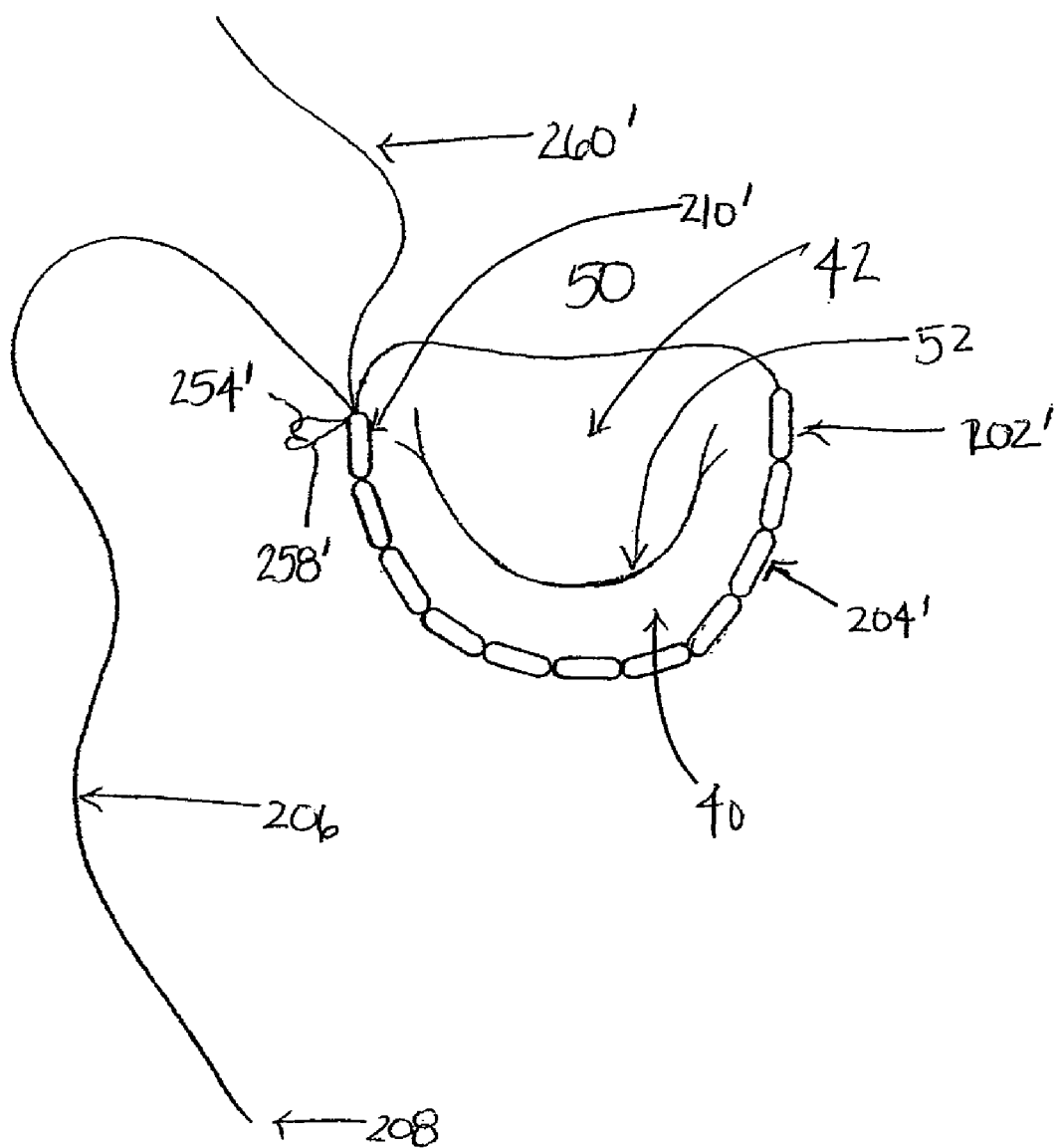
Figure 2Y:
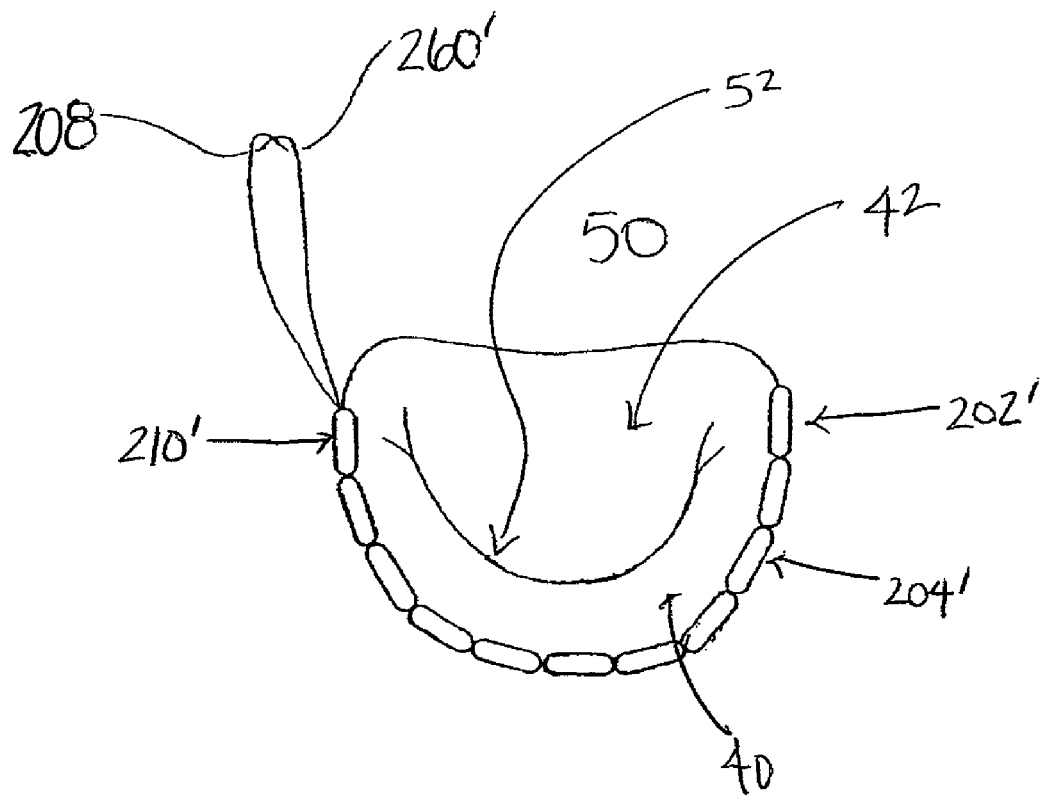
Figure 2A:
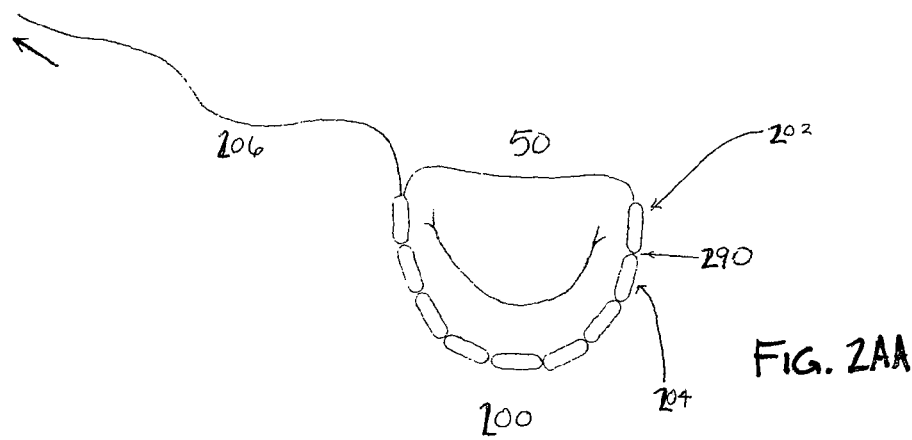
FIG. 2A is a top view of a second exemplary embodiment of the annuloplasty system of the present invention wherein the system includes a flexible single supportive drawstring.
Figure 2A:
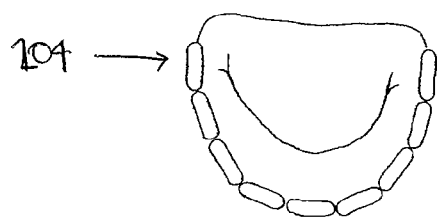
Figure 2A:
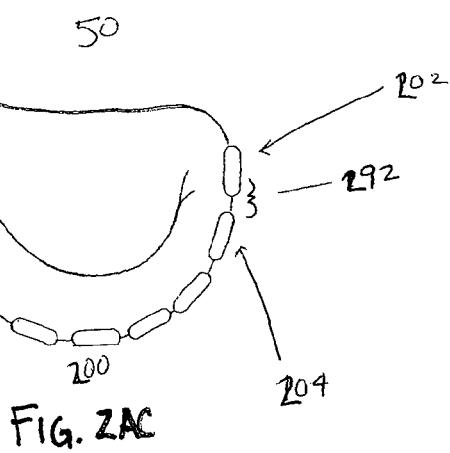

FIG. 2A illustrates a flexible single-supportive drawstring annuloplasty system 200 having an anchor suture support segment 202 with a supportive drawstring 206 attached, a plurality of intermediate suture support segments 204 threaded through the supportive drawstring 206 and a terminal suture support segment 210 threaded through the supportive drawstring 206. The supportive drawstring 206 has a free end 208 where the intermediate suture support segments 204 and terminal suture support segments 210 are added to the single-supportive drawstring annuloplasty system 200. The terminal suture support segment 210 has a free suture 260 which is tied with the free end 208 of the supportive drawstring 206 around the terminal segment 210 to complete the flexible single-supportive drawstring annuloplasty system 200.

FIGS. 2B-2F illustrate various views of the elements that comprise the single-supportive drawstring annuloplasty system 200. FIG. 2B depicts the detail of an anchor suture support segment 202. The anchor suture support segment 202 is made up of an anchor suture support segment body 270, at least one surgical needle 272, and at least one suture 274. The anchor suture support segment body 270 may be made from any material that is radio-opaque, preferably inert, non-corrosive, non-thormbogenic and bio-compatible with blood and tissue. By way of example, but not limitation, such material might be a barium sulfate impregnated acetal resin Delrin. The anchor suture support segment body 270 can be cylindrical, tubular, square, round, oval, elongated oval or combinations thereof shaped as necessary to achieve the desired configuration. The anchor suture support segment body 270 may have a textured blood-contacting surface or may be coated, in whole or in part, by a material designed to promote tissue in-growth and reduce thromboemblosim. By way of example, but not limitation, such material might be Dacron, polyester velour or some other suitable material. A preferred size of the intermediate suture support segment body 270 is 1 mm to 4 mm in length but more preferably 2 mm to 6 mm in length, with a circumference of 1 mm to 4 mm, although other sizes and dimensions are possible. Attached to the anchor suture support segment body 270 is at least one suture 274, but more preferably two sutures 274. The anchor suture support segment body 270 must be rigid or semi-rigid in the longitudinal direction, and must not be deformable, such that when the sutures 274 are tied against the anchor suture support segment body 270, the anchor suture support segment body does not buckle. The material for the suture 274 may be of any conventional type used in surgical procedures such as 2/0 braided suture, mono-filament suture, or polyfilament suture. The length of the suture 274 may range between 1 centimeter to 25 centimeters, and more preferably between 2 centimeters to 10 centimeters. The sutures 274 are attached to the anchor suture support segment body 270 in such a way as to create a dual-armed suture structure 276. Attached to the free ends of each suture 274 is a surgical needle 272. The surgical needle 272 is attached to the suture 274 by a conventional swedging process. The surgical needle 272 is a conventional curved surgical needle. Such surgical needles or suture needles are generally known and are normally made from a corrosion-resistant metal, preferably chrome-nickel steel.

As an alternate embodiment (not shown in the Figures) the anchor suture support segment 202' has an anchor suture support segment body 270' with attached suture 274'. The sutures 274' are attached to the side of the anchor suture support segment body 270'. Only one of the sutures 274' has attached to the free end a surgical needle 272' and the second suture 274' has a free end 278' without a surgical needle 272'.

FIG. 2F shows a cross-sectional view of an anchor suture support segment 202 specifically the anchor suture support segment body 270 with a single channel 280 and the cross sectional view of an intermediate suture support segment 204 specifically the intermediate suture support segment body 220. One end of the supportive drawstring 206 is attached in the channel 280 of the anchor suture support segment body 270. The supportive drawstring 206 runs through the channel 280 of the anchor suture support segment 202. The supportive drawstring 206 may be comprised of suture material, Teflon strip, a band, a filament, a wire or a strap. A space 232 will be present between the anchor suture support segment 202 and the intermediate suture support segment 204 when the annuloplasty system 200 is implanted into the heart valve annulus which will allow for flexibility between the individual segments. The supportive drawstring 206 is threaded through the single channel 230 running the length of the intermediate suture support segment 204.

FIG. 2C depicts the detail of an intermediate suture support segment 204. The intermediate suture support segment 204 is made up of an intermediate suture support segment body 220, at least one surgical needle 222, and at least one suture 224.

The intermediate suture support segment body 220 may be made from any material that is radio-opaque, preferably inert, non-corrosive, non-thormbogenic and bio-compatible with blood and tissue. By way of example, but not limitation, such material might be a barium sulfate impregnated acetal resin Delrin. The intermediate suture support segment body 220 can be cylindrical, tubular, square, round, oval, elongated oval or combinations thereof shaped as necessary to achieve the desired configuration. The intermediate suture support segment body 220 may have a textured blood-contacting surface or may be coated, in whole or in part, by a material designed to promote tissue in-growth and reduce thromboemblosim. By way of example, but not limitation, such material might be Dacron, polyester velour or some other suitable material. A preferred size of the intermediate suture support segment body 220 is 1 mm to 4 mm in length but more preferably 2 mm to 6 mm in length, with a circumference of 1 mm to 4 mm, although other sizes and dimensions are possible. Attached to the intermediate suture support segment body 220 is at least one suture 224, but more preferably two sutures 224. The intermediate suture support segment body 220 must be rigid or semi-rigid in the longitudinal direction, and must not be deformable, such that when the sutures 224 are tied against the intermediate suture support segment body 220, the intermediate suture support segment body does not buckle. The material for the suture 224 may be of any conventional type used in surgical procedures such as 2/0 braided suture, mono-filament suture, or polyfilament suture. The length of the suture 224 may range between 1 centimeter to 25 centimeters, and more preferably between 2 centimeters to 10 centimeters. The sutures 224 are attached to the side of the intermediate suture support segment body 220 in such a way as to create a dual-armed suture structure 226. Attached to the free ends of each suture 224 is a surgical needle 222. The surgical needle 222 is attached to the suture 224 by a conventional swedging process. The surgical needle 222 is a conventional curved surgical needle. Such surgical needles or suture needles are generally known and are normally made from a corrosion-resistant metal, preferably chrome-nickel steel.

As an alternative embodiment as shown in FIG. 2C the intermediate suture support segment 204' has an intermediate suture support segment body 220' with attached suture 224'. The sutures 224' are attached to the side of the intermediate suture support segment body 220' Only one of the sutures 224' has attached to the free end a surgical needle 222' and the second suture 224' has a free end 228' without a surgical needle 222'.

FIG. 2E is a cross sectional view of an intermediate suture support segment 204. It shows the single channel 230 that runs the length of the intermediate suture support segment body 220.

FIG. 2D depicts the detail of a terminal suture support segment 210. The terminal suture support segment 210 is made up of a terminal suture support segment body 250, at least one surgical needle 252, and at least one suture 254. The terminal suture support segment body 250 may be made from any material that is radio-opaque, preferably inert, non-corrosive, non-thormbogenic and bio-compatible with blood and tissue. By way of example, but not limitation, such material might be a barium sulfate impregnated acetal resin Delrin. The terminal suture support segment body 250 can be a cylindrical, a tubular, a square, a round, an oval, an elongated oval or the like shaped as necessary to achieve the desired configuration. The terminal suture support segment body 250 may have a textured blood-contacting surface or may be coated, in whole or in part, by a material designed to promote tissue in-growth and reduce thromboemblosim. By way of example, but not limitation, such material might be Dacron, polyester velour or some other suitable material. A preferred size of the terminal suture support segment body 250 is 1 mm to 4 mm in length but more preferably 2 mm to 6 mm in length, with a circumference of 1 mm to 4 mm, although other sizes and dimensions are possible. Attached to the terminal suture support segment body 250 is at least one suture 254, but more preferably two sutures 254. The terminal suture support segment body 250 must be rigid or semi-rigid in the longitudinal direction, and must not be deformable, such that when the sutures 254 are tied against the terminal suture support segment body 250, the terminal suture support segment body does not buckle. The material for the suture 254 may be of any conventional type used in surgical procedures such as 2/0 braided suture, mono-filament suture, or polyfilament suture. The length of the suture 254 may range between 1 centimeter to 25 centimeters, and more preferably between 2 centimeters to 10 centimeters. The sutures 254 are attached to the side of the terminal suture support segment body 250 in such a way as to create a dual-armed suture structure 256. Attached to the free ends of each suture 254 is a surgical needle 252. The surgical needle 252 is attached to the suture 254 by a conventional swedging process. The surgical needle 252 is a conventional curved surgical needle. Such surgical needles or suture needles are generally known and are normally made from a corrosion-resistant metal, preferably chrome-nickel steel. The terminal suture support segment 210 has a free suture 260 attached to the end portion of the terminal suture segment body 250. The material for the third suture 260 may be of any conventional type used in surgical procedures such as 2/0 braided suture, mono-filament suture, or polyfilament suture. The length of the third suture 260 may range between 1 centimeter to 25 centimeters, and more preferably between 2 centimeters to 10 centimeters. The third suture 260 on the terminal suture support segment 210 has a free end without a surgical needle 252.

FIG. 2D also shows an alternative embodiment where the terminal suture support segment 210' has an terminal suture support segment body 250' with attached suture 254'. The sutures 254' are attached to the side of the terminal suture support segment body 250'. Only one of the sutures 254' has attached to the free end a surgical needle 252' and the second suture 254' has a free end 258' without a surgical needle 252'.

FIGS. 2G-2O depict a method of implantation of the single-supportive drawstring annuloplasty system 200 described in FIGS. 2A-2F. The surgical methods used to implant the annuloplasty system 200 may be conventional open heart surgery techniques or minimally invasive heart surgery techniques. FIGS. 2G-2O provide an illustration of the superior view of the dilated mitral valve of a human heart. The mitral valve includes a fibrous annulus 50 and anterior and posterior leaflets 42, 40. In a healthy heart the leaflets close tightly during systole and do not allow any of the blood to flow backwards through the mitral valve into the left atrium. However, one consequence of a number of cardiac diseases is that mitral valve annulus 50 becomes dilated so that the anterior and posterior leaflets 42 and 40 cannot close tightly during systole, thereby creating gap 46 between the anterior and posterior leaflets 42 and 40. As a result, mitral valve regurgitation occurs, resulting in some of the blood flowing backwards through the incompletely closed mitral valve leaflets into the left atrium. FIG. 2G depicts the first step of the method of implantation in which the surgical needle 272 and suture 274 will be passed through the mitral valve annulus 50 in a conventional surgical technique so as to make a horizontal mattress stitch. As shown in FIG. 2G the anchor suture support segment 202 has attached to the distal end a supportive drawstring 206 that has a free end 208.

FIG. 2H shows the next step in the method of implantation. The surgeon will continue to pull the surgical needle 272 and suture material 274, which has passed through surgical site 44, away from the mitral valve annulus 50 which will bring the anchor suture support segment 202 flush with the mitral valve annulus 50.

FIG. 2I depicts the anchor suture support segment 202 aligned with the mitral valve annulus 50. To secure the anchor suture support segment 202 the surgeon will first cut off the surgical needles 272 from each of the sutures 274 (not shown). Next, as depicted in FIG. 2J the surgeon will tie the two free ends of the sutures 274 together with sufficient tension thereby securing the anchor suture support segment 202 in place on the mitral valve annulus 50. After five or six knots have been made the free tails of the sutures 274 are cut by any suitable means (not shown). The suture 274 traverses a longer distance along the mitral valve annulus 50 than the distance between two suture attachments in the side of the anchor suture support segment body 270. Sutures 274, when tightened and tied, create an imbrication in the mitral valve annulus 50 underneath the segment thereby reducing the circumference of the annulus by an amount equal to the difference between the length each suture travels in the tissue of the heart annulus and the distance between the suture attachments in the support segment (not shown).

FIG. 2K depicts the implantation of the intermediate suture support segment 204. The surgeon will guide a surgical needle 222 to the surgical site 48 and then will pass the surgical needle 222 through the surgical site 48 on the mitral valve annulus 50 about 2-4 mm away from the proximal end of the anchor support segment 202. The surgical needle 222 and suture 224 will be passed through the mitral valve annulus 50 in a conventional surgical technique so as to make a horizontal mattress stitch.

FIG. 2L shows how the intermediate suture support segment 204 is guided onto the mitral valve annulus 50. The surgeon will use the supportive drawstring 206 which runs through the channel in the intermediate support segment 204 to guide the intermediate support segment down toward the mitral valve while pulling on the surgical needle 222 and the suture 224 to shuttle the intermediate suture support segment 204 next to the anchor suture support segment 202.

FIG. 2M depicts the intermediate suture support segment 204 aligned with the mitral valve annulus 50 and adjacent to the anchor suture support segment 202. To secure the intermediate suture support segment 204 the surgeon will first cut off the surgical needles 222 from each of the sutures 224 (not shown). Next, as depicted in FIG. 2N the surgeon will tie the two free ends of the sutures 224 together with sufficient tension thereby securing the intermediate suture support segment 204 in place on the mitral valve annulus 50 next to the anchor suture support segment 202. After five or six knots have been made the free tails of the sutures 224 are cut by any suitable means (not shown).

The above described steps shown in FIGS. 2K-2N are repeated until the desired circumference around the mitral valve annulus 50 is covered by intermediate suture support segments 204. To complete the annuloplasty system 200 the terminal suture support segment 210 is added to the supportive drawstring 206 like described in FIGS. 2K-2N and is secured into place as shown in FIG. 2M. The number of support segments placed into annulus determines the overall reduction in the circumference of the annulus. FIG. 2O depicts a repaired mitral valve 52 surrounded by an anchor suture support segment 202, intermediate suture support segments 204, and a terminal suture support segment 210 that make up the flexible single supportive drawstring annuloplasty system 200. When the entire circumference of the valve annulus has been covered the mitral valve is tested for competence by distending the left ventricle with isotonic solution infused through rubber-bulbed syringe. If needed the annuloplasty system 200 is further adjusted and the suture support segments 202, 204, and 210 are further aligned by pulling the supportive drawstring 206 that is found at the distal end of the terminal suture support segment 210. Since the support segments 202, 204 and 210 are slidably coupled with the supportive drawstring 206 the annular tissue between adjacent suture support segments will plicate and the circumference of the valve annulus will reduce further. To complete the valve repair the free end 208 of the supportive drawstring 206 is tied together with the free suture 260 attached to the end of the terminal suture support segment 210. After seven or eight knots are made with the free end 208 of the supportive drawstring 206 and the free suture 260 of the terminal suture support segment 210 are cut at the point beyond the terminal suture support segment 210 by any suitable means.

FIGS. 2P-2Z depict an alternate embodiment of using short sutures for robotic mitral valve repair procedures using either the single-supportive drawstring annuloplasty system 200 or double-supportive drawstring annuloplasty system 100, both systems are described above. The system as depicted in FIGS. 2P-2Z uses the single supportive drawstring annuloplasty system 200, but it may also be used with the double-supportive drawstring annuloplasty system 100. As shown in FIG. 2P, the anchor suture support segment body 270' has attached to the side two short sutures 274' and a single or double supportive drawstring 206 with a free end 208. Attached to one of the sutures 274' is a surgical needle 272', whereas the other suture 274' has a free end 278'. FIG. 2P shows the implantation procedure of the anchor suture support segment 202'. Using robotic surgery instruments (not shown) the surgeon will deliver the anchor suture support segment 202' to the surgical site 44 and will held it approximately 5 cm above the mitral valve annulus 50. Using robotic surgery instruments (not shown) the surgical needle 272' and suture 274' will be passed through the mitral valve annulus 50 at the surgical site 44 so as to make a horizontal mattress stitch.

FIG. 2Q shows the anchor suture support segment 202' where the anchor suture support segment body 270' is aligned with the mitral valve annulus 50. The anchor suture support segment 202' is put into place by pulling on the surgical needle 272' and suture 274' using robotic instruments to make the anchor suture support segment body 270' flush with the mitral valve annulus 50. Once the anchor suture support segment body 270' is in the proper place the surgical needle 272' will be cut off of the suture 274' (not shown).

FIG. 2R shows how the anchor suture support segment is anchored to the mitral valve annulus 50. The free end 278' of the anchor suture support segment 202' is tied together with the suture 274' that had the surgical needle 272' removed. These two ends are tied together against the rigid or semi-rigid body of the anchor suture support segment 270'. Five to seven knots are made with the ends to hold the anchor sutures support segment 202' in place.

FIG. 2S shows how the first intermediate suture support segment 204' is delivered into position above the mitral valve from outside of the chest cavity by sliding the intermediate suture support segment 204' down over the supportive drawstring 206 using surgical knot pusher tool (not shown). There are two sutures 224' attached to the sides of the intermediate sutures support segment body 270'. Attached to one end of one sutures 224' is a surgical needle 222' the other suture 224' has a free end 228', without a surgical needle 222'.

FIG. 2T shows the implantation of the second intermediate suture support segment 202' into the mitral valve annulus 50, using robotic assisted surgery. The second support segment is delivered into position over the mitral valve annulus 50 by sliding the intermediate suture support segment 204' down over the supportive drawstring 206' and then the intermediate suture support segment 204' is held above the mitral valve annulus 50. The surgical needle 222' is passed through the mitral valve annulus 50 at the surgical site 48 using robotic surgical instruments so as to make a horizontal mattress stitch. The intermediate suture support segment 204' will be guided into place by pulling on the surgical needle 222' and suture 224' to make the second intermediate suture support segment body 220' flush with the mitral valve annulus 50 (not shown). Once the intermediate suture support segment body 220' is in the desired location the surgical needle 222' will be cut off of the suture 224' (not shown).

FIG. 2U shows how the second intermediate suture support segment 204' is secured to the mitral valve annulus 50 by robotic-assisted knot tying. The short suture 224' which had the surgical needle 222' removed is tied together with the free end 228' of the short suture 224'. The free end 228' and the sutures 224' are knotted together five to seven times against the intermediate suture support segment body 220' to secure the intermediate suture support segment 204' to the mitral valve annulus 50.

FIG. 2V depicts the addition of another intermediate suture support segment 204' to the mitral valve annulus 50. The supportive drawstring 206 is used as a guide to deliver the intermediate sutures support segment 204' into position above the mitral valve annulus 50 from outside of the chest cavity through a small incision or port (not shown). These steps are repeated until the desired circumference is covered around the mitral valve annulus 50.

FIG. 2W depicts the implantation of the terminal suture support segment 210'. First, the terminal suture support segment 210' is added by threading the free end 208 of the supportive drawstring 206 through the channel that runs through the body of the terminal suture support segment 250'. The terminal suture support segment body 250' has two surgical sutures 254' attached to the terminal suture support segment body 250'. One of the surgical sutures 254' has a surgical needle 252' attached to the end and the other surgical suture 254' has a free end 258'. Also attached to the terminal suture support segment body 250' is a free terminal suture 260'.

FIG. 2X shows how the terminal suture support segment 210' is secured to the mitral valve annulus 50 after the surgical needle 252' and the surgical suture 254' have been passed through the mitral valve annulus 50. The surgical suture 254' which had the surgical needle 252' removed is tied together with the free end 258' of the second surgical suture to secure the terminal suture support segment 210' to the mitral valve annulus 50. After five or six knots have been made the free tails of the sutures are cut by any suitable means (not shown). The mitral valve is tested for competence by distending the left ventricle with isotonic solution infused through rubber-bulbed syringe.

FIG. 2Y shows how the repair with the annuloplasty system 200' is completed. The free suture 260' attached to the terminal suture support segment body 250' is tied together with the free end 208 of the single supportive drawstring 206 against the terminal suture support segment body 250'. The free end of the suture 260' and the free end 208 of the supportive drawstring 206 are knotted together seven to eight times, and then the excess free tails are cut at a point beyond the terminal suture support segment 210' by any suitable means.

FIG. 2Z shows the suture support segments in place in the mitral valve annulus 50 whose circumference is thereby reduced after the implantation of the annuloplasty system 200' according to the present invention.

FIGS. 2AA-2AC depict using the single supportive drawstring annuloplasty system 200 (as shown) or the dual-supportive drawstring annuloplasty system 100 (not shown) in infants and growing children, where the supportive drawstring 206 will either be made from biodegradable material or will be removed after implantation onto the mitral valve annulus 50. The method of implantation of the annuloplasty system 200 in children and adolescents is similar to that described previously in FIGS. 2G-2O. As shown in FIG. 2AB when the entire circumference of the mitral valve annulus 50 has been sutured the mitral valve is tested for competence by distending the left ventricle with isotonic solution infused through rubber-bulbed syringe. The repair is completed by tightening the free ends of the biodegradable supportive drawstrings 206 over the last support segment 204. After seven or eight knots have been made the free end of the supportive drawstring 206 are cut by any suitable means. After mitral valve repair surgery the absorbable supportive drawstring 206 is eventually resorbed by the patient. The absence of the supportive drawstring 206 allows normal annular growth 292 between the suture support segments, 202 and 204 as the child grows, shown in FIG. 2AC. The biodegradable supportive drawstrings degrade at a rate that allows substantially complete healing of the patient's annular structure. The resulting time period to complete resorption may be on the order of 4 to 6 months to the order of 1 to 2 years.

In accordance with a further aspect of the present invention, as shown in FIG. 2AA, the surgeon removes the supportive drawstring 206 once the annuloplasty system 200 has been implanted in children or adolescents. When the entire circumference of the mitral valve annulus 50 has been sutured the mitral valve is tested for competence. The repair is completed by cutting the supportive drawstring 290 between the anchor suture support segment 202 and the first intermediate support segments 204 and then gently pulling on the free ends of the supportive drawstring 206 to withdraw the supportive drawstring 206 from the annuloplasty system 200, as shown in FIG. 2AB. The absence of the supportive drawstrings allows normal annular growth 292 between the suture support segments as the child grows, as shown in FIG. 2AC.

Alternatively, the surgeon can implant desirable number of free intermediate support segments (not shown) without supportive drawstrings and the anchor support segment until the entire circumference or at list a portion of the mitral valve annulus has been covered. The absence of the supportive drawstrings allows normal annular growth 292 between the suture support segments as the child grows, as shown in FIG. 2AC.

FIG. 5 depicts another exemplary embodiment of the annuloplasty system for minimally invasive or robotic valve repair procedures. This system is an alternate embodiment of the single-supportive drawstring annuloplasty system 200 or double-supportive drawstring annuloplasty system 100 described previously. As depicted the system has a single supportive drawstring but it can be used with a double supportive drawstring. The annuloplasty system 500 partially shown in FIG. 5A uses an anchor suture support segment 502 with an attached single supportive drawstring 506 that has a free end 508. The anchor suture support segment 502 shown in FIG. 5A has an anchor suture support segment body 570 with an attached suture 574 that may or may not have a surgical needle 572 (as shown it does not have an attached surgical needle 572) attached. The unique aspect of the embodiment is that the second suture 575 with attached surgical needle 572 is stored inside the anchor suture support segment body 570. The stored portion of the suture 575 is drawn out of the storage area so that the anchor sutures support segment 502 can be attached.

FIG. 5B shows an intermediate suture support segment 504 of the annuloplasty system 500. The intermediate suture support segment 504 is made up of an intermediate suture support segment body 520. Attached to the intermediate suture support segment body 520 is a suture 524 which may or may not have an attached surgical needle 522 (as shown no surgical needle 522 is attached). The second suture 525 has an attached surgical needle 522. This second suture 525 is stored within the intermediate suture support segment body 570. The stored portion of the suture 525 is drawn out of the storage area so that the anchor sutures support segment 502 can be attached.

Figure 6:
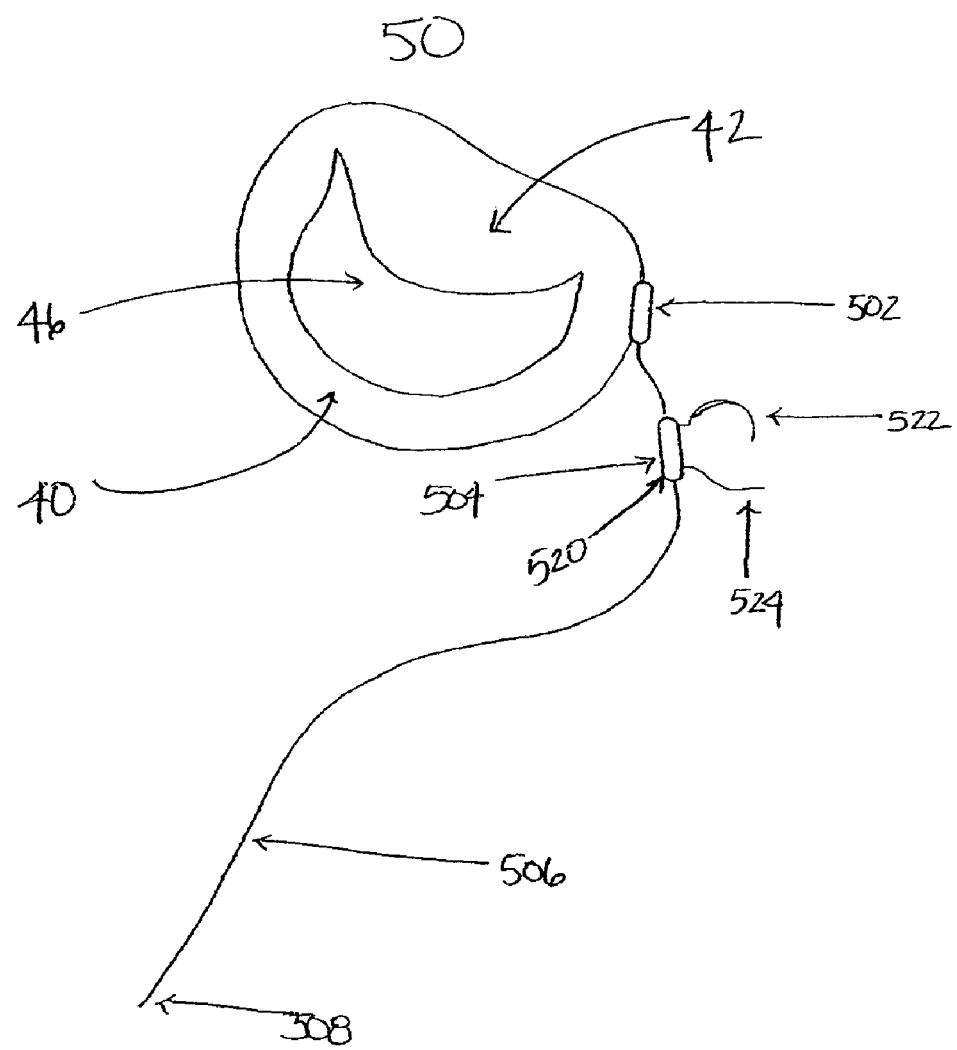
Figure 7:
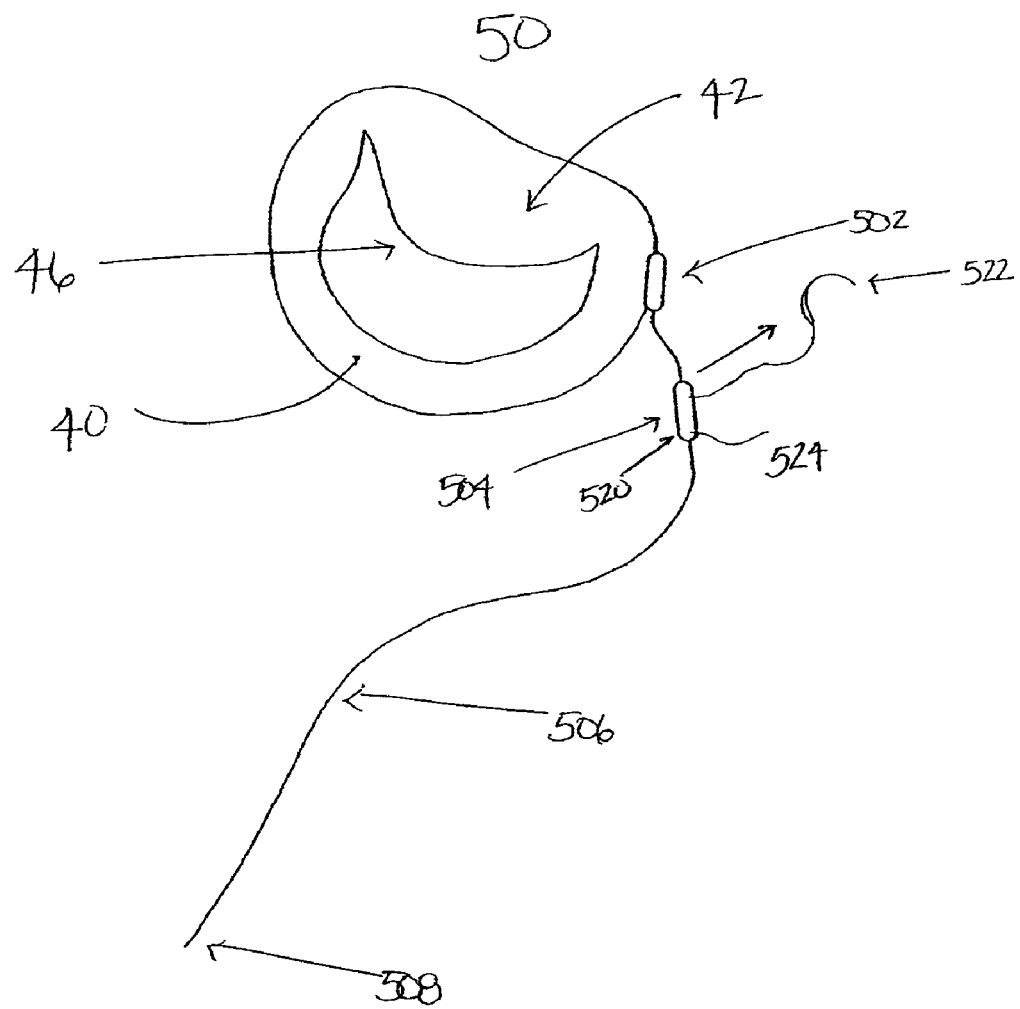

FIG. 6 is an illustration of the superior view of the dilated mitral valve of a human heart. The anchor suture support segment 502 is already shown as being attached to the mitral valve annulus 50. The anchor suture support segment is attached by the same process described in FIGS. 2G-2J. FIG. 6 shows how the first intermediate suture support segment 504 is delivered into position above the mitral valve from outside of the chest cavity by sliding the intermediate suture support segment 504 down over the supportive drawstring 506 using surgical knot pusher tool (not shown). Once the desired location is reached the surgeon will pull on the surgical needle 522 attached to the second suture 525, which will pull the second suture 525 from the intermediate suture support segment body 520 (see also FIG. 7). The intermediate suture support segment 504 is attached in the same manner as described above for the single-supportive drawstring annuloplasty system 200 in FIGS. 2K-2O.

A third embodiment of the present invention (shown in FIGS. 3A-E) also provides an annuloplasty system for repairing incompetent heart valves. This system includes: (a) a substantially circular valve reinforcing device adapted to be surgically implanted around a heart valve annulus; (b) anchoring means for attaching the substantially circular valve reinforcing device to the heart valve annulus, wherein attaching the substantially circular valve reinforcing device to the heart valve annulus reduces the circumference of the heart valve annulus by plicaing annular tissue underneath the valve reinforcing device; and (c) constricting means for reducing the circumference of the substantially circular valve reinforcing device, wherein reducing the circumference of the substantially circular valve reinforcing device further reduces the circumference of the annulus. The valve reinforcing device further includes: (i) a plurality of individual suture support segments, wherein the plurality of suture support segments further includes: a) at least one anchor segment covered with a sewing cuff, wherein the at least one anchor segment further includes a channel passing lengthwise therethrough; b) at least one terminal segment covered with a sewing cuff, wherein the at least one terminal segment further includes a channel passing lengthwise therethrough; and c) a plurality of intermediate segments disposed between the at least one anchor segment and the at least one terminal segment, wherein each intermediate segment is covered with a sewing cuff, and wherein each intermediate segment further includes a channel passing lengthwise therethrough. The anchoring means further includes: (i) a dual-armed suture, wherein at least one end of the suture is attached to surgical needle, and wherein the surgical needle passes through the sewing cuff of the anchor segment; (ii) a dual-armed suture, wherein at least-one end of the suture is attached to a surgical needle, and wherein the surgical needle passes through the sewing cuff of the intermediate segment; and (iii) a dual-armed suture, wherein at least one end of the suture is attached to a surgical needle, and wherein the surgical needle passes through the sewing cuff of the terminal segment. The constricting means further includes: (i) a supportive drawstring, wherein one end of the drawstring is secured to one end of the anchor segment, wherein the supportive drawstring passes through the channel in each intermediate segment and the channel in the terminal segment.

A method for surgically implanting this annuloplasty system includes: (a) utilizing the anchoring means for securing the substantially circular valve reinforcing device to the heart valve annulus, wherein securing the substantially circular valve reinforcing device to the heart valve annulus reduces the circumference of the heart valve annulus by plicating annular tissue underneath the valve reinforcing device, and (b) utilizing the constricting means to further reduce the circumference of the substantially circular valve reinforcing device, wherein reducing the circumference of the valve reinforcing device further reduces the circumference of the heart valve annulus by plicating the annular tissue between adjacent segments of the substantially circular valve reinforcing device, if further adjustments are required. Utilizing the anchoring means further includes: (i) affixing the suture to the heart valve annulus by passing one of the surgical needles attached to the sutures through a heart valve annulus; (ii) threading the surgical needles attached to the suture through the sewing cuff of the anchor segment; (iii) pushing the anchor segment down over the strands of the suture until the anchor segment is aligned with the heart valve annulus; (iv) securing the anchor segment to the heart valve annulus by tying the ends of the sutures together; (v) affixing another suture to a heart valve annulus as a horizontal mattress stitch by passing one of the surgical needles attached to the sutures through the heart valve annulus; (vi) threading the surgical needles attached to the suture through the sewing cuff on the first intermediate segment; (vii) using the supportive drawstring and the strands of the suture to guide the intermediate segment to the desired position above the heart valve annulus; (viii) pushing the intermediate segment down over the suture strands until the intermediate segment is aligned with the heart valve annulus; (ix) securing the intermediate segment to the heart valve annulus by tying the ends of the sutures together; (x) repeating steps (v-ix) until the desired circumference around the heart valve annulus is covered by intermediate suture support segments; (xi) threading the supportive drawstring through the channel which passes through the length of the terminal segment; (xii) affixing the suture to a heart valve annulus by passing one of the surgical needles attached to the sutures through the heart valve annulus; (xiii) threading the surgical needles attached to the suture through the sewing cuff on the terminal segment; (xiv) using the supportive drawstring and the strands of the suture to guide the terminal segment to the desired position above the heart valve annulus; (xv) pushing the terminal segment down over the strands of the sutures until the terminal segment is aligned with the heart valve annulus; (xvi) securing the terminal segment to the heart valve annulus by tying the ends of the sutures together; and (xvii) testing the repaired heart valve to verify that appropriate constriction has been achieved. Utilizing the constricting means further includes: (i) pulling the supportive drawstring to the desired tension to further decrease the circumference of the heart valve annulus if further adjustment is needed; and (ii) tying the supportive drawstring that runs through the terminal segment to the third suture attached to the end portion of the terminal segment.

FIGS. 3A-3E illustrate the third exemplary embodiment of this invention. Annuloplasty system 300 includes of an anchor suture support segment 302 with a supportive drawstring 306 attached, a plurality of identical intermediate suture support segments 304, a terminal suture support segment 310 and a plurality of identical surgical sutures 340 with attached surgical needles 342. The surgical methods used to implant the annuloplasty system 300 may be conventional open heart surgery techniques or minimally invasive heart surgery techniques.

The suture support segments, the anchor sutures support segment 302, the intermediate suture support segments 304, and terminal suture support segment 310, provide sites for suturing of the annuloplasty system 300 about the mitral valve annulus 50. Each of the suture support segments 302, 304, and 310 accommodate a single horizontal mattress suture incorporating a portion of the circumference of the mitral valve annulus 50 beneath it. The suture traverses a longer distance along the heart annulus than the size of the support segments. Sutures, when tightened and tied, create an imbrication in the valve annulus underneath the segment thereby reducing the circumference of the annulus by an amount equal to the difference between the length each suture travels in the tissue of the heart annulus and the distance between the suture bites in the support segment.

FIG. 3A depicts a cross-sectional view of a suture support segment 301. The suture support segment 301 could function as an anchor suture support segment 302, an intermediate suture support segment 304 or a terminal suture support segment 310. The support segments, 302, 304, and 310, can be cylindrical, tubular, square, round, oval, elongated oval or combinations thereof shaped as necessary to achieve the desired configuration. The suture support segment 301 has a rigid core 331 which surrounds the channel 330 that will hold the supportive drawstring 306. As shown it is a single-channel 330 but it could also be a dual channel in the suture support segment 301. The rigid core 331 is covered with a silicon rubber 313 which is covered by a polyester fabric 312. The silicon rubber 313 and the polyester fabric 312 together make up the sewing cuff 311.

The suture support segments 302, 304, and 310 have a cylindrical rigid core which includes a channel 330 passing lengthwise therethrough. The rigid core 331 can be made of any suitable material that is preferably inert, non-corrosive, non-thrombogenic and biocompatible with blood and tissue. By way of example, but not limitation, such material might be an acetal resin Delrin. The core 331 is covered with a layer of barium sulfate impregnated silicon rubber 313 and polyester knit fabric 312. The layer of silicon rubber 313 around the rigid core 331 and the polyester cover 312 provide a sewing cuff 311 for suturing of the support segments 301 about the heart valve annulus. A preferred size of the suture support segment body 320, 350, 370 is 1 mm to 4 mm in length but more preferably 2 mm to 6 mm in length, with a circumference of 1 mm to 4 mm, although other sizes and dimensions are possible. The suture support segments 302, 304, and 310 must be rigid or semi-rigid in the longitudinal dimension, and must not be deformable, such that when the sutures 340 are tied against the suture support segment body 370, 320, 350 to secure the suture support segment 302, 304, 310 to the mitral valve annulus 50, the suture support segment body 370, 320, 350 does not buckle.

FIG. 3A is an illustration of the superior view of the dilated mitral valve of a human heart. As depicted the dilated mitral valve has a gap 46 between the anterior and posterior leaflets 42 and 40. FIG. 3A also depicts a side view of a suture support segment 302, 304 or 310. As depicted it is labeled 302. The suture support segment has channel passing lengthwise therethrough.

Figure 3B:
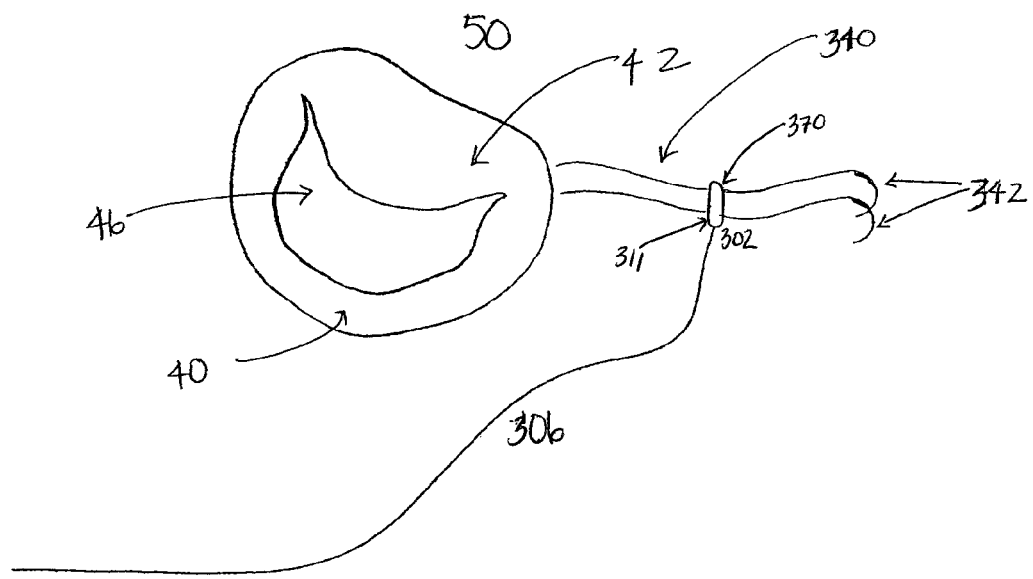

FIGS. 3A and B depict the implantation of the anchor suture support segment 302 into the mitral valve annulus 50. A double-arm suture 340 is placed as a mattress horizontal stitch in the posterior annulus of the mitral valve and then passed through the sewing cuff 311 of the anchor suture support segment 302. As shown in FIG. 3B the surgical needles 342 are used to pierce the sewing cuff 311 of the anchor suture support segment 302. The sutures 340 that have passed through the surgical cuff 311 of the anchor support segment 302 are then used to slide the anchor suture support segment 302 down onto the desired location of the mitral valve annulus 50.

Figure 3C:
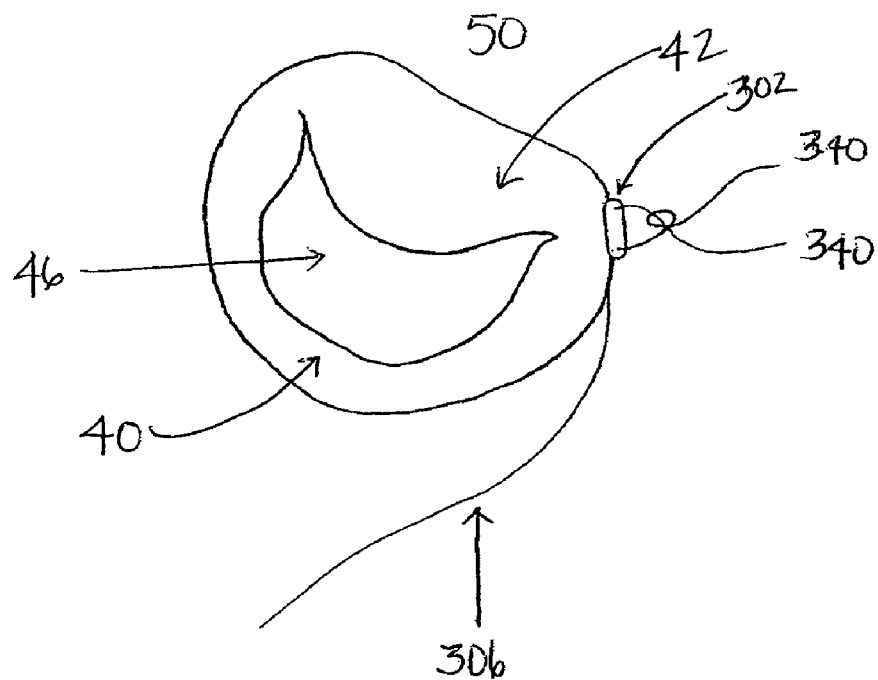

FIG. 3C depicts the securing of the anchor suture support segment 302 to the mitral valve annulus 50. Once the anchor support segment 302 is aligned with the mitral valve annulus 50 the surgical needles 342 are cut off from the sutures 340 and the free ends of the sutures 340 are knotted together, with sufficient tension thereby securing the anchor suture support segment 302 in place on the mitral valve annulus 50.

Figure 3D:
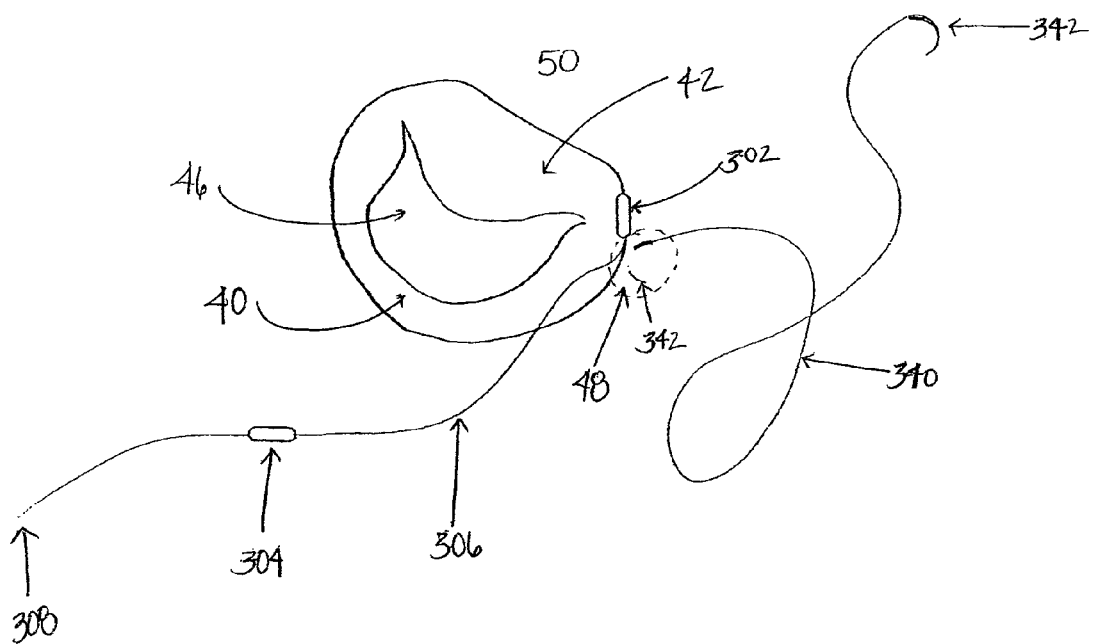

FIG. 3D shows the implantation of the first intermediate suture support segment 304 according to the current embodiment of the invention. A new horizontal mattress stitch is placed 2-4 mm from the proximal end of the anchor support segment 302 at the surgical site 48. The supportive drawstring 306 is used to guide the intermediate suture support segment 304 toward the mitral valve annulus 50.

Figure 3E:
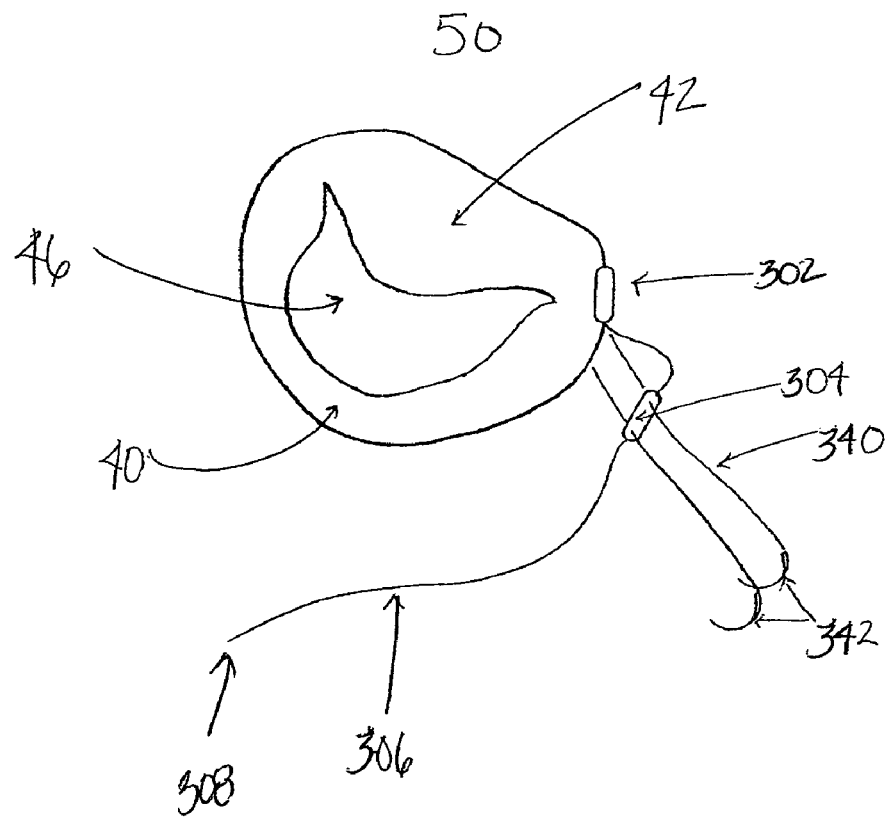

FIG. 3E depicts the sliding down of the intermediate suture support segment 304 to the mitral valve annulus 50. As shown in FIG. 3D the supportive drawstring 306 and the sutures 340 that have passed through the sewing cuff 311 of the intermediate suture support segment 304 are used to lower the intermediate suture support segment 304 to the desired location. The surgical needles 342 of the sutures 340 are used to pierce the sewing cuff 311 of the intermediate suture support segment 304. Once the intermediate support segment 304 is aligned with the mitral valve annulus 50 the surgical needles 342 are cut off from the sutures 340 and the free ends of the sutures 340 are knotted together, with sufficient tension thereby securing the intermediate suture support segment 304 in place on the mitral valve annulus 50. This process described in FIGS. 3D-3E is repeated until the desired circumference around the mitral valve annulus 50 is covered with intermediate suture support segments 304.

After the last intermediate suture support segment 304 is secured on the mitral valve annulus 50, a terminal suture support segment 310 will be implanted like described in FIGS. 3E-3E. Next, the mitral valve will be tested for competence by distending the left ventricle with isotonic solution infused through rubber-bulbed syringe. If needed the annuloplasty system will be adjusted by pulling the supportive drawstring 306. To complete the annuloplasty system 300 the free end 308 of the supportive drawstring 306 then will be tied together with the free suture attached to the end of the terminal suture support segment 310. After seven or eight knots are made the free tails are cut at the point beyond the terminal suture support segment 310 by any suitable means completing the annuloplasty.

A fourth embodiment of this invention (shown in FIGS. 4A-H) also provides an annuloplasty system for repairing incompetent heart valves without traditional knotting. This system includes: a substantially circular flexible valve reinforcing device adapted to be surgically implanted into a heart valve; anchoring means for attaching the substantially circular valve reinforcing device to the heart valve annulus and for pleating the annulus to reduce its circumference to substantially that of the valve reinforcing device. The valve reinforcing device further includes: a core formed of a plurality of thin fibers which are held together by a tubular polyester velour cloth. The anchoring means further includes: (i) a suture containing at least one surgical needle at each proximal end of the suture; and (ii) a plurality of barbed structures formed at a medial point on the suture with a first barb structure being placed a distance away from a second barb structure to create a bridge area, wherein the first barbed structure is oriented to permit passage of the suture through the heart valve annulus in a forward direction and prevent movement in a reverse direction, and wherein the second barbed structure is oriented to prevent passage of the suture through the heart valve annulus in a forward direction A method for surgically implanting this annuloplasty system includes: (a) utilizing the anchoring means to secure the substantially circular valve reinforcing device to the heart valve annulus. Utilizing the anchoring means further includes: (i) inserting one of the surgical needles of the suture apparatus into the heart valve annulus and pulling the surgical needle which draws the first portion of the suture through the heart valve annulus until the barbs of the second barbed structure engage the surface of the annulus at the insertion point preventing further advancement of the suture into the heart valve annulus; (ii) inserting another suture apparatus into the heart valve annulus 2-4 mm apart from the previous stitch and pulling the surgical needle which draws the first portion of the suture through the heart valve annulus until the barbs of the second barbed structure engage the surface of the heart valve annulus at the insertion point preventing further advancement of the suture into the heart valve annulus; and (iii) repeating step (ii) until the entire circumference of the posterior annulus of the mitral valve is evenly sutured. (iv) using both surgical needles of each of the suture apparatus to pierce the annuloplasty ring wherein the suture attached to the surgical needles lower the annuloplasty ring over the sutures into position above the heart valve annulus; (v) pushing the annuloplasty ring onto the barbed structures wherein the barbed structures catch the thin fibers in the annuloplasty ring; (vi) using the barbed structures to hold the annuloplasty ring into place; and (vii) cutting off the surgical needles and the remaining suture material.

FIGS. 4A-4H depict the fourth embodiment and method for attaching an annuloplasty system to a damaged mitral valve according the present invention. The annuloplasty system 400 includes a double-armed barbed suture 420 which further includes a plurality of elongated sutures 424 having one or more spaced barbs 426 and 428 projecting from the surface of the suture 424. Barbs 426 and 428 are configured to allow passage of the suture 424 in one direction through the heart tissue and an annuloplasty ring or band 450 but resist movement of the suture 424 relative to the heart tissue and the annuloplasty ring or band in the opposite direction. The surgical methods used to implant the annuloplasty system 400 may be conventional open heart surgery techniques or minimally invasive heart surgery techniques.

Figure 4B:
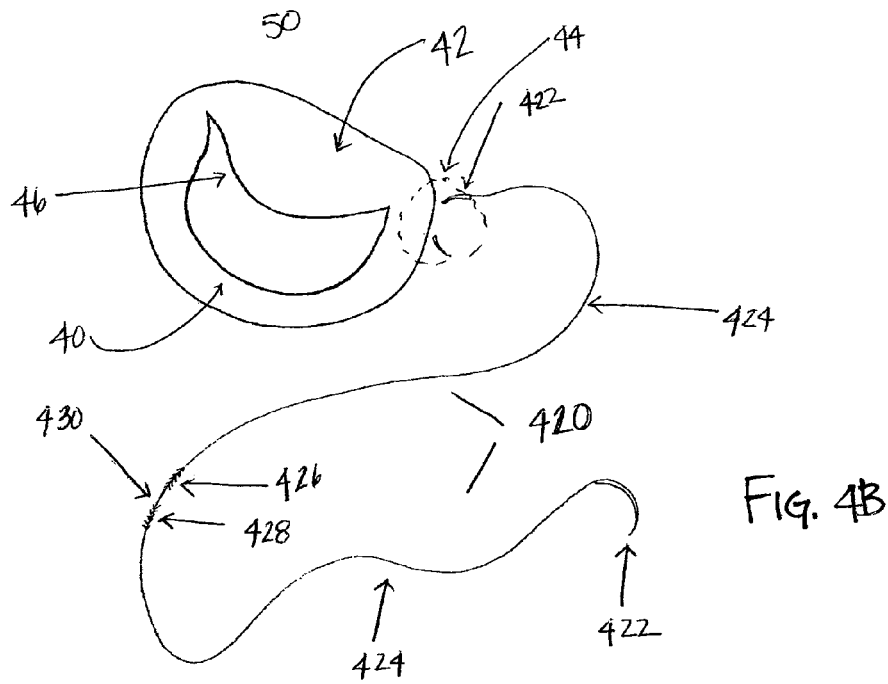
FIGS. 4A-4H illustrate a fourth exemplary embodiment of the annuloplasty system and surgical implantation method of the present invention wherein a dual-armed suture with barbs and an annuloplasty ring or band are utilized.
Figure 4A:
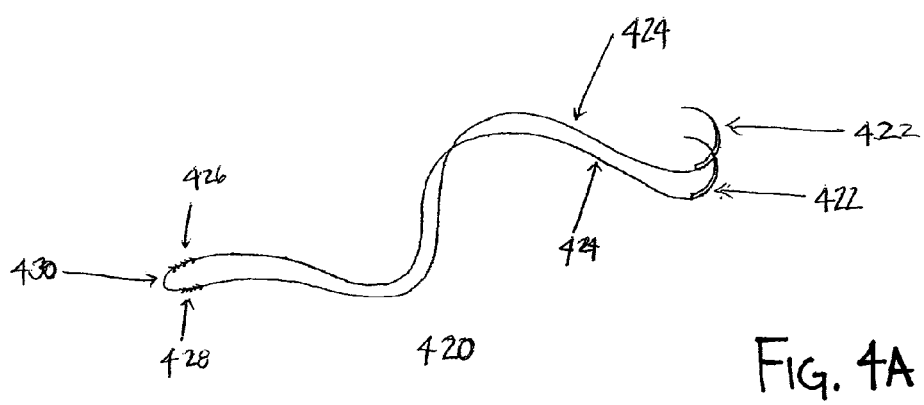

FIG. 4A depicts one of the double-armed barbed sutures 420 of annuloplasty system 400. The double-armed barbed suture 420 is comprised of a suture 424, surgical needles 422, barbs 426, 428 and a bridge between the barbs 430. The suture 424 has attached to each end a surgical needle 422. The suture 424 also has attached to the surface thereof a set of barbs 426 and 428 facing in opposite directions. The suture 424 includes a set of barbs 426 oriented in one direction on one side of a bridge 430 and another set of barbs 428 oriented in the opposite direction on the other side of the bridge 430. The barbs 426 and 428 are configured to only allow passage of the suture 424 in one direction through mitral valve annulus 50.

FIG. 4B is an illustration of the superior view of the dilated mitral valve of a human heart. As depicted the dilated mitral valve has a gap 46 between the anterior and the posterior leaflets 42 and 40. FIG. 4B also depicts the method of implantation of annuloplasty system 400 into heart valve annulus 50. The surgeon will insert one of the surgical needles 422 into the mitral valve annulus 50 at the surgical site 44 and will advance the surgical needle 422 through the mitral valve annulus 50 until the needle 422 emerges from the mitral valve annulus 50.

Figure 4C:
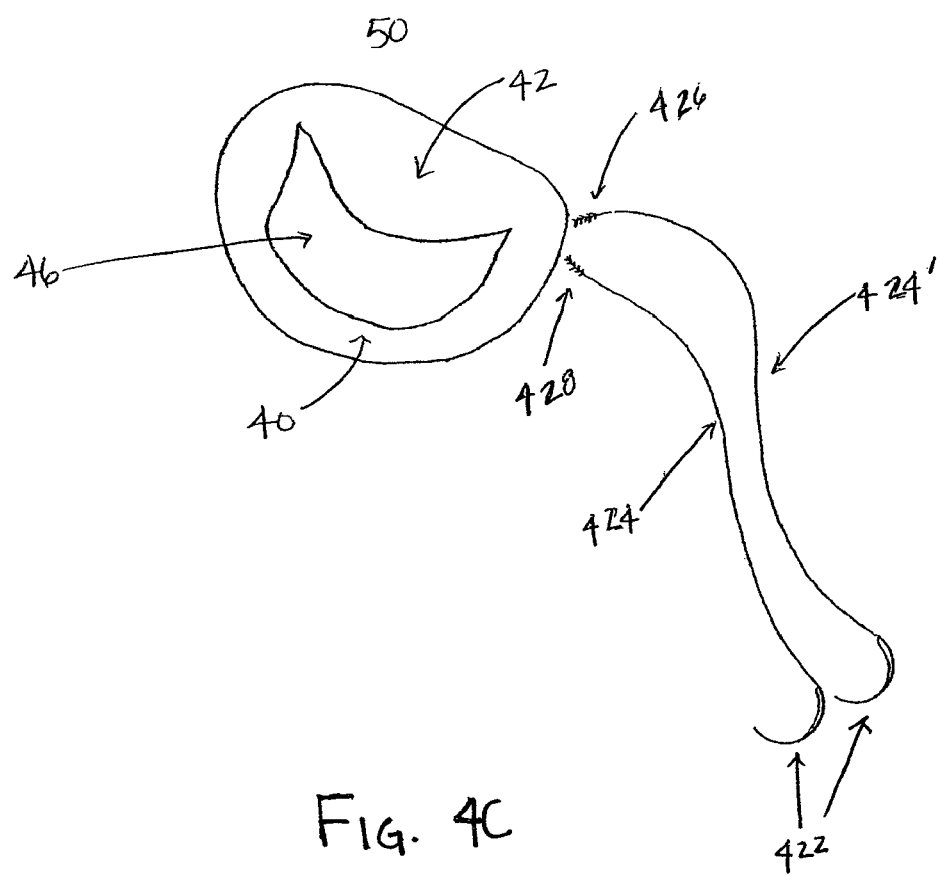

FIG. 4C shows the next step in which the surgeon will grip the surgical needle 422 and pull the surgical needle 422 out of the mitral valve annulus which draws the first portion 424' of the suture body 424 through the mitral valve annulus 50 until the barbs 428 of the second portion of the suture body 424 engage the surface of the mitral valve annulus 50 at the insertion point preventing further advancement of the suture 424 into the mitral valve annulus 50.

Figure 4D:
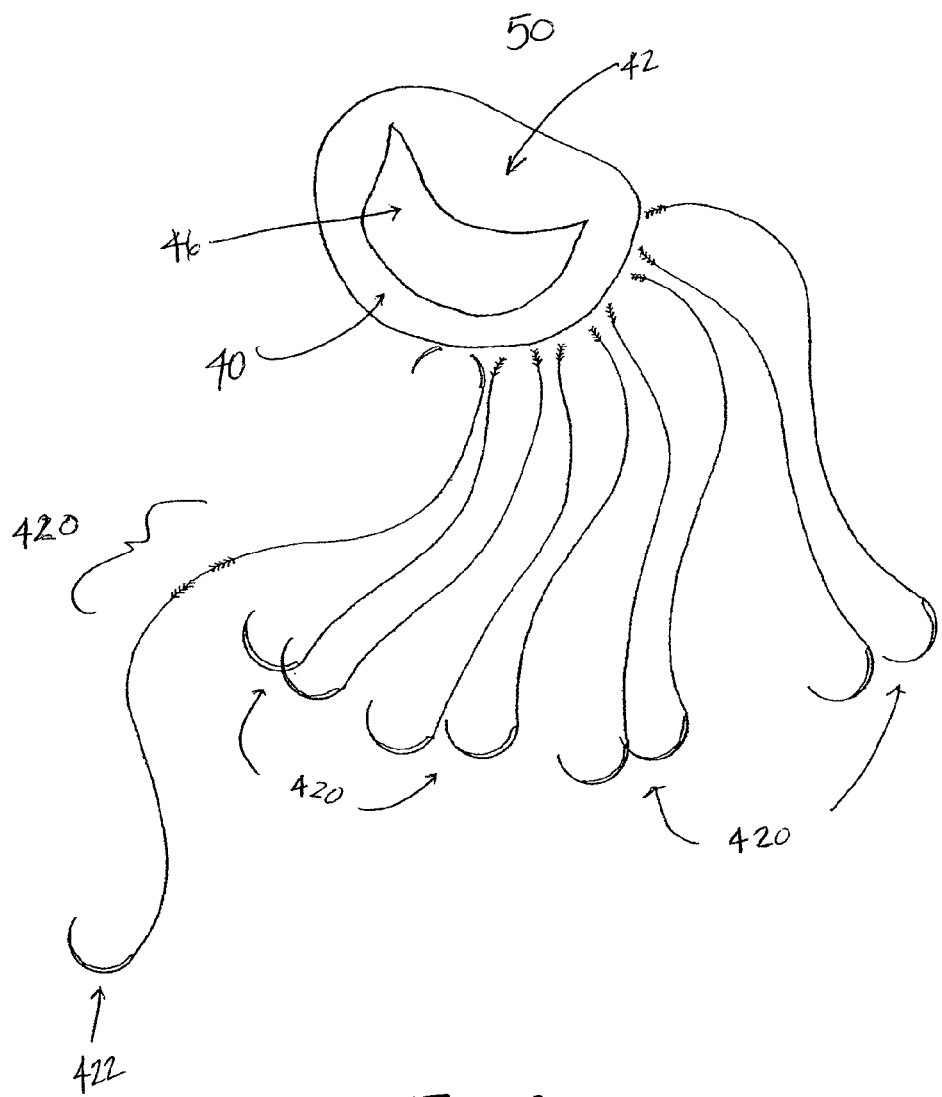
Figure 4E:
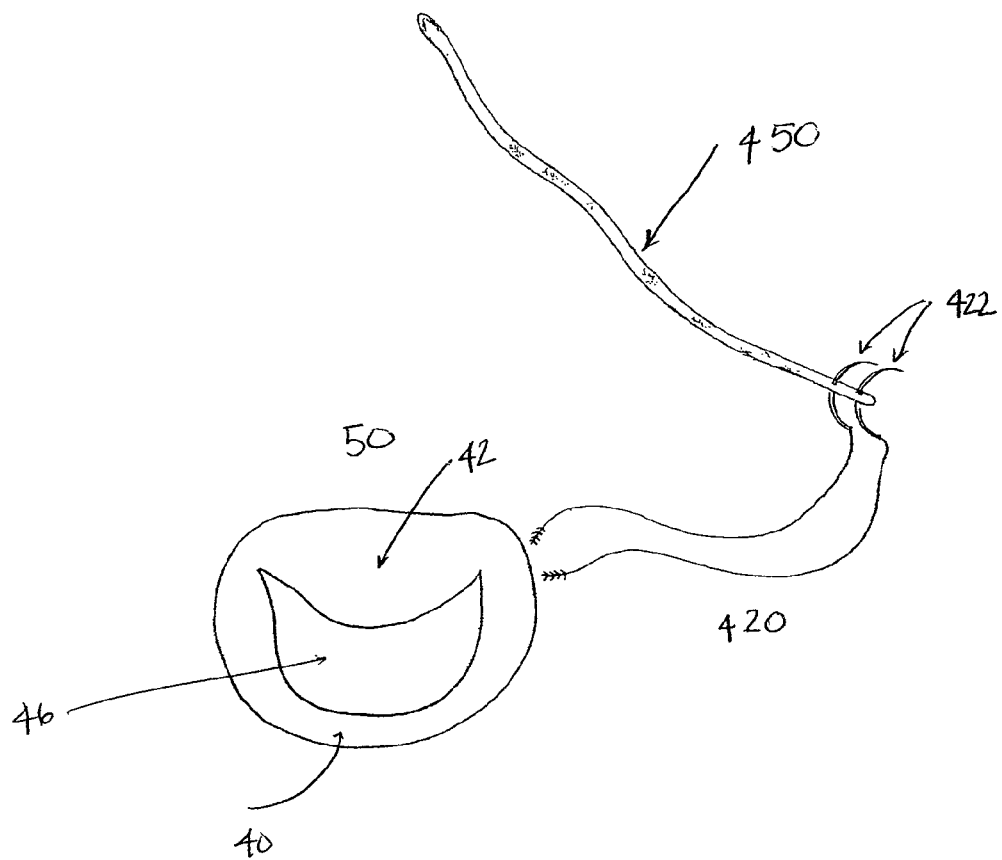
Figure 4F:
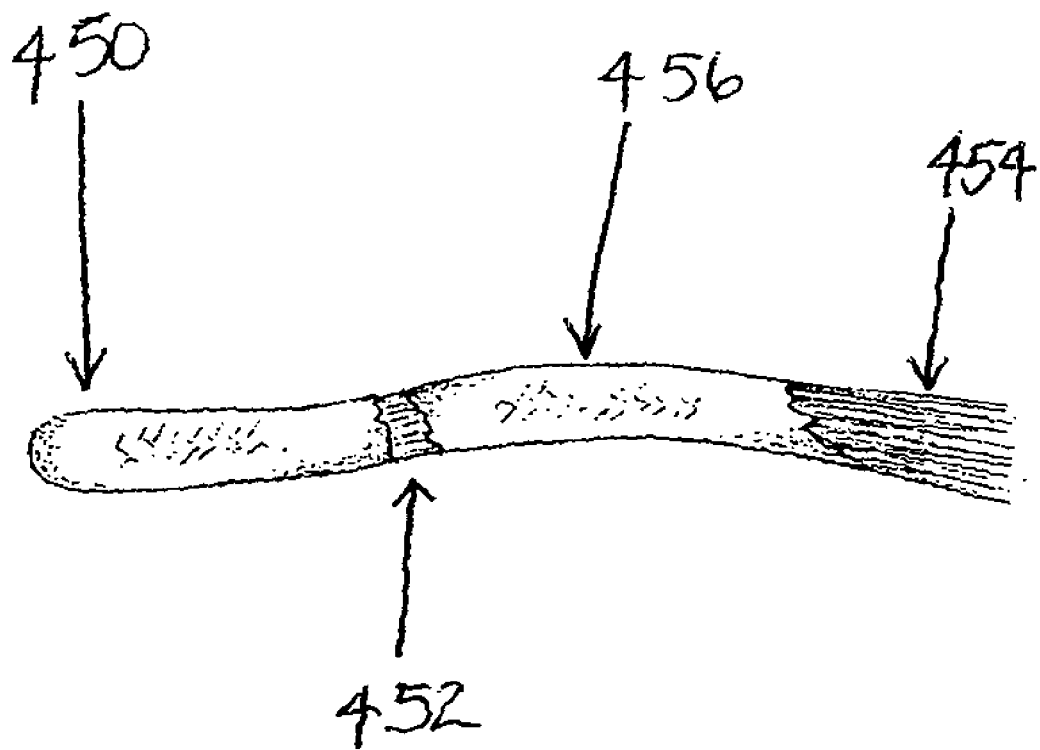

FIG. 4D shows many double-armed barbed sutures 420 attached to the mitral valve annulus 50 by the means described above in FIGS. 4B-4C. For clarity, FIG. 4E shows only one of the double-armed barbed sutures 420 attached to the mitral valve annulus 50 but it also depicts how the annuloplasty band or ring 450 is pierced with the surgical needles 422. In FIG. 4E the annuloplasty band/ring 450 has been penetrated by the surgical needles 422 attached to the sutures 424 which has been passed through the mitral valve annulus 50 by means of the method described above in FIGS. 4B-4C. FIG. 4F is a detailed view of the annuloplasty band/ring 450. This view shows how the annuloplasty band/ring 450 is comprised. The annuloplasty band/ring 450 has a core 452. The core 452 of the annuloplasty band is made up of a plurality of distinct thin fibers 454. The plurality of thin fibers 454 that make up the core 452 of annuloplasty band/ring 450 are covered with a tubular polyester velour cloth 456.

Figure 4G:
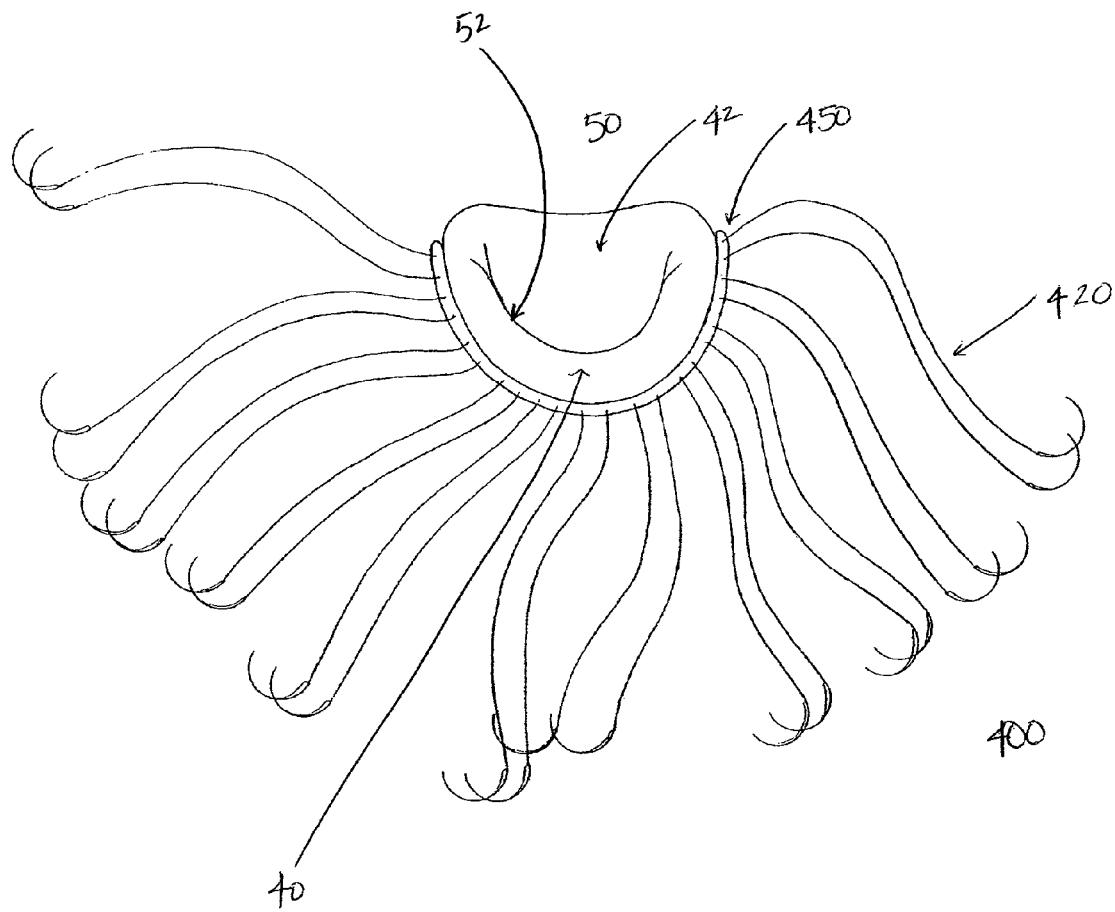
Figure 4H:
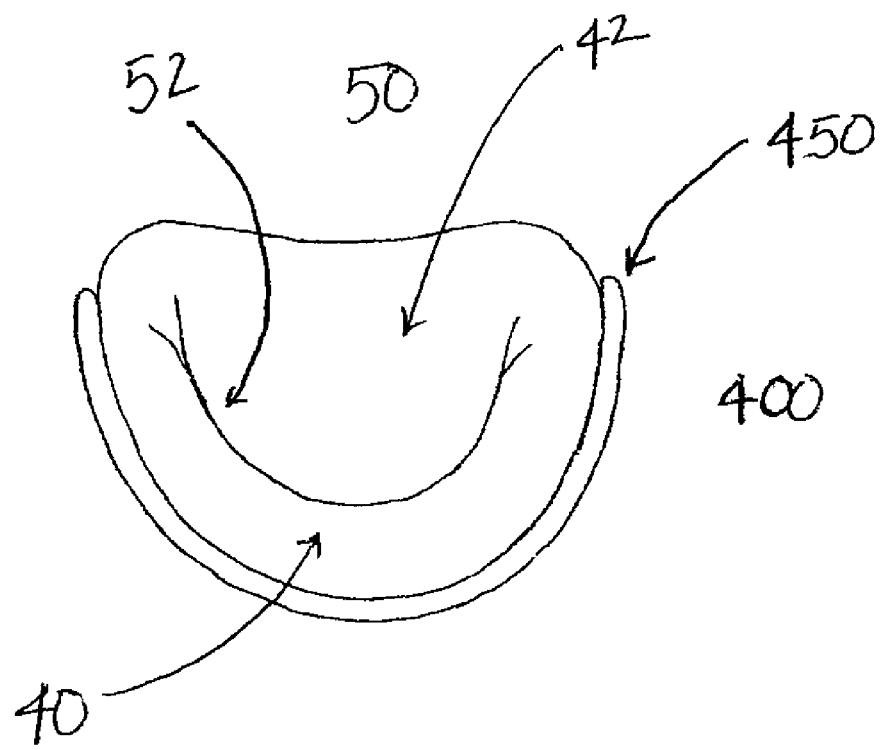

FIG. 4G shows the full annuloplasty system 400 with all of the double-armed barbed sutures 420 attached to the mitral valve annulus 50 and passed through the annuloplasty ring 450 wherein the annuloplasty ring 450 is lowered in place above the mitral valve annulus 50 over the strands of the double-armed barbed sutures 420. The next step will be for the surgeon to secure the annuloplasty ring 450 onto the barbed structures 426 and 428 wherein the barbed structures 426 and 428 catch the thin fibers 454 in the annuloplasty ring 450. The barbs 426 and 428 facing upwards from the mitral valve annulus 50 will catch the annuloplasty ring 450 and will hold the annuloplasty ring 450 onto the mitral valve annulus 50 with out having to tie the sutures. Once the annuloplasty ring 450 is secured into place on the mitral valve annulus 50 the excess suture 424 protruding through the annuloplasty ring 450 is cut at a point against the annuloplasty ring 450. The barbs 426 and 428 will hold the annuloplasty ring 450 in place on the mitral valve annulus 50 because the barbs 426 and 428 grip the thin fibers 454 and the polyester velour cloth cover of the annuloplasty band/ring 450. FIG. 4H is a superior view of a repaired mitral valve annulus 50 with attached and completed annuloplasty system 400.

FIGS. 8-26 depict various alternate methods used to attach suture support segments quickly in the heart valve annulus without traditional knotting.

Figure 8:
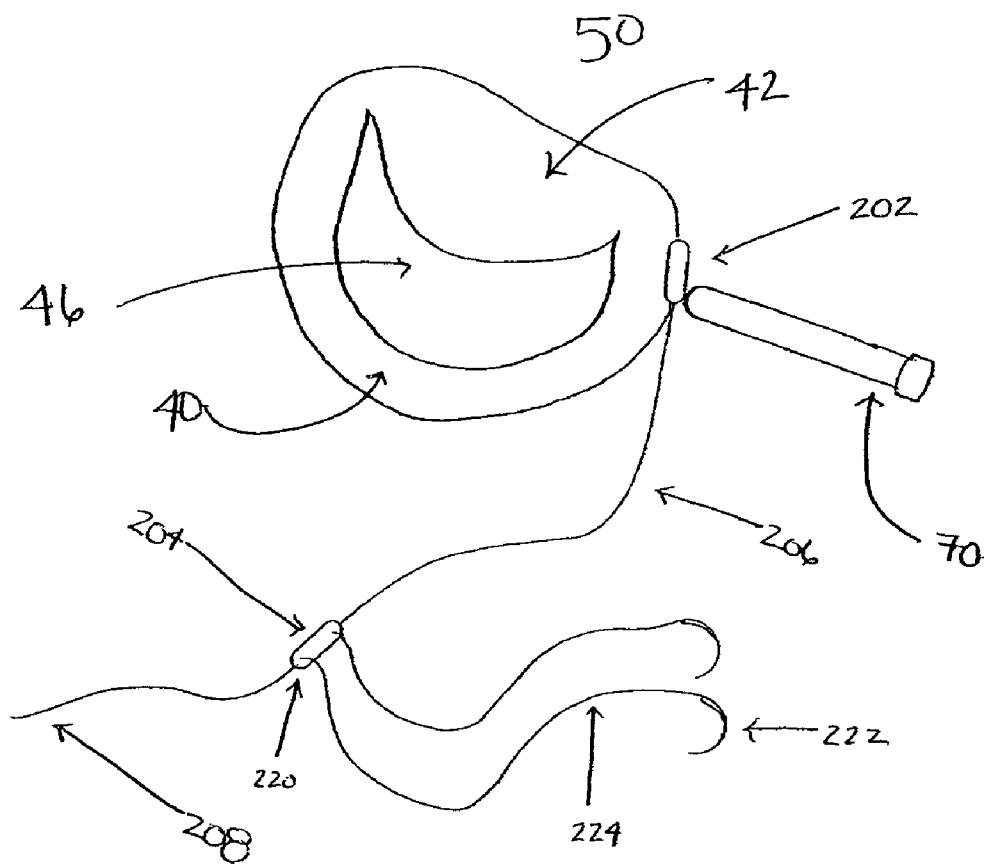
FIG. 8 illustrates a method of attaching suture support segments using an intracardiac ultra sonic welder.

FIG. 8 provides an illustration of the superior view of the dilated mitral valve of a human heart. As depicted the mitral valve has a gap 46 between the anterior and posterior leaflets 42 and 40. Any of the above described annuloplasty systems (100, 200, 300, 400, 500) are compatible with this method but the single supportive drawstring annuloplasty system 200 is depicted. FIG. 8 depicts the use of an intracardiac ultrasonic suture welder 70, a novel tool that allows one to secure interrupted sutures under tension without tying knots. As pictured the anchor suture support segment 202 has already been implanted in the mitral valve annulus 50. Instead of knotting the sutures 274 together to secure the anchor suture support segment body 270 to the heart valve annulus 50, the two ends of each suture 274 (not shown) can be threaded through the end of an intracardiac ultrasonic suture welder 70. Tension in the sutures 274 is adjusted using downward pressure with the tip of the intracardiac ultrasonic suture welder 70 as well as upward traction on the end of each suture 274 strand. The intracardiac ultrasonic suture welder 70 is then actuated (not shown). Successful welding of each suture 274 is confirmed by visual inspection, and the suture tails are cut 1-2 mm from the weld. This process is repeated for each intermediate suture support segment 204 until the desired circumference around the mitral valve annulus 50 is covered.

Figure 10:
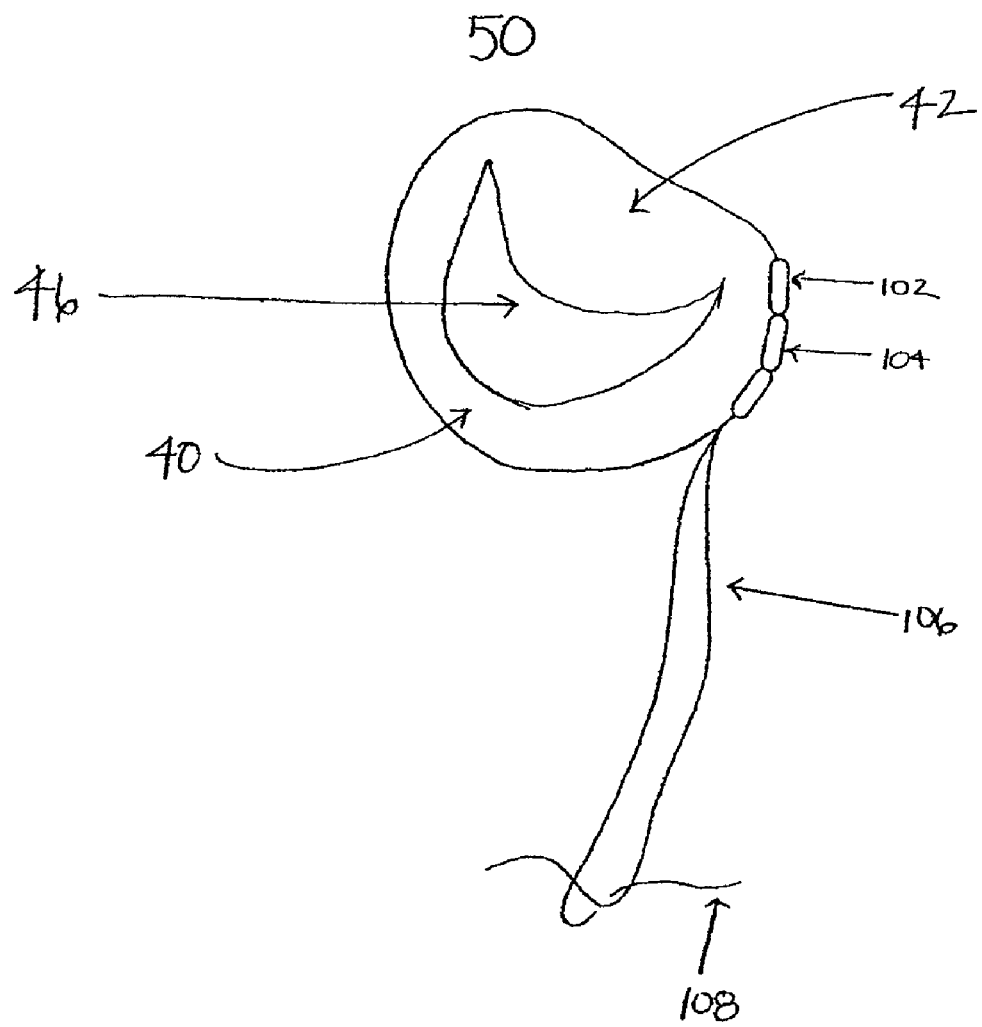
FIGS. 9-11 illustrate a method of attaching suture support segments having an eye-like opening using a one-way suture that includes barbs.
Figure 9:
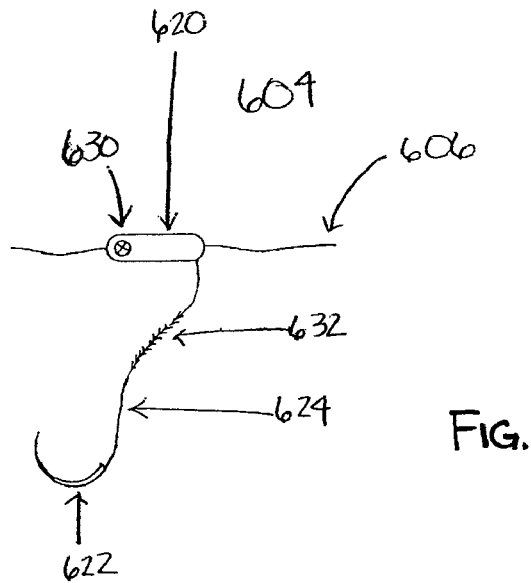
Figure 10:
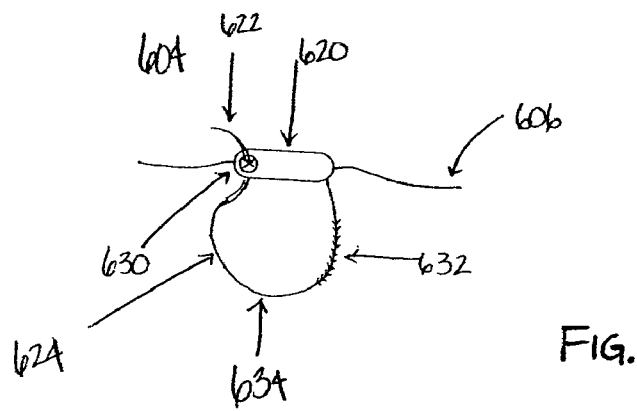
Figure 11:
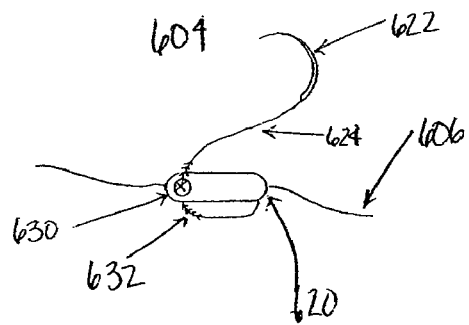

FIGS. 9-11 depict another alternative embodiment of a suture support segment that does not use traditional knotting to secure the suture support segment body to the mitral valve annulus. The annuloplasty system can be any of the above described having a single supportive drawstring (200) or a dual-supportive drawstring (100).

FIG. 9 depicts an intermediate suture support segment 604. The intermediate suture support segment 604 is made up of an intermediate suture support segment body 620, a suture 624, a surgical needle 622, an eye 630, and barbs 632. A supportive drawstring 606 (may be a single or dual supportive drawstring, the dual supportive drawstring is not shown) is threaded through the channel(s) in the intermediate suture support segment body 620. This supportive drawstring 606 is used to guide the intermediate suture support segment 604 to the desired location on the mitral valve annulus. The intermediate suture support segment body 620 has an eye 630 with ratchet means. Attached to the other end of the intermediate suture support segment body 620 is a suture 624 with an attached surgical needle 622. The suture 624 has attached on the exterior distal surface a set of barbs 632. The orientation of the barbs 632 make the suture 624 a one-way suture because barbs 632 will only allow passage of the surgical needle 622 and suture 624 in one direction through the heart tissue and the eye 630, but not in the opposite direction.

FIG. 10 shows how the surgical needle 622 is used to thread the suture 624 through the heart tissue and is then passed through the eye 630 to lead the suture 624 there through, whereby the suture 624 is formed into a loop 634. FIG. 11 shows how the latching means of the eye 630 and barbs 632 permits forward movement of the suture 624 through the eye 630 but retains the suture 624 securely against reverse movement through the eye 630. Note that the anchor suture support segment (not shown) used with this embodiment will have the same configuration as the intermediate suture support segment 604, except that the supportive drawstring 606 is attached to the anchor suture support segment instead of running through a channel(s) of the anchor suture support segment body.

Figure 12:
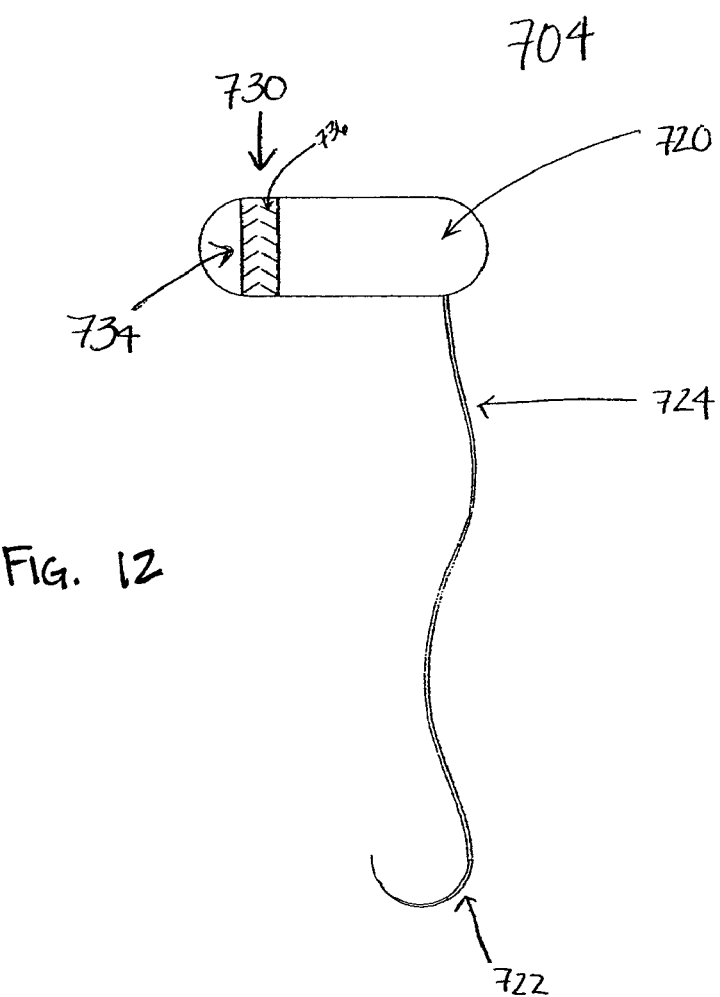
FIGS. 12-13 illustrate a method of attaching suture support segments having a one-way suture retaining device embedded therein for attaching the suture without tying.
Figure 13:
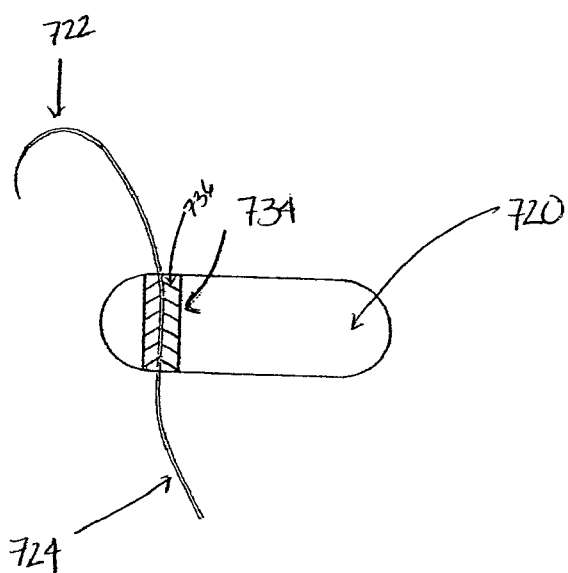

FIGS. 12-13 depict another means of attachment without traditional knotting using a suture support segment 704 that has an opening 730 with a one-way suture-retaining device 734 with flexible fingers, barbs or series of sheets 736 that are configured to engage the braided suture 724. The fingers or barbs 736 preferably have sharp points inclined in a common axial direction for purposes of preventing the braided suture 724 from sliding relative to suture support segment 704 in a direction opposite to the direction of inclination of barbs 736. The suture-retaining device 734 has a passage of a sufficient diameter to allow a braided suture 724 to easily pass through opening 730 with little resistance, but small enough to allow flexible fingers or barbs 736 to engage the braided suture 724 when the braided suture 724 in the suture-retaining device 734 is moved in a direction opposite to the direction of inclination of barbs or fingers 736. Thus, the braided suture 724 is locked into position (see FIG. 13).

Figure 14:
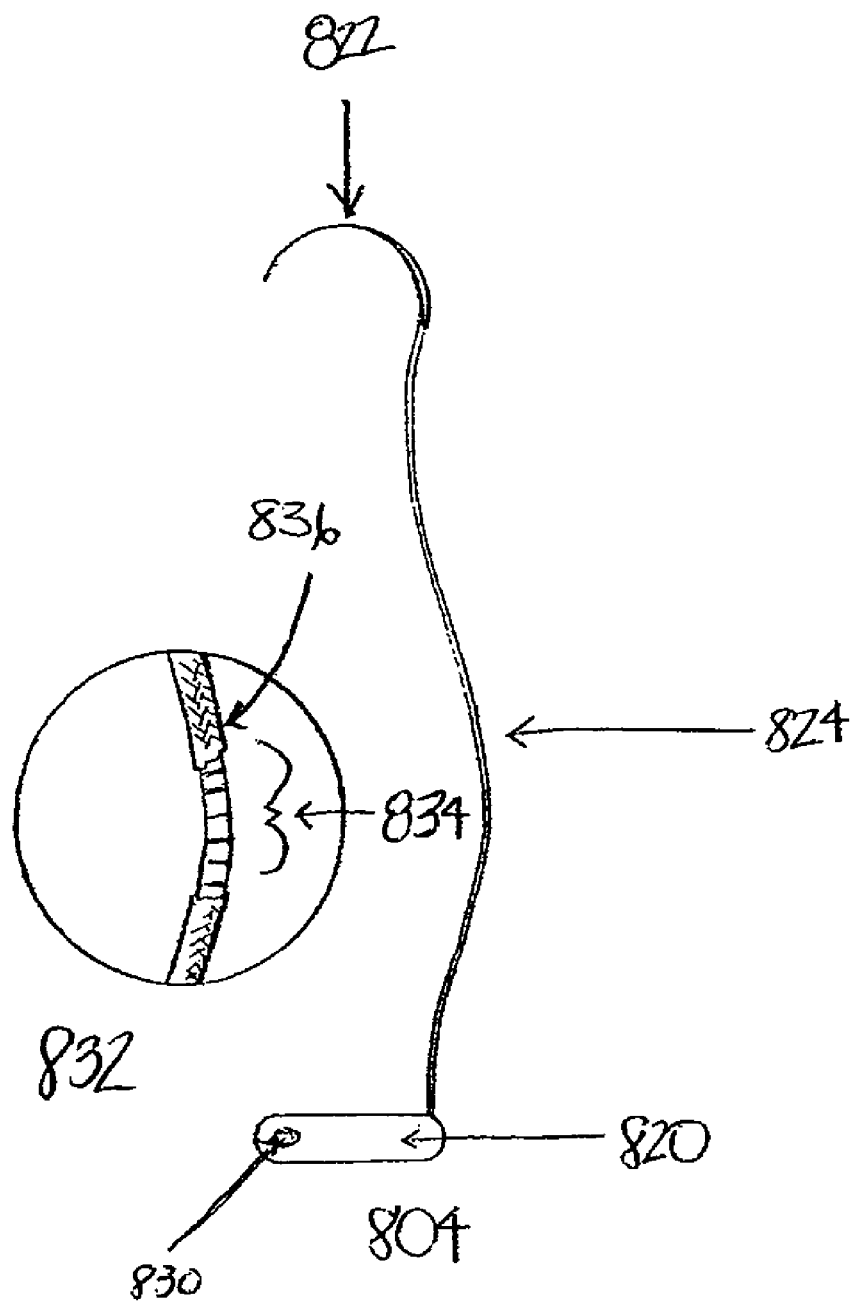
FIGS. 14-15 illustrate a method of attaching suture support segments using a braided suture and a suture support segment with a locking device.
Figure 15:
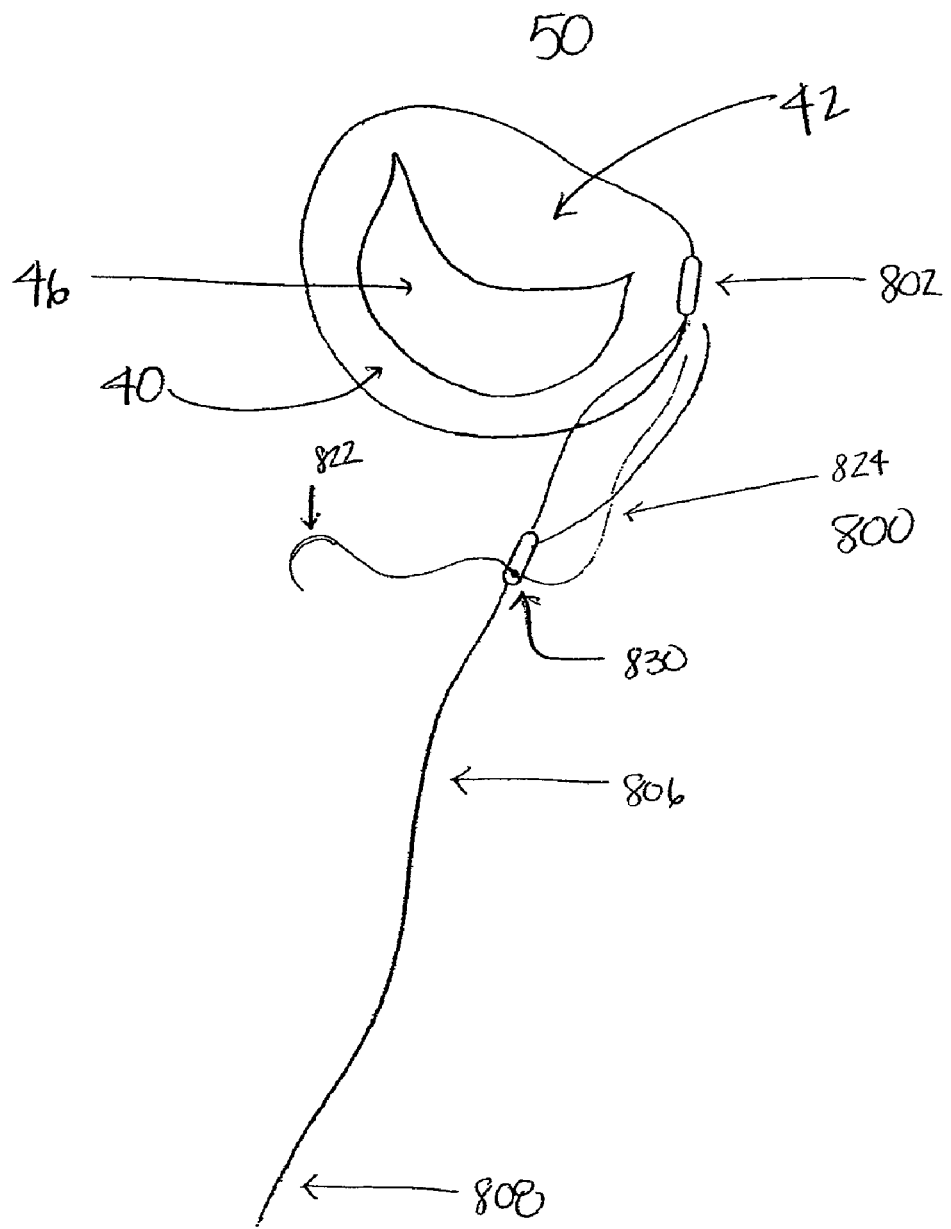

FIGS. 14-15 depict yet another embodiment of the present invention that uses a method to secure the suture support segment in place without traditional knotting and an annuloplasty system using the securing method. FIG. 14 depicts an intermediate suture support segment 804 which is comprised of an intermediate suture support segment body 820, a braided suture 824, a surgical needle 822, a locking device 830, and a channel(s) which is not shown. The braided suture 824 has a core 832, formed of a plurality of fibers which are held together by a tubular braided cover 836. The fibers are thermally bonded together, to form rigid bridges 834, at selected short intervals along the longitudinal axis of the braided suture 824. These rigid bridges 834 are formed from thermally bonded fibers which are configured to allow passage of the braided suture 824 in one direction through locking device 830 but significantly resist movement of the braided suture 824 in the opposite direction and prevent the braided suture 824 from slipping back through the locking device 830.

FIG. 15 provides an illustration of the superior view of the dilated mitral valve of a human heart. As depicted the dilated mitral valve has a gap 46 between the anterior and posterior leaflets 42 and 40. As shown an anchor suture support segment 802 with an attached supportive drawstring 806 is already secured to the mitral valve annulus 50. The channel of intermediate suture support segment 804 is threaded through the free end 808 of the supportive drawstring 806, which is shown as a single supportive drawstring but it could be a dual-supportive drawstring. The supportive drawstring 806 is used to guide each intermediate suture support segment 804 to the desired location on the mitral valve annulus 50. The surgical needle 822 attached to the intermediate suture support segment 804 is used to make a horizontal mattress stitch in the mitral valve annulus 50. Once this is completed the surgical needle 822 is passed through the eye of the locking device 830 of the intermediate suture support segment body 820. The braided suture 824 is pulled through the eye of the locking device 830 while the intermediate suture support segment body 824 is pushed down toward the mitral valve annulus 50 until the required tension is obtained in the loop and thereafter the excess length of the braided suture 824 protruding through the eye of the locking device 830, is cut away. Such an embodiment allows accurate control over the braided suture 824 tension without having to tie a knot. Alternatively a specially constructed tool (not shown) similar to a cable tie tension and cutter tool can be used. The tool would have a tensioning mechanism for tensioning the suture to a predetermined tension setting and a cutting mechanism for cutting the excess portion of the suture tail after the desired tension is achieved.

Figure 16:
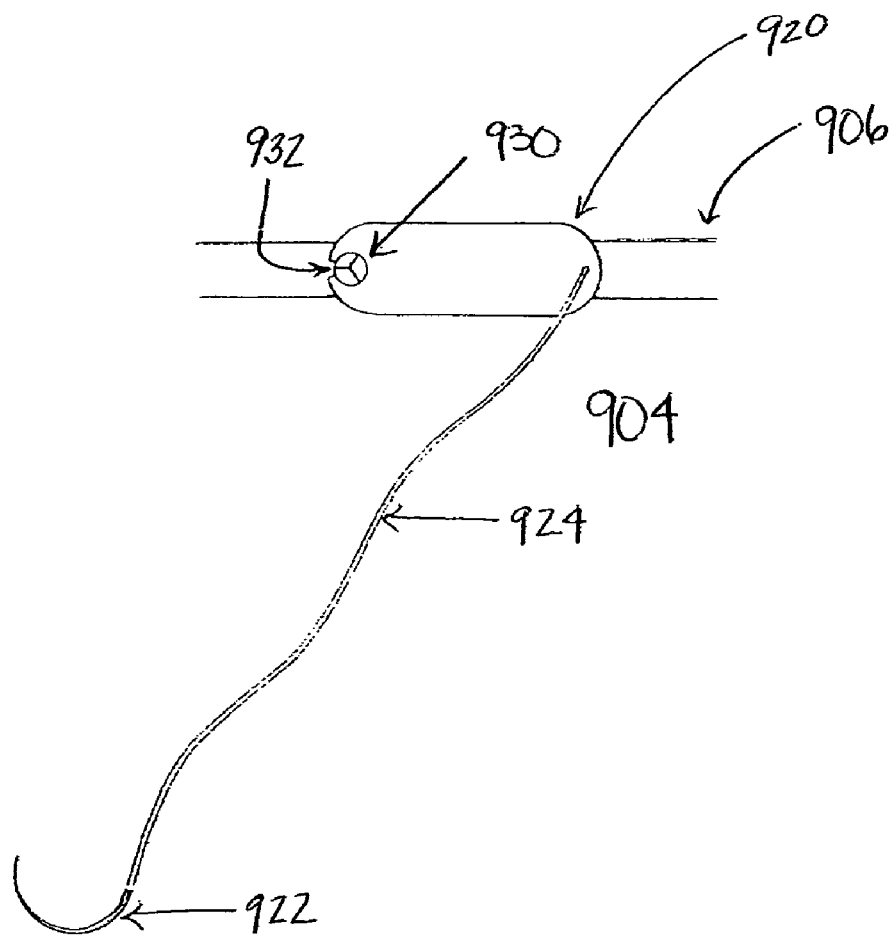
FIG. 16 depicts a suture support segment having a locking device that allows for lateral insertion of the suture material into the suture segment body.

FIG. 16 depicts still another embodiment of the present invention that uses an opening 930 which provides a slot or passageway 932 for enabling a lateral insertion of suture 924 into opening 930. As described above in both single and dual supportive drawstring systems the intermediate suture support segments 904 are be slid down over the supportive drawstring 906 into position above the mitral valve (not shown).

The surgical needle 922 is passed through the mitral valve annulus, and then the surgical needle 922 would be slipped through slot or passageway 932 into opening 930 of the suture-retaining device. The suture is then pulled through the opening 930 while the intermediate support segment 904 is pushed down toward the heart annulus until the required tension is obtained in the loop and thereafter the excess length of the suture 924 protruding through the opening 930, is cut away.

Figure 17:
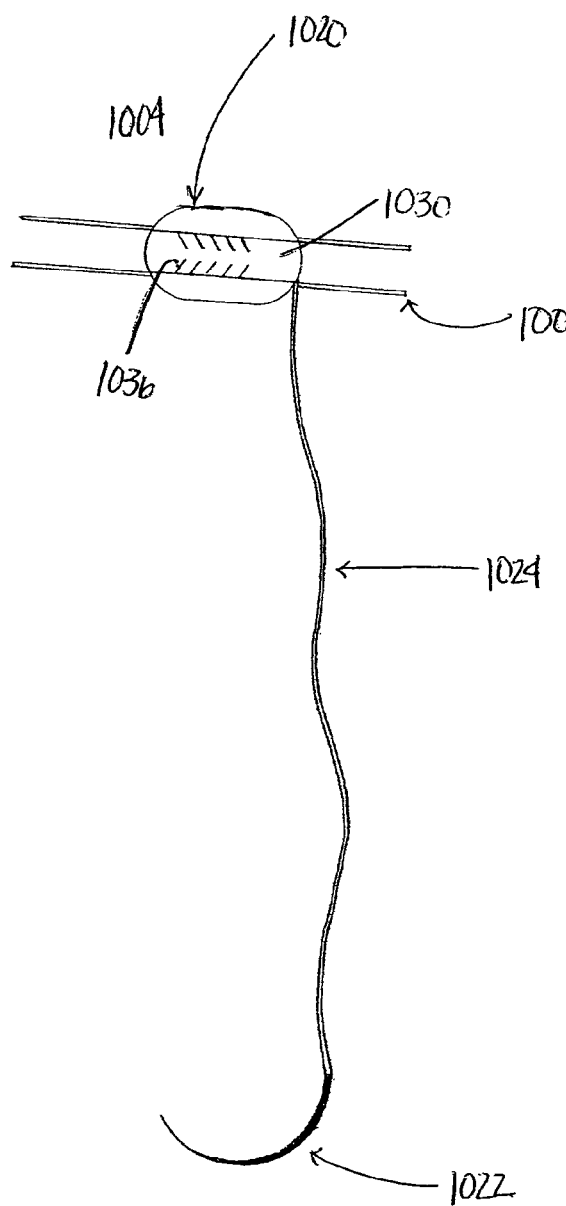
FIGS. 17-18 illustrate a method of using a suture support segment having a lumen for use in attachment.
Figure 18:
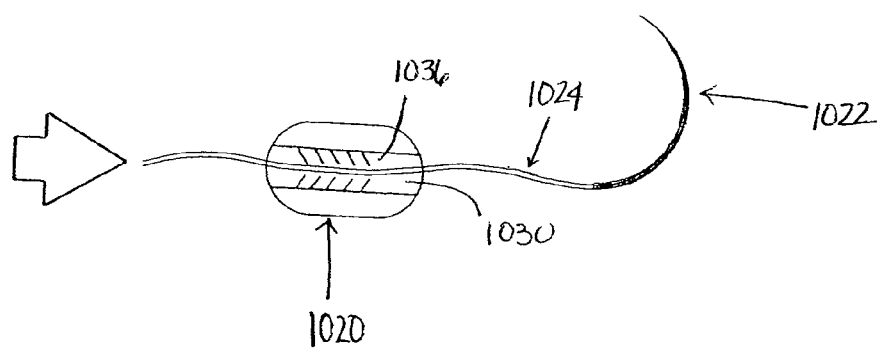

FIG. 17 illustrates another locking device utilizable with the method discussed above. The suture support segment 1004 has a lumen 1030 formed along the entire axial length of the suture support segment body 1020. Attached to the outside of the sutures support segment 1004 on the suture support segment body 1020 is a braided suture 1024 with an attached surgical needle 1022. The interior of the suture support segment body 1020 is made up of a lumen 1030 which is comprised of a plurality of barbs 1036 inclined in a common axial direction for purposes of preventing braided suture 1024 from sliding relative to suture support segment body 1020 in a direction opposite to the direction of inclination of barbs 1036. As can be seen in FIG. 18, the barbs 1036 are constructed such that if braided suture 1024 is pulled in the direction indicated by the arrow, the braided suture 1024 may pass freely with little resistance. However, if braided suture 1024 is pulled in the opposite direction, the barbs 1036 engage the braid of the braided suture 1024. Thus, braided suture 1024 is locked into position.

Figure 20:
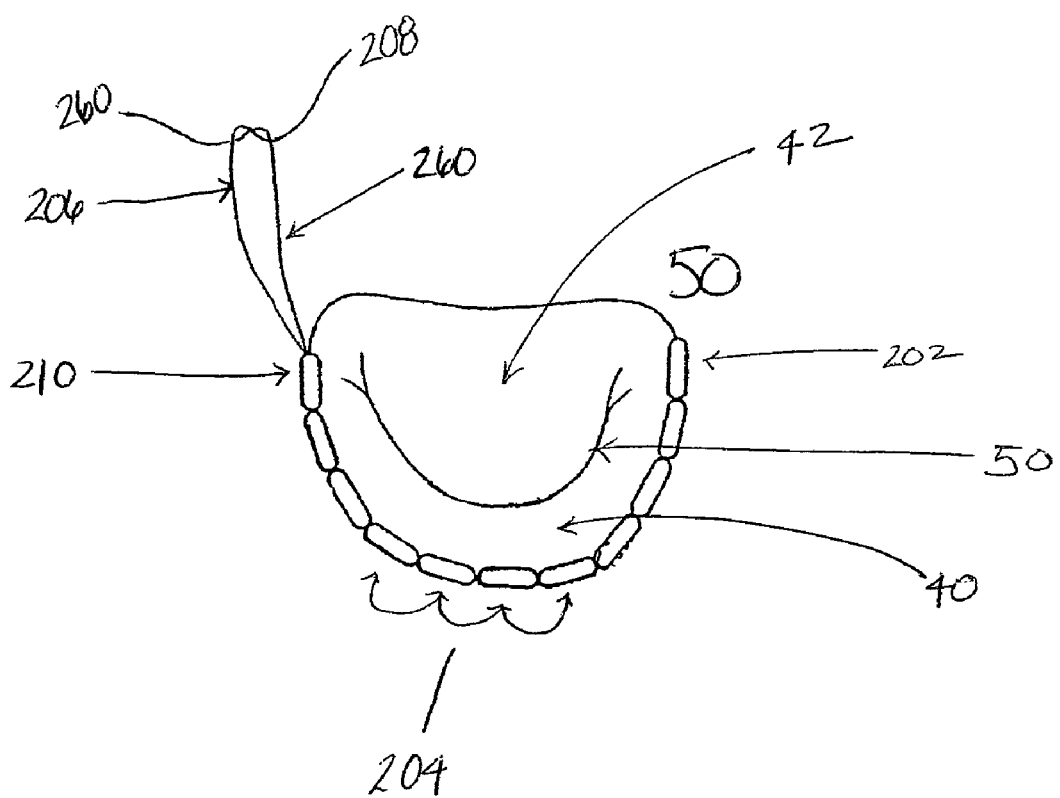
FIGS. 19-20 illustrate a method of attachment using a self-closing clip assembly.
Figure 19:
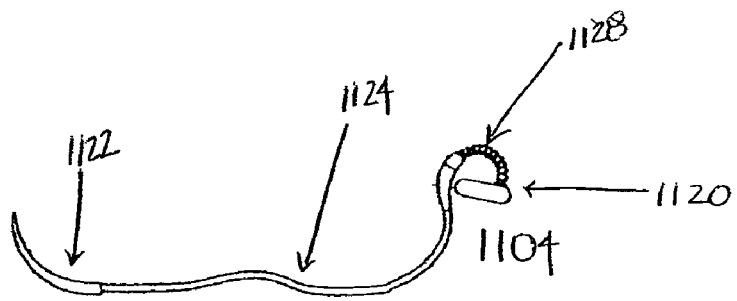
Figure 20:
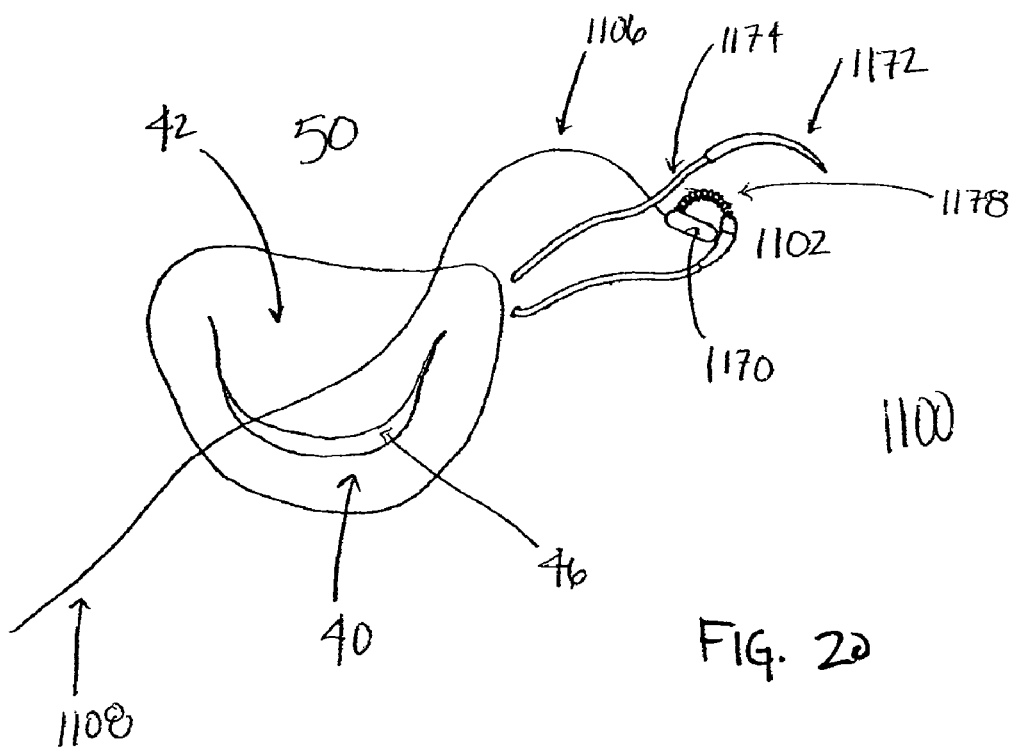

FIGS. 19-20 show parts of an annuloplasty system 1100 using suture support segments having a self-closing single-arm clip assembly to secure the suture support segment to the mitral valve annulus 50 instead of using traditional knotting. FIG. 19 is a detailed drawing of an intermediate suture support segment 1104 having an intermediate suture support segment body 1120, a self-closing single-arm clip assembly 1128, a suture 1124, and a surgical needle 1122. The self-closing single-arm clip assembly 1128 is generally U, C or J-shaped with two end points separated from each other when it is constrained to be in an open configuration, but tends to coil up to assume its naturally closed configuration if the constraint is removed. The self-closing single-arm clip assembly 1128 is attached to the intermediate suture support segment body 1120 by conventional means. Attached to the end of the self-closing single-arm clip assembly 1128 is a suture 1124 which has an attached surgical needle 1122.

FIG. 20 provides an illustration of the superior view of the mitral valve of a human heart. As depicted the mitral valve has a gap 46 between the anterior and posterior leaflets 42 and 40. FIG. 20 depicts how an anchor suture support segment 1102 of the current embodiment is attached to the mitral valve annulus 50. First, the surgeon guides the surgical needle 1172 to the surgical site and passes the surgical needle 1172 through the tissue of the mitral valve annulus 50 similar to interrupted suture placement and then pulls the suture 1174 until the self-closing single-arm clip assembly 1128 passes partially through the mitral valve tissue 50 such that the end point of the self-closing single-arm clip assembly 1128 which is connected to the suture 1174 completely passes through the mitral valve annulus 50. The other end of the self-closing single-arm clip assembly 1128 does not enter the mitral valve annulus 50 because it is attached to the anchor suture support segment body 1120 which prevents this end of the self-closing single-arm clip assembly 1128 from entering the mitral valve annulus 50. After the suture 1124 is released from the self-closing single-arm clip assembly 1128 the clip moves to its predetermined closed-loop configuration, reducing the distance between the two end points and securing the anchor suture support segment 1102 to the mitral valve annulus 50. The internal force of the clip keeps the anchor suture support segment 1102 firmly attached to the mitral valve annulus 50 and reduces the distance separating the two end points thereby reducing the portion of the circumference of the mitral valve annulus 50 between the two end points. After one clip is thus placed in the annulus, the same procedure is repeated with a plurality of other clips. The intermediate suture support segments 1104 are lowered down one-by-one over the supportive drawstring 1106 into position above the mitral valve annulus 50. Using this method a desired number of suture support segments can be linked together to form a line of linked segments of a desired length, corresponding to the unique size of the heart annulus of the individual patient.

FIGS. 21-26 illustrate a superior view of the repaired mitral valve of a human heart with a plurality of support segments in place. As depicted the mitral valve has a residual gap 46 between the anterior and posterior leaflets 42 and 40 as a result of a post-repair residual mitral valve incompetence. FIGS. 21-26 highlight one of the advantageous features of this annuloplasty system 1100 which is the ability to provide further adjustment or "fine tuning" of the repair once the annuloplasty system 1100 is implanted. In other words, the annuloplasty system 1100 may be adjusted in diameter during or after implantation which will allow the surgeon to correct certain technical errors that might have occurred during implantation and eliminate post-repair residual regurgitation.

FIG. 21 depicts how the plurality of suture support segments are slidably coupled with a supportive drawstring(s) and how the tissue between adjacent suture support segments will placate so that the circumference of the valve annulus will be reduced by applying tensile force to the supportive drawstring 1106 in a proximal direction. This will effectuate any residual annulus plication not already effectuated beneath suture support segments 1104. Tension may be adjusted on the supportive drawstring 1106 under direct visualization or while using ultrasound Doppler echocardiography for precise adjustment of the annular correction. When the entire circumference of the mitral valve annulus 50 has been sutured the mitral valve is tested for competence by distending the left ventricle with isotonic solution infused through a rubber-bulbed syringe. In case of residual regurgitation 46 shown in FIG. 21 the supportive drawstring(s) 1106 (FIGS. 20 and 21) can be used to further cinch the segments and thereby reduce the annular diameter and correct postrepair residual regurgitation (FIG. 23). Once proper adjustment is achieved, or in the absence of need for any adjustment, the supportive drawstring(s) 1106 are knotted together to maintain the desired degree of annular constriction and prevent further annular dilatation, thereby completing the annuloplasty (FIG. 22).

Figure 24:
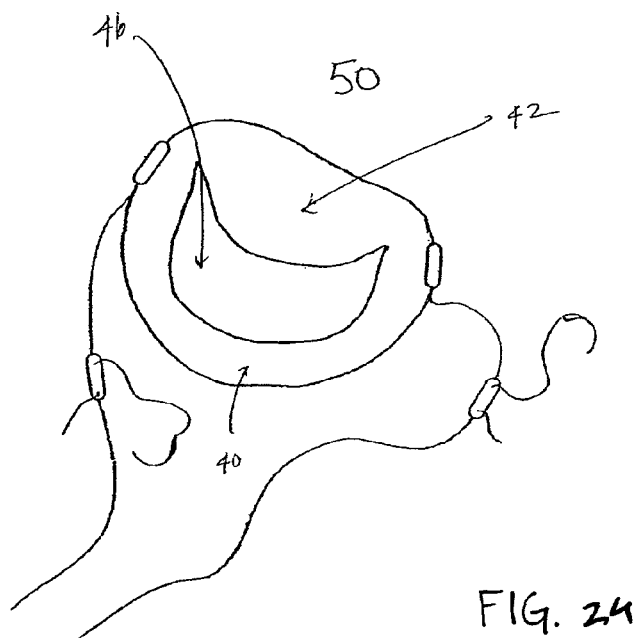
FIG. 24 illustrates a method of implanting suture support segments from opposite ends.

FIG. 24 illustrates a method of implanting suture support segments from opposite ends. In FIG. 24 two anchor suture support segments would be used and implanted at opposite ends of the mitral valve. The supportive drawstrings attached to the end of the anchor suture support segments would be used to lower the intermediate suture support segments onto the mitral valve.

Figure 25:
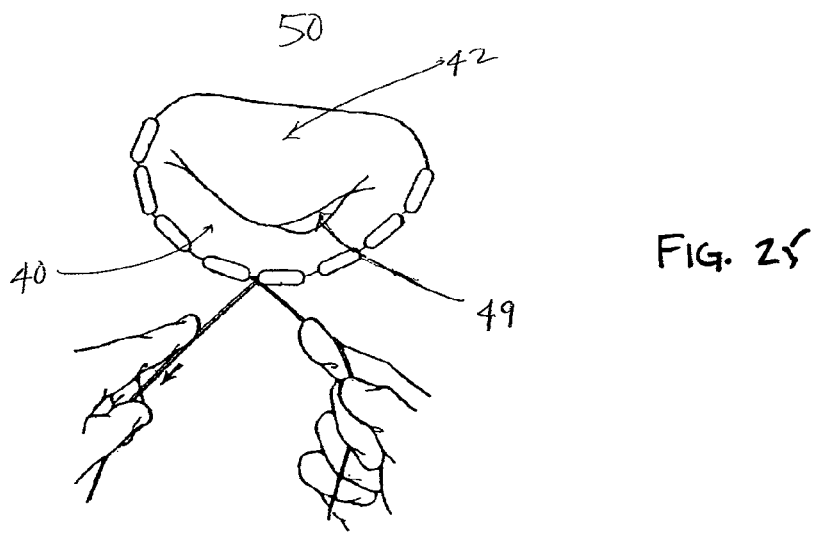
FIG. 25-26 show a method of using the supportive drawstrings to achieve a selective reduction of the inferior limb of the posterior annulus.
Figure 26:
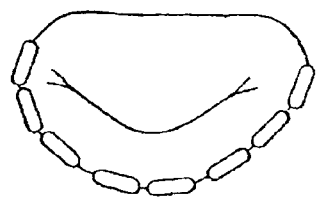

FIG. 25 shows how one of the two partial supportive drawstrings from the annuloplasty systems is used to achieve a selective reduction of the inferior limb of the posterior annulus. FIG. 25 depicts post-repair residual asymmetric incompetence 49 of the inferior limb of the posterior annulus an how a partial supportive drawstring corresponding to the area of asymmetric incompetence is pulled by the left hand of the surgeon to achieve a selective reduction of the inferior limb of the posterior annulus. FIG. 26 shows a completed system.

Another embodiment of this invention provides a suturing method for quickly attaching the suture support segments to the heart tissue without traditional knotting, which is not shown. Suture support segment has an eye sealed with a meltable material (polypropylene) being soft enough to be penetrated by the needle. Alternatively the meltable seal in the eye may have a central passage of a sufficient diameter to allow the needle and the suture to pass through the passage. In the annuloplasty procedure the needle would be passed through the heart annulus, and then the needle would be passed through the eye of the suture support segment. The suture pulled through the eye while the support segment is pushed down toward the heart annulus until the required tension is obtained. A specially constructed tool similar to a cable tie tension and cutter tool then will be used. The tool would have a tensioning mechanism for tensioning the suture to a predetermined tension setting, an ultrasonic welder and a cutting mechanism for cutting the excess portion of the suture tail after the desired tension is achieved and the suture joined to the polypropylene seal in a weld within the eye.

The suture is comprised of a melt-resistant braided core or a stainless steel core covered with a meltable sheath made from the same material as the seal in the eye of the support segment. Upon activation of the ultrasonic welder the meltable sheath of the suture and the meltable seal of the eye will melt so that the suture could attach to the support segment in the weld within the eye. The core of the suture will not melt and will remain intact so that the suture will not break upon melting of the meltable sheath of the suture. The tensioning and cutting tool will cut the excess portion of the suture tail after the desired tension is achieved and the suture joined to the polypropylene seal in a weld within the eye.

While the present invention has been illustrated by the description of exemplary embodiments thereof, and while the embodiments have been described in certain detail, it is not the intention of the Applicant to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the applicant's general inventive concept.

What is claimed is:

1. An annuloplasty system for repairing incompetent heart valves, comprising:
   (a) an adjustable heart valve reinforcing device adapted to be surgically implanted around a heart valve annulus and to reduce the circumference thereof by plicating annular tissue underneath the heart valve reinforcing device, wherein the valve reinforcing device includes:
      (i) a plurality of individual suture support components, wherein the plurality of suture support components includes:
         a) at least one anchor component, wherein the at least one anchor component further includes at least two channels passing lengthwise therethrough; and
         b) a plurality of intermediate components adapted to be implanted into the heart valve annulus after the anchor component, wherein each intermediate component further includes at least two channels passing lengthwise therethrough; and
   (b) anchoring means for attaching each individual suture support component in the plurality of suture support components around the heart valve annulus, wherein the anchoring means is integrated into each suture support component prior to implantation of the heart valve reinforcing device around a heart valve annulus, and wherein the anchoring means includes:
      (i) at least two sutures pre-attached to the at least one anchor component, wherein at least one of the sutures includes a surgical needle attached thereto; and
      (ii) at least two sutures pre-attached to each of the plurality of the intermediate components wherein at least one of the sutures includes a surgical needle attached thereto; and
   (c) constricting means for reducing the circumference of the adjustable heart valve reinforcing device, wherein a portion the constricting means passes through each individual suture support component and is operative to further reduce the circumference of the adjustable heart valve reinforcing device following implantation thereof around a heart valve annulus, and wherein the constricting means includes:
      (i) at least two supportive drawstrings, wherein one end of each drawstring is attached to one end of the at least one anchor component, wherein the drawstrings pass through the two channels in each intermediate component, and wherein the ends of the drawstrings are tied together over a final individual suture support component after the heart valve repair is completed.

2. The annuloplasty system of claim 1, wherein the supportive drawstrings comprise suture material, biodegradable suture material, a Teflon strip, a band, a filament, a wire, a strap, or combinations thereof.

3. The annuloplasty system of claim 1, wherein the individual suture support components are rigid or semi-rigid and are cylindrical, tubular, square, round, oval, or combinations thereof.

4. The annuloplasty system of claim 1, wherein the individual suture support components are rigid or semi-rigid and resist bucking when the anchoring means are tied and reduce the potential of over-plication of annular tissue underneath the suture support components when the anchoring means are tied.

5. The annuloplasty system of claim 1, wherein the individual suture support components are radio-opaque, inert, non-corrosive, non-thrombogenic, and biocompatible with blood and tissue.

6. The annuloplasty system of claim 1, wherein the individual suture support components further include a textured surface or coating for promoting tissue in-growth and reducing thromboembolism.

7. The annuloplasty system of claim 1, wherein the each of the plurality of individual suture support components includes at least one suture stored therein.

8. A method for surgically implanting the annuloplasty system of claim 1, comprising:
   (a) utilizing the anchoring means for securing the valve reinforcing device to the heart valve annulus, wherein securing the valve reinforcing device to the heart valve annulus reduces the circumference of the annulus by plicating annular tissue underneath the valve reinforcing device, and wherein utilizing the anchoring means further includes:
      (i) affixing the at least one anchor component to a dilated heart valve annulus by passing one of the surgical needles attached to the sutures on the at least one anchor component through the heart valve annulus;
      (ii) pulling the suture and surgical needle which has passed through the heart annulus until the at least one anchor component aligns with the heart valve annulus;

(iii) securing the at least one anchor component to the heart valve annulus by tying the ends of the sutures on the at least one anchor component together;

(iv) using the supportive drawstrings to guide one of the plurality of intermediate components through a minimally-invasive tube or small incision to the position above the heart valve annulus adjacent to the at least one anchor component;

(v) affixing one of the plurality of intermediate components to the heart valve annulus by passing one of the surgical needles attached to the sutures on one of the plurality of intermediate components through the heart valve annulus;

(vi) pulling the surgical needle and suture which has passed through the heart annulus until one of the plurality of intermediate components aligns with the heart valve annulus;

(vii) securing one of the plurality of intermediate components to the heart valve annulus by tying the ends of the sutures on one of the plurality of intermediate components together;

(viii) repeating steps (iv)-(vii) until the desired circumference around the heart valve annulus is covered by the plurality of intermediate components; and (ix) testing the annuloplasty system to verify that appropriate constriction has been achieved; and (b) utilizing the constricting means to reduce the circumference of the valve reinforcing device, wherein reducing the circumference of the valve reinforcing device further reduces the circumference of the heart valve annulus by plicating the annular tissue between adjacent components of the valve reinforcing device, and wherein utilizing the constricting means further includes:

(x) pulling both ends of the supportive drawstrings to the desired tension to further decrease the circumference of the heart valve annulus; and (xi) tying the ends of the supportive drawstrings around the final individual suture support component.

* * * * *